United States Patent
Butora et al.

(10) Patent No.: US 9,512,426 B2
(45) Date of Patent: *Dec. 6, 2016

(54) METHOD FOR RAPIDLY EVALUATING PERFORMANCE OF SHORT INTERFERING RNA WITH NOVEL CHEMICAL MODIFICATIONS

(71) Applicant: Sirna Therapeutics, Inc., Cambridge, MA (US)

(72) Inventors: Gabor Butora, Rahway, NJ (US); Ian W. Davies, Kenilworth, NJ (US); William Michael Flanagan, Menlo Park, CA (US); Wenlang Fu, Rahway, NJ (US); Denise M. Kenski, San Francisco, CA (US); Ning Qi, Rahway, NJ (US)

(73) Assignee: SIRNA THERAPEUTICS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/506,083

(22) Filed: Oct. 3, 2014

(65) Prior Publication Data

US 2015/0132761 A1    May 14, 2015

Related U.S. Application Data

(63) Continuation of application No. 13/515,454, filed as application No. PCT/US2010/059696 on Dec. 9, 2010, now Pat. No. 8,877,439.

(60) Provisional application No. 61/287,452, filed on Dec. 17, 2009.

(51) Int. Cl.
*C12Q 1/68* (2006.01)
*C07H 21/02* (2006.01)
(Continued)

(52) U.S. Cl.
CPC ........... *C12N 15/113* (2013.01); *C12N 15/111* (2013.01); *C12N 2310/14* (2013.01);
(Continued)

(58) Field of Classification Search
CPC ........................... C12N 15/111; C12N 15/113
USPC .......................................... 435/6.1; 536/23.1
See application file for complete search history.

(56) References Cited

U.S. PATENT DOCUMENTS 8,877,439 B2 * 11/2014 Butora et al. .................. 435/6.1
2009/0280567 A1 11/2009 Leake et al.
2010/0222414 A1 9/2010 Puri et al.

FOREIGN PATENT DOCUMENTS

WO  2004/090105 A2  10/2004
WO  2006/015389 A2  2/2006
WO  2009/020771 A2  2/2009

OTHER PUBLICATIONS

Chiu, Yi, et al, "siRNA function in RNAI: a chemical modification analysis"; RNA, vol. 9, No. 9, pp. 1034-1048, (2003).
(Continued)

*Primary Examiner* — Jezia Riley
(74) *Attorney, Agent, or Firm* — Lando & Anastasi, LLP

(57) ABSTRACT

It is an object of the instant invention to provide a method for the rapid evaluation of novel sugar modifications to be used in siRNA synthesis including the rapid evaluation of chemical modification patterns within the siRNA to effectuate increased stability and ultimately increased efficacy of a siRNA therapeutic. It is a further object of the instant invention to provide novel nucleosides useful for siRNA therapy.

18 Claims, 8 Drawing Sheets

(51) Int. Cl.
*C12N 15/113* (2010.01)
*C12N 15/11* (2006.01)

(52) U.S. Cl.
CPC ..... *C12N2310/32* (2013.01); *C12N 2310/322* (2013.01); *C12N 2310/331* (2013.01); *C12N 2320/11* (2013.01); *C12N 2320/51* (2013.01)

(56) References Cited

OTHER PUBLICATIONS

Gabor Butora et al: "Nucleoside Optimization for RNAi: A High-Throughput Platform", Journal of the American Chemical Society, vol. 133, No. 42, Oct. 26, 2011 (Oct. 26, 2011), pp. 16766-16769, XP055057703, ISSN: 0002-7863, DOI: 10.1021/ja2068774.
International Preliminary Report on Patentability & Written Opinion for PCT/US2010/05969 dated Jun. 19, 2012.
International Search Report for PCT/US10/59695 dated Jun. 1, 2011.
Jackson, et al., "Position-Specific Chemical Modification of siRNAs reduced "Off-target" transcript silencing", RNA, vol. 12, No. 7, pp. 1197-1205 (2006).
Loakes D: "Survey and summary: The applications of universal DNA base analogues", Nucleic Acids Research, vol. 29, No. 12, Jun. 15, 2001 (Jun. 15, 2001), pp. 2437-2447, XP002487174, ISSN: 0305-1048, DOI: 10.1093/NAR/29.12.2437.
Rajeev Kallanthottathil G et al: "siRNAs with a Universal Base", Abstracts of Papers American Chemical Society, vol. 234, Aug. 2007 (Aug. 2007), p. CARB 42, XP008165842, ISSN: 0065-7727 & 234th National Meeting of the American-Chemical-Society; Boston, MA, USA; Aug. 19-23, 2007.
Supplemental EP Search Report for EP Application 10 84 2465, dated Nov. 19, 2013.

\* cited by examiner

SEQUENCE LISTING

<160> NUMBER OF SEQ ID NOS: 5

<210> SEQ ID NO 1
<211> LENGTH: 19
<212> TYPE: RNA
<213> ORGANISM: Artificial Sequence
<220> FEATURE:
<223> OTHER INFORMATION: Synthetic

<400> SEQUENCE: 1
auuucaggaa uuguuaaag                                         19

<210> SEQ ID NO 2
<211> LENGTH: 19
<212> TYPE: RNA
<213> ORGANISM: Artificial Sequence
<220> FEATURE:
<223> OTHER INFORMATION: Synthetic

<400> SEQUENCE: 2
uucaguguga ugacacuug                                         19

<210> SEQ ID NO 3
<211> LENGTH: 19
<212> TYPE: RNA
<213> ORGANISM: Artificial Sequence
<220> FEATURE:
<223> OTHER INFORMATION: Synthetic

<400> SEQUENCE: 3
aaugcauuga gggccuugc                                         19

```
<210> SEQ ID NO 4
<211> LENGTH: 19
<212> TYPE: RNA
<213> ORGANISM: Artificial Sequence
<220> FEATURE:
<223> OTHER INFORMATION: Synthetic

<400> SEQUENCE: 4
aucaaauuug gguucaaug                                                    19

<210> SEQ ID NO 5
<211> LENGTH: 19
<212> TYPE: RNA
<213> ORGANISM: Artificial Sequence
<220> FEATURE:
<223> OTHER INFORMATION: Synthetic

<400> SEQUENCE: 5
uagacgucuu ugcugacug                                                    19
```

METHOD FOR RAPIDLY EVALUATING PERFORMANCE OF SHORT INTERFERING RNA WITH NOVEL CHEMICAL MODIFICATIONS

BACKGROUND OF THE INVENTION

RNA interference (RNAi) is an evolutionarily conserved cellular mechanism of post transcriptional gene silencing found in fungi, plants and animals that uses small RNA molecules to guide the inhibition of gene expression in a sequence-specific manner. Its principal role is suppression of potentially harmful genetic material (Buchon et al., "RNAi: a defensive RNA-silencing against viruses and transposable elements", Heredity, 96(2), 95-202, 2006). Among the most powerful stimuli capable of triggering the RNAi machinery are long double-stranded ribonucleic acids (dsRNA) often associated with viral replication. These long duplexes are degraded into short double-stranded fragments (approximately 21-23 nucleotides long) known as small interfering RNA (siRNA) by an RNAse III-type enzyme, Dicer (Bernstein et al., "Role for a bidentate ribonuclease in the initiation step of RNA interference" Nature, 409, 363-366, 2001). The siRNA is then transferred onto the RNA-induced silencing complex (RISC) (Tuschl et al., "RISC is a 5'-phosphomonoester-producing RNA endonuclease", Genes & Development, 18: 975-980, 2004) which becomes activated upon removal of one of the strands (the "passenger" or "sense" strand). The remaining strand (the "guide" or "antisense" strand) then directs the activated RISC in a sequence-specific degradation of complementary target messenger RNA (mRNA). Since the selection of engaged mRNA is controlled solely by Crick-Watson base-pairing (Watson, J. D, Crick, F. H "Molecular structure of nucleic acids", Nature, (171), 737-738, 1953) between the guide strand and the target mRNA, the RNAi pathway can be directed to destruct any mRNA of a known sequence. In turn, this allows for suppression, or knock-down, of any gene from which it was generated preventing the synthesis of the target protein. This unprecedented control has wide reaching therapeutic consequences.

While long dsRNA will also inevitably trigger a sequence independent immunogenic reaction, much smaller siRNA duplexes introduced exogenously were found to be equally effective triggers of RNAi (Zamore, P. D., Tuschl, T., Sharp, P. A., Bartel, D. P.; "RNAi: double-stranded RNA directs the ATP-dependent cleavage of mRNA at 21 to 23 nucleotide intervals." Cell, 101, 25-33, 2000). According to this, artificially synthesized 21 nucleotide long RNA duplexes typically containing 2-nt 3'-overhangs, can be used to manipulate any therapeutically relevant biochemical system, including ones which are not accessible through traditional small molecule control.

In order to realize this immense therapeutic potential of RNAi, many properties of siRNAs need to be optimized (Castanotto et al. "The promises and pitfalls of RNA interference-based therapeutics", Nature, 457, 426-457, 2009). Due to their large molecular weight and polyanionic nature unmodified siRNAs do not freely cross the cell membranes, and thus development of special delivery systems is required (White, P. J. "Barriers to successful delivery of short interfering RNA after systemic administration" Clin. Exp. Pharmacol. Physiol. 35, 1371-1376, 2008). Equally important is optimization of potency (Koller, E. et al. "Competition for RISC binding predicts in vitro potency of siRNA" Nucl. Acids Res. 34, 4467-4476, 2006), stability (Damha et al. "Chemically modified siRNA: Tools and applications" Drug Discovery Today, 13(19/20), 842-855, 2008), and immunogenicity (Sioud "Innate sensing of self and non-self RNAs by Toll-like receptors", TRENDS in Molecular Medicine, 12(4), 167-176, 2006).

The guide-strand-mediated sequence-specific cleavage activity of the RNA-induced silencing complex (RISC) is associated with an RNase H-type endonuclease Argonaute (Ago) (Tanaka Hall "Structure and Function of Argonaute Proteins", Structure, 13, 1403-1408, 2005). An X-ray crystal structure of Argonaute 2 (Ago2) containing a chemically modified guide strand (Patel at al., "Structure of the guide-strand-containing argonaute silencing complex", Nature, 456(13), 209-213, 2008, Patel at al., "Structure of an argonaute silencing complex with a seed-containing guide DNA and target RNA duplex", Nature, 456(13), 921-927, 2008) revealed that nucleotides 2 through 8 of the guide strand (referred to as "seed region") are preassembled in a A-form helix and that the guide strand makes contact with the surface of the Ago2 through its sugar/phosphodiester backbone. This observation bodes well for the importance of the seed region in the initial recognition of the complementary mRNA, since an effective mRNA/guide strand interaction requires the heterobases to be accessible from the cytoplasm, hence to point away from the receptor surface.

Chemical modifications of the sugar/phosphodiester backbone of the siRNA's guide strand are therefore expected to have profound effect on the siRNA/Ago2 interaction. This offers a way to optimize the performance of this complex. Such an improved interaction should result in increased siRNA/Ago2 binding selectivity, more effective strand selection and passenger strand cleavage, improved catalytic turnover, siRNA/Ago2 complex stability and product release. Moreover, chemically modified siRNA duplexes are expected to be quite resistant to RNase mediated cleavage (increased half-life), decreased affinity to Toll-like receptors (TLR) and dsRNA-dependent protein kinase (PKR), resulting in decreased immunogenicity (Liang et al. "RNA Interference with Chemically Modified siRNA", Cur. Topics Med. Chem., 6, 893-900, 2006).

Most chemically modified nucleosides used today in RNAi were synthesized to convey enzymatic stability to RNA oligomers and their design was not guided by siRNA/Ago2 binding considerations. Even though collection of SAR data relevant to this interaction would be highly beneficial, a hypothesis driven design of such novel nucleosides is clearly hampered by the chemical complexity of the associated chemistry. Assuming that the interaction of the siRNA's guide strand with the Ago2 surface is primarily static, such an effort would require independent SAR data collection for each nucleotide along the siRNA oligomer separately, since the local Ago2 surface relevant to each particular position is different. Furthermore, such SAR study would require the synthesis of sugar-modified nucleosides containing all four canonical bases since a systematic investigation would require a use of a sequence-specific siRNA. In theory, at least 21 separate siRNA oligomers, containing one instance the modified nucleoside each (positions 1 through 21, "walkthrough") would be necessary, requiring the synthesis of considerable quantities of each monomer. This complexity renders the interrogation of such a huge chemical space intractable.

We have realized that use of universal bases in place of canonical heterocycles would greatly simplify the problem. In general, a universal base is a heterocycle capable of an isoenergetic interaction with each one of the canonical heterobases, (Adenine, Guanine, Uracil and Cytosine) while part of a double helix. The simplest example of such a universal interaction is a hydrogen atom corresponding to the removal of the heterocycle and more complex examples are 3-nitro-pyrrole, imidazole-4-carboxamide, 5-nitro-indole, inosine and others. We have argued that the use of such universal base would not only eliminate the need for synthesis of all four canonical nucleosides, it would also greatly reduce the complexity of the associated chemical syntheses.

Replacement of a canonical heterocycle with a universal base was expected to affect the efficiency of such a siRNA/Ago2 assembly and this should result in a position specific decrease of target gene knockdown. In order to asses this effect, we have synthesized ApoB-specific siRNA oligomers containing such universal bases while keeping the sugar of the nucleoside unmodified. We have indeed observed a base dependent position specific change in overall knockdown performance. In general, the effect of the universal base was more pronounced in the center of the RNA oligomer and the effect of simple base-surrogates such as hydrogen (removal of the entire heterocycle) was more profound.

Using the position-specific knockdown data obtained with universal base-surrogates as the new baseline, we synthesized a series of sugar-modified base-surrogate containing nucleosides and evaluated them under conditions similar to those used to obtain the baseline data. We argued that if the performance of the base-surrogate-containing sugar-modified nucleoside surpasses that of the base-surrogate containing canonical sugar, this relationship will be reflected also in the improved performance of the sugar-modified full canonical nucleoside and vice versa. This approach would allow us to rapidly evaluate prospective sugar modification and perform the syntheses of the full nucleosides only when the particular modification is found beneficial in this simplified platform. While this novel platform does not allow for a prediction of useful modifications, it can dramatically increase the rate of SAR data collection.

SUMMARY OF THE INVENTION

It is an object of the instant invention to provide a method for the rapid evaluation of novel sugar modifications to be used in siRNA synthesis including the rapid evaluation of chemical modification patterns within the siRNA to effectuate increased stability and ultimately increased efficacy of a siRNA therapeutic. It is a further object of the instant invention to provide novel nucleosides useful for siRNA therapy.

DETAILED DESCRIPTION OF THE INVENTION

Figure 1A:
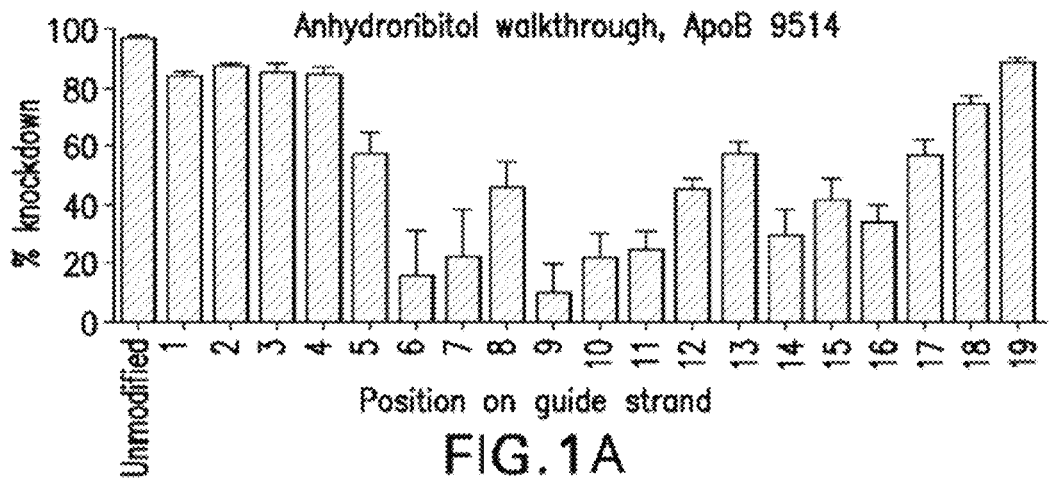
FIGS. 1A, 1B and 1C: Position-dependent mRNA degradation of the universal bases.

In an embodiment, the invention features a method for an efficient and streamlined process for the evaluation of novel chemical modifications in an siRNA, said method comprising: a) generating a siRNA oligomer with 1 or more sugar un-modified universal base containing nucleosides; b) obtaining position-specific data to create a baseline data; c) generating a siRNA oligomer with 1 or more sugar modified universal base containing nucleosides; and d) obtaining position-specific data and comparing that data to the baseline data.

In an embodiment, the invention features a method for an efficient and streamlined process for the evaluation of novel chemical modifications in an siRNA, said method comprising: a) generating a siRNA oligomer with 1 or more sugar un-modified universal base containing nucleosides; b) obtaining position-specific knockdown data to create a target gene knockdown baseline data; c) generating a siRNA oligomer with 1 or more sugar modified universal base containing nucleosides; and d) obtaining position-specific knockdown data and comparing that data to the knockdown baseline data.

In an embodiment, the invention features a method for an efficient and streamlined process for the evaluation of novel chemical modifications in an siRNA, said method comprising: a) generating a siRNA oligomer with 1 or more sugar un-modified universal base containing nucleosides; b) obtaining position-specific knockdown data to create a target gene knockdown baseline data; c) generating a siRNA oligomer with 1 or more sugar modified universal base containing nucleosides; and d) obtaining position-specific knockdown data and comparing that data to the knockdown baseline data to determine if the performance of said sugar modification in that siRNA oligomer is beneficial to knockdown efficiency.

In an embodiment, the invention features a method for an efficient and streamlined process for the evaluation of novel chemical modifications in an siRNA, said method comprising: a) generating a siRNA oligomer with 1 or more sugar un-modified universal base containing nucleosides, wherein the universal base is a hydrogen atom or inosine; b) obtaining position-specific data to create a baseline data; c) generating a siRNA oligomer with 1 or more sugar modified universal base containing nucleosides; and d) obtaining position-specific data and comparing that data to the baseline data.

In an embodiment, the invention features a method for an efficient and streamlined process for the evaluation of novel chemical modifications in an siRNA, said method comprising: a) generating a siRNA oligomer with 1 or more sugar un-modified universal base containing nucleosides, wherein the universal base is a hydrogen atom or inosine; b) obtaining position-specific knockdown data to create a target gene knockdown baseline data; c) generating a siRNA oligomer with 1 or more sugar modified universal base containing nucleosides; and d) obtaining position-specific knockdown data and comparing that data to the knockdown baseline data.

In another embodiment, the invention features a siRNA which contains 1 or more 2'-sugar modification(s), wherein the 2'-sugar modification(s) is represented in Formula B,

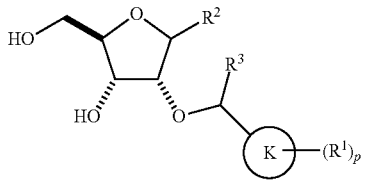

wherein, p is 0, 1, 2 or 3;

Ring K is aryl, heterocyclyl or a $(C_3\text{-}C_8)$cycloalkyl;

$R^1$ is independently selected from: OH, COOH, $CF_3$, $NO_2$, halo, $(C_1\text{-}C_6)$alkyl, $O(C_1\text{-}C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1\text{-}C_6)$alkyl;

$R^2$ is selected from: a canonical or universal base; and $R^3$ is selected from H and $(C_1\text{-}C_6)$alkyl;

or a pharmaceutically acceptable salt or stereoisomer thereof.

In the embodiment above the siRNA can be a chemically modified siRNA.

In another embodiment, the invention features a siRNA which contains 1 or more 2'-sugar modification(s), wherein the 2'-sugar modification(s) is represented in Formula B,

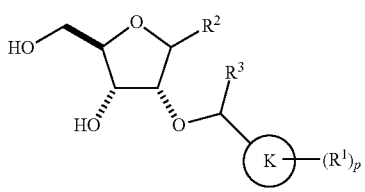

wherein, p is 0, 1, 2 or 3;

Ring K is aryl, heterocyclyl or a $(C_3\text{-}C_8)$cycloalkyl, with the proviso that when aryl is phenyl, then p is not 0;

$R^1$ is independently selected from: OH, COOH, $CF_3$, $NO_2$, halo, $(C_1\text{-}C_6)$alkyl, $O(C_1\text{-}C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1\text{-}C_6)$alkyl;

$R^2$ is selected from: a canonical or universal base; and $R^3$ is selected from H and $(C_1\text{-}C_6)$alkyl;

or a pharmaceutically acceptable salt or stereoisomer thereof.

In the embodiment above the siRNA can be a chemically modified siRNA.

In another embodiment, the invention features a siRNA which contains a 2'-sugar modification(s) at positions 3, 5, 6, 8, 15, 17 and 19 wherein the 2'-sugar modification(s) is represented in Formula B,

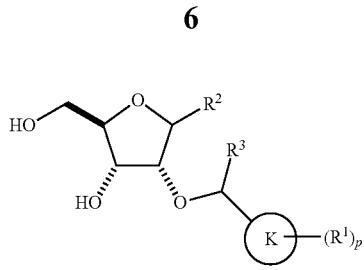

wherein, p is 0, 1, 2 or 3;

Ring K is aryl, heterocyclyl or a $(C_3\text{-}C_8)$cycloalkyl;

$R^1$ is independently selected from: OH, COOH, $CF_3$, $NO_2$, halo, $(C_1\text{-}C_6)$alkyl, $O(C_1\text{-}C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1\text{-}C_6)$alkyl;

$R^2$ is selected from: a canonical or universal base; and $R^3$ is selected from H and $(C_1\text{-}C_6)$alkyl;

or a pharmaceutically acceptable salt or stereoisomer thereof.

In another embodiment, the invention features a siRNA which contains a 2'-sugar modification(s) at positions 3, 5, 6, 8, 15, 17 and 19 wherein the 2'-sugar modification(s) is represented in Formula B,

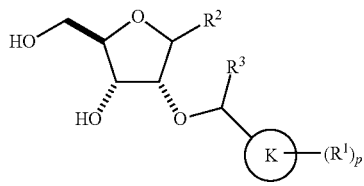

wherein, p is 0, 1, 2 or 3;

Ring K is aryl, heterocyclyl or a $(C_3\text{-}C_8)$cycloalkyl, with the proviso that when aryl is phenyl, then p is not 0;

$R^1$ is independently selected from: OH, COOH, $CF_3$, $NO_2$, halo, $(C_1\text{-}C_6)$alkyl, $O(C_1\text{-}C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1\text{-}C_6)$alkyl;

$R^2$ is selected from: a canonical or universal base; and $R^3$ is selected from H and $(C_1\text{-}C_6)$alkyl;

or a pharmaceutically acceptable salt or stereoisomer thereof.

In the embodiment above the siRNA can be a chemically modified siRNA.

In another embodiment, the invention features a siRNA which contains a 2'-sugar modification(s) at positions 3, 5, 6, 8, 15, 17 or 19 wherein the 2'-sugar modification(s) is represented in Formula B,

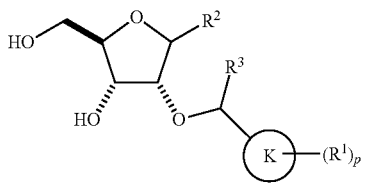

wherein, p is 0, 1, 2 or 3;

Ring K is aryl, heterocyclyl or a $(C_3-C_8)$cycloalkyl;

$R^1$ is independently selected from: OH, COOH, $CF_3$, $NO_2$, halo, $(C_1-C_6)$alkyl, $O(C_1-C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1-C_6)$alkyl;

$R^2$ is selected from: a canonical or universal base; and $R^3$ is selected from H and $(C_1-C_6)$alkyl;

or a pharmaceutically acceptable salt or stereoisomer thereof.

In another embodiment, the invention features a siRNA which contains a 2'-sugar modification(s) at positions 3, 5, 6, 8, 15, 17 or 19 wherein the 2'-sugar modification(s) is represented in Formula B,

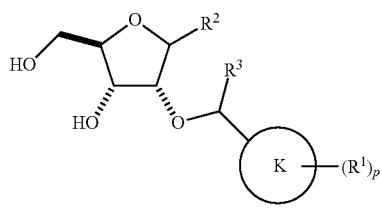

wherein, p is 0, 1, 2 or 3;

Ring K is aryl, heterocyclyl or a $(C_3-C_8)$cycloalkyl, with the proviso that when aryl is phenyl, then p is not 0;

$R^1$ is independently selected from: OH, COOH, $CF_3$, $NO_2$, halo, $(C_1-C_6)$alkyl, $O(C_1-C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1-C_6)$alkyl;

$R^2$ is selected from: a canonical or universal base; and $R^3$ is selected from H and $(C_1-C_6)$alkyl;

or a pharmaceutically acceptable salt or stereoisomer thereof.

In the embodiment above the siRNA can be a chemically modified siRNA.

In another embodiment, the invention features a siRNA which contains a 2'-sugar modification(s) at positions 5, 8, 15 and 19 wherein the 2'-sugar modification(s) is represented in Formula B,

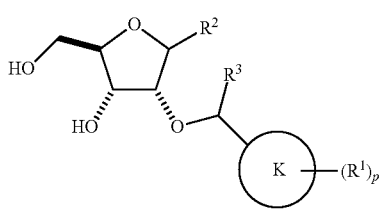

wherein, p is 0, 1, 2 or 3;

Ring K is aryl, heterocyclyl or a $(C_3-C_8)$cycloalkyl;

$R^1$ is independently selected from: OH, COOH, $CF_3$, $NO_2$, halo, $(C_1-C_6)$alkyl, $O(C_1-C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1-C_6)$alkyl;

$R^2$ is selected from: a canonical or universal base; and $R^3$ is selected from H and $(C_1-C_6)$alkyl;

or a pharmaceutically acceptable salt or stereoisomer thereof.

In another embodiment, the invention features a siRNA which contains a 2'-sugar modification(s) at positions 5, 8, 15 and 19 wherein the 2'-sugar modification(s) is represented in Formula B,

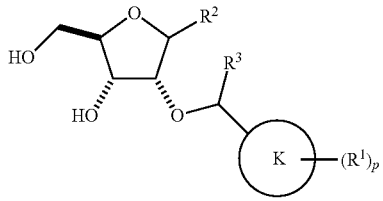

wherein, p is 0, 1, 2 or 3;

Ring K is aryl, heterocyclyl or a $(C_3-C_8)$cycloalkyl, with the proviso that when aryl is phenyl, then p is not 0;

$R^1$ is independently selected from: OH, COOH, $CF_3$, $NO_2$, halo, $(C_1-C_6)$alkyl, $O(C_1-C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1-C_6)$alkyl;

$R^2$ is selected from: a canonical or universal base; and $R^3$ is selected from H and $(C_1-C_6)$alkyl;

or a pharmaceutically acceptable salt or stereoisomer thereof.

In the embodiment above the siRNA can be a chemically modified siRNA.

In another embodiment, the invention features a siRNA which contains a 2'-sugar modification(s) at positions 5, 8, 15 or 19 wherein the 2'-sugar modification(s) is represented in Formula B,

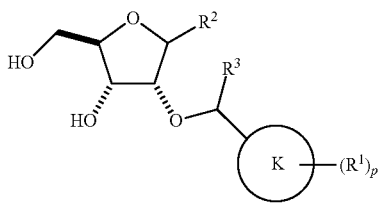

wherein, p is 0, 1, 2 or 3;

Ring K is aryl, heterocyclyl or a $(C_3$-$C_8)$cycloalkyl;

$R^1$ is independently selected from: OH, COOH, $CF_3$, $NO_2$, halo, $(C_1$-$C_6)$alkyl, $O(C_1$-$C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1$-$C_6)$alkyl;

$R^2$ is selected from: a canonical or universal base; and $R^3$ is selected from H and $(C_1$-$C_6)$alkyl;

or a pharmaceutically acceptable salt or stereoisomer thereof.

In another embodiment, the invention features a siRNA which contains a 2'-sugar modification(s) at positions 5, 8, 15 or 19 wherein the 2'-sugar modification(s) is represented in Formula B,

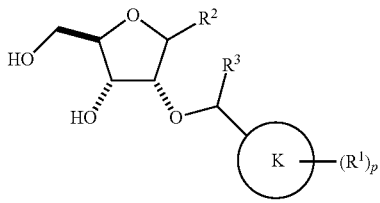

wherein, p is 0, 1, 2 or 3;

Ring K is aryl, heterocyclyl or a $(C_3$-$C_8)$cycloalkyl, with the proviso that when aryl is phenyl, then p is not 0;

$R^1$ is independently selected from: OH, COOH, $CF_3$, $NO_2$, halo, $(C_1$-$C_6)$alkyl, $O(C_1$-$C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1$-$C_6)$alkyl;

$R^2$ is selected from: a canonical or universal base; and $R^3$ is selected from H and $(C_1$-$C_6)$alkyl;

or a pharmaceutically acceptable salt or stereoisomer thereof.

In the embodiment above the siRNA can be a chemically modified siRNA.

In another embodiment, the invention features a siRNA which contains a 2'-sugar modification(s) at positions 8, 15 and 19 wherein the 2'-sugar modification(s) is represented in Formula B,

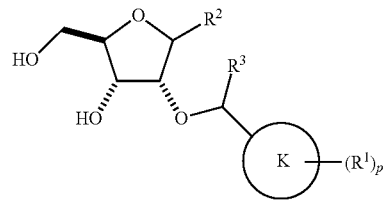

wherein, p is 0, 1, 2 or 3;

Ring K is aryl, heterocyclyl or a $(C_3$-$C_8)$cycloalkyl; $R^1$ is independently selected from: OH, COOH, $CF_3$, $NO_2$, halo, $(C_1$-$C_6)$alkyl, $O(C_1$-$C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1$-$C_6)$alkyl;

$R^2$ is selected from: a canonical or universal base; and $R^3$ is selected from H and $(C_1$-$C_6)$alkyl;

or a pharmaceutically acceptable salt or stereoisomer thereof.

In the embodiment above the siRNA can be a chemically modified siRNA.

In another embodiment, the invention features a siRNA which contains a 2'-sugar modification(s) at positions 8, 15 and 19 wherein the 2'-sugar modification(s) is represented in Formula B,

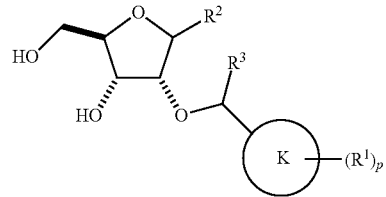

wherein, p is 0, 1, 2 or 3;

Ring K is aryl, heterocyclyl or a $(C_3$-$C_8)$cycloalkyl, with the proviso that when aryl is phenyl, then p is not 0;

$R^1$ is independently selected from: OH, COOH, $CF_3$, $NO_2$, halo, $(C_1$-$C_6)$alkyl, $O(C_1$-$C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1$-$C_6)$alkyl;

$R^2$ is selected from: a canonical or universal base; and $R^3$ is selected from H and $(C_1$-$C_6)$alkyl;

or a pharmaceutically acceptable salt or stereoisomer thereof.

In the embodiment above the siRNA can be a chemically modified siRNA.

In another embodiment, the invention features a siRNA which contains a 2'-sugar modification(s) at positions 8, 15 or 19 wherein the 2'-sugar modification(s) is represented in Formula B,

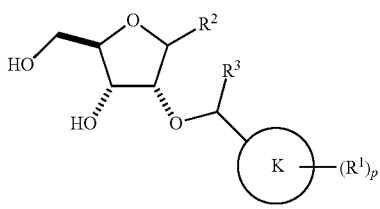

wherein, p is 0, 1, 2 or 3;

Ring K is aryl, heterocyclyl or a $(C_3-C_8)$cycloalkyl;

$R^1$ is independently selected from: OH, COOH, $CF_3$, $NO_2$, halo, $(C_1-C_6)$alkyl, $O(C_1-C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1-C_6)$alkyl;

$R^2$ is selected from: a canonical or universal base; and $R^3$ is selected from H and $(C_1-C_6)$alkyl;

or a pharmaceutically acceptable salt or stereoisomer thereof.

In the embodiment above the siRNA can be a chemically modified siRNA.

In another embodiment, the invention features a siRNA which contains a 2'-sugar modification(s) at positions 8, 15 or 19 wherein the 2'-sugar modification(s) is represented in Formula B,

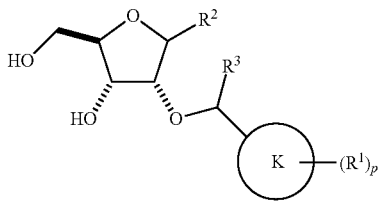

wherein, p is 0, 1, 2 or 3;

Ring K is aryl, heterocyclyl or a $(C_3-C_8)$cycloalkyl, with the proviso that when aryl is phenyl, then p is not 0;

$R^1$ is independently selected from: OH, COOH, $CF_3$, $NO_2$, halo, $(C_1-C_6)$alkyl, $O(C_1-C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1-C_6)$alkyl;

$R^2$ is selected from: a canonical or universal base; and $R^3$ is selected from H and $(C_1-C_6)$alkyl;

or a pharmaceutically acceptable salt or stereoisomer thereof.

In the embodiment above the siRNA can be a chemically modified siRNA.

In another embodiment, the invention features a compound illustrated by the Formula A:

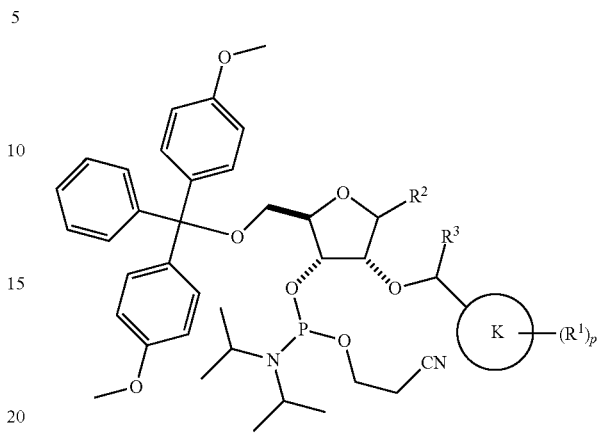

wherein, p is 0, 1, 2 or 3;

Ring K is aryl, heterocyclyl or a $(C_3-C_8)$cycloalkyl;

$R^1$ is independently selected from: OH, COOH, $CF_3$, $NO_2$, halo, $(C_1-C_6)$alkyl, $O(C_1-C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1-C_6)$alkyl;

$R^2$ is selected from: a canonical or universal base; and $R^3$ is selected from H and $(C_1-C_6)$alkyl;

or a pharmaceutically acceptable salt or stereoisomer thereof.

In another embodiment, the invention features a compound illustrated by the Formula A:

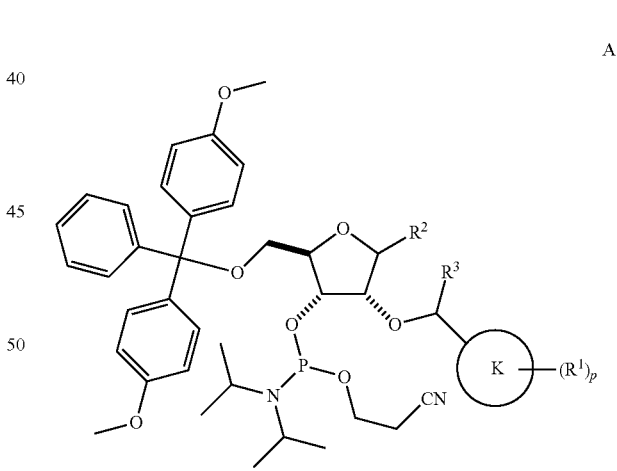

wherein, p is 0, 1, 2 or 3;

Ring K is aryl, heterocyclyl or a $(C_3-C_8)$cycloalkyl, with the proviso that when aryl is phenyl, then p is not 0;

$R^1$ is independently selected from: OH, COOH, $CF_3$, $NO_2$, halo, $(C_1-C_6)$alkyl, $O(C_1-C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1-C_6)$alkyl;

$R^2$ is selected from: a canonical or universal base; and $R^3$ is selected from H and $(C_1-C_6)$alkyl;

or a pharmaceutically acceptable salt or stereoisomer thereof.

Specific compounds of the instant invention include:

1,4-Anhydro-2-O-benzyl-5-O-[bis(4-methoxyphenyl)(phenyl)methyl]-3-O-[(2-cyanoethoxy) (dipropan-2-ylamino)phosphanyl]-D-ribitol;

1,4-anhydro-5-O-[bis(4-methoxyphenyl)(phenyl)methyl]-2-O-(4-tert-butylbenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(4-methylbenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(2-fluorobenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(3-fluorobenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(4-fluorobenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(3-trifluoromethylbenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(4-trifluoromethylbenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(2-fluoro-4-trifluoromethylbenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(3,5-difluorobenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(2,6-difluorobenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(2,4-difluorobenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(2-difluoromethoxybenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(3-fluoro-4-chlorobenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(2-chlorobenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(3-chlorobenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(3-chloro-5-trifluoromethoxybenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(4-methoxybenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(3-methoxybenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(2-methoxybenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(3-methylbenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(3,5-dimethylbenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(4-isopropylbenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(4-phenylbenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(2-naphthyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(3-nitrobenzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(4-(tetrahydropyran-4-yl)benzyl)-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-([4-(5-methyl-1,3,4-oxadiazol-2-yl)benzyl]-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-ara-benzyl]-3-O-[(2-cyanoethoxy)(dipropan-2-ylamino)phosphanyl]-D-ribitol;

1,4-anhydro-5-O-[bis(4-methoxyphenyl)(phenyl)methyl]-2-O-(2-methylbenzyl)-3-O-[(2-cyanoethoxy)(dipropan-2-ylamino)phosphanyl]-D-ribitol;

2'-O-benzyl-5'-O-[bis(4-methoxyphenyl)(phenyl)methyl]-3'-O-[(2-cyanoethoxy)(dipropan-2-ylamino)phosphanyl]inosine;

2'-O-(2-methylbenzyl)-5'-O-[bis(4-methoxyphenyl)(phenyl)methyl]-3'-O-[(2-cyanoethoxy(dipropan-2-ylamino)phosphanyl]inosine;

2'-O-(2-naphthyl)-5'-O-[bis(4-methoxyphenyl)(phenyl)methyl]-3'-O-[(2-cyanoethoxy(dipropan-2-ylamino)phosphanyl]inosine;

2'-O-(2-difluoromethoxybenzyl)-5'-O-[bis(4-methoxyphenyl)(phenyl)methyl]-3'-O-[(2-cyanoethoxy(dipropan-2-ylamino)phosphanyl]inosine;

2'-O-(3-methoxybenzyl)-5'-O-[bis(4-methoxyphenyl)(phenyl)methyl]-3'-O-[(2-cyanoethoxy(dipropan-2-ylamino)phosphanyl]inosine;

2'-O-(2-methylbenzyl)-5'-O-[bis(4-methoxyphenyl)(phenyl)methyl]-3'-O-[(2-cyanoethoxy(dipropan-2-ylamino)phosphanyl]inosine;

2'-O-(pyridin-2-ylmethy)-5'-O-[bis(4-methoxyphenyl)(phenyl)methyl]-3'-O-[(2-cyanoethoxy(dipropan-2-ylamino)phosphanyl]inosine;

2'-O-(pyridin-3-ylmethy)-5'-O-[bis(4-methoxyphenyl)(phenyl)methyl]-3'-O-[(2-cyanoethoxy(dipropan-2-ylamino)phosphanyl]inosine;

2'-O-(pyridin-4-ylmethy)-5'-O-[bis(4-methoxyphenyl)(phenyl)methyl]-3'-O-[(2-cyanoethoxy(dipropan-2-ylamino)phosphanyl]inosine;

9-{2-O-(4-bromobenzyl)-5-O-[bis(4-methoxyphenyl)(phenyl)methyl]-3-O-[(2-cyanoethoxy)(dipropan-2-ylamino)phosphanyl]-b-D-ribofuranosyl}-6-[2-(trimethylsilyl)ethoxy]-9H-purine;

9-{2-O-(benzyl)-5-O-[bis(4-methoxyphenyl)(phenyl)methyl]-3-O-[(2-cyanoethoxy)(dipropan-2-ylamino)phosphanyl]-b-D-arabinofuranosyl}-6-[2-(trimethylsilyl)ethoxy]-9H-purine;

9-{2-O-(4-(pyridine-4-yl)benzyl)-5-O-[bis(4-methoxyphenyl)(phenyl)methyl]-3-O-[(2-cyanoethoxy)(dipropan-2-ylamino)phosphanyl]-b-D-ribofuranosyl}-6-[2-(trimethylsilyl)ethoxy]-9H-purine;

9-{2-O-[4-(3-methyl-1,2,4-oxadiazol-5-yl)benzyl]-5-O-[bis(4-methoxyphenyl)(phenyl)methyl]-3-O-[(2-cyanoethoxy)(dipropan-2-ylamino)phosphanyl]-b-D-ribofuranosyl}-6-[2-(trimethylsilyl)ethoxy]-9H-purine;

9-{2-O-[4-(1,3-oxazol-2-yl)benzyl]-5-O-[bis(4-methoxyphenyl)(phenyl)methyl]-3-O-[(2-cyanoethoxy)(dipropan-2-ylamino)phosphanyl]-b-D-ribofuranosyl}-6-[2-(trimethylsilyl)ethoxy]-9H-purine;

9-{2-O-[4-(1,3-thiazol-5-yl)benzyl]-5-O-[bis(4-methoxyphenyl)(phenyl)methyl]-3-O-[(2-cyanoethoxy)(dipropan-2-ylamino)phosphanyl]-b-D-ribofuranosyl}-6-[2-(trimethylsilyl)ethoxy]-9H-purine;

9-{2-O-[4-(furan-2-yl)benzyl]-5-O-[bis(4-methoxyphenyl)(phenyl)methyl]-3-O-[(2-cyanoethoxy)(dipropan-2-ylamino)phosphanyl]-b-D-ribofuranosyl}-6-[2-(trimethylsilyl)ethoxy]-9H-purine;

9-{2-O-[4-(2-methoxypyridin-3-yl)benzyl]-5-O-[bis(4-methoxyphenyl)(phenyl)methyl]-3-O-[(2-cyanoethoxy)(dipropan-2-ylamino)phosphanyl]-b-D-ribofuranosyl}-6-[2-(trimethylsilyl)ethoxy]-9H-purine;

9-{2-O-[4-(2-methyl-pyrazol-4-yl)benzyl]-5-O-[bis(4-methoxyphenyl)(phenyl)methyl]-3-O-[(2-cyanoethoxy)(dipropan-2-ylamino)phosphanyl]-b-D-ribofuranosyl}-6-[2-(trimethylsilyl)ethoxy]-9H-purine;

9-{2-O-[4-(2-methylpyrrol-2-yl)benzyl]-5-O-[bis(4-methoxyphenyl)(phenyl)methyl]-3-O-[(2-cyanoethoxy)(dipropan-2-ylamino)phosphanyl]-b-D-ribofuranosyl}-6-[2-(trimethylsilyl)ethoxy]-9H-purine;

9-{2-O-[4-(2-(pyrrolidin-1-yl)pyrimidin-5-yl)benzyl]-5-O-[bis(4-methoxyphenyl)(phenyl)methyl]-3-O-[(2-cyanoethoxy)(dipropan-2-ylamino)phosphanyl]-b-D-ribofuranosyl}-6-[2-(trimethylsilyl)ethoxy]-9H-purine;

9-{2-O-[4-(2-methoxypyridin-5-yl)benzyl]-5-O-[bis(4-methoxyphenyl)(phenyl)methyl]-3-O-[(2-cyanoethoxy)(dipropan-2-ylamino)phosphanyl]-b-D-ribofuranosyl}-6-[2-(trimethylsilyl)ethoxy]-9H-purine;

9-{2-O-(2-bromobenzyl)-5-O-[bis(4-methoxyphenyl)(phenyl)methyl]-3-O-[(2-cyanoethoxy)(dipropan-2-ylamino)phosphanyl]-b-D-ribofuranosyl}-6-[2-(trimethylsilyl)ethoxy]-9H-purine;

9-{2-O-[2-(pyridin-4-yl)benzyl]-5-O-[bis(4-methoxyphenyl)(phenyl)methyl]-3-O-[(2-cyanoethoxy)(dipropan-2-ylamino)phosphanyl]-b-D-ribofuranosyl}-6-[2-(trimethylsilyl)ethoxy]-9H-purine;

N-acetyl-2'-O-benzyl-5'-O-[bis(4-methoxyphenyl)(phenyl)methyl]-3'-O-[(2-cyanoethoxy) (dipropan-2-ylamino)phosphanyl]adenosine;

2'-O-benzyl-5'-O-[bis(4-methoxyphenyl)(phenyl)methyl]-3'-O-[(2-cyanoethoxy)(dipropan-2-ylamino)phosphanyl]uridine;

2'-O-benzyl-5'-O-[bis(4-methoxyphenyl)(phenyl)methyl]-3'-O-[(2-cyanoethoxy)(dipropan-2-ylamino)phosphanyl]-N-(2-methylpropanoyl)-guanosine; and N-Acetyl-2'-O-benzyl-5'-O-[bis(4-methoxyphenyl)(phenyl)methyl]-3'-O-[(2-cyanoethoxy)(dipropan-2-ylamino)phosphanyl]-N-(2-methylpropanoyl)-cytidine;

or a pharmaceutically acceptable salt or stereoisomer thereof.

In another embodiment, the invention features a compound illustrated by the Formula B:

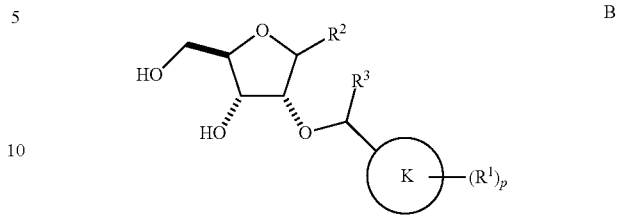

wherein,
p is 0, 1, 2 or 3;
Ring K is aryl, heterocyclyl or a $(C_3-C_8)$cycloalkyl;
$R^1$ is independently selected from: OH, COOH, $CF_3$, $NO_2$, halo, $(C_1-C_6)$alkyl, $O(C_1-C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1-C_6)$alkyl;
$R^2$ is selected from: a canonical or universal base; and
$R^3$ is selected from H and $(C_1-C_6)$alkyl;
or a pharmaceutically acceptable salt or stereoisomer thereof.

In another embodiment, the invention features a compound illustrated by the Formula B:

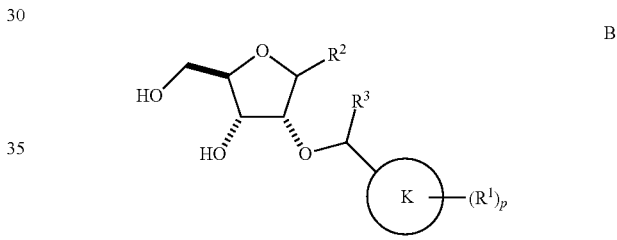

wherein,
p is 0, 1, 2 or 3;
Ring K is aryl, heterocyclyl or a $(C_3-C_8)$cycloalkyl with the proviso that when aryl is phenyl, then p is not 0;
$R^1$ is independently selected from: OH, COOH, $CF_3$, $NO_2$, halo, $(C_1-C_6)$alkyl, $O(C_1-C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1-C_6)$alkyl;
$R^2$ is selected from: a canonical or universal base; and
$R^3$ is selected from H and $(C_1-C_6)$alkyl;
or a pharmaceutically acceptable salt or stereoisomer thereof.

Specific compounds of the instant invention include:
1,4-Anhydro-2-O-benzyl-D-ribitol;
1,4-Anhydro-2-O-(4-tert-butylbenzyl)-D-ribitol;
1,4-Anhydro-2-O-(4-methylbenzyl)-D-ribitol;
1,4-Anhydro-2-O-(2-fluorobenzyl)-D-ribitol;
1,4-Anhydro-2-O-(4-fluorobenzyl)-D-ribitol;
1,4-Anhydro-2-O-(3-trifluoromethylbenzyl)-D-ribitol;
1,4-Anhydro-2-O-(4-trifluoromethylbenzyl)-D-ribitol;
1,4-Anhydro-2-O-(2-fluoro-4-trifluoromethylbenzyl)-D-ribitol;
1,4-Anhydro-2-O-(3,5-ditrifluoromethylbenzyl)-D-ribitol;
1,4-Anhydro-2-O-(2,6-difluoromethylbenzyl)-D-ribitol;
1,4-Anhydro-2-O-(2,4-difluoromethylbenzyl)-D-ribitol;
1,4-Anhydro-2-O-(2-difluoromethoxybenzyl)-D-ribitol;

1,4-Anhydro-2-O-(2-fluoro-4-chloromethylbenzyl)-D-ribitol;
1,4-Anhydro-2-O-(2-chloromethylbenzyl)-D-ribitol;
1,4-Anhydro-2-O-(3-chloro-5-trifluoromethoxybenzyl)-D-ribitol;
1,4-Anhydro-2-O-(4-methoxybenzyl)-D-ribitol;
1,4-Anhydro-2-O-(3-methoxybenzyl)-D-ribitol;
1,4-Anhydro-2-O-(2-methoxybenzyl)-D-ribitol;
1,4-Anhydro-2-O-(2-methylbenzyl)-D-ribitol;
1,4-Anhydro-2-O-(3,5-dimethylbenzyl)-D-ribitol;
1,4-Anhydro-2-O-(4-isopropylbenzyl)-D-ribitol;
1,4-Anhydro-2-O-(4-phenylbenzyl)-D-ribitol;
1,4-Anhydro-2-O-(2-naphthyl)-D-ribitol;
1,4-Anhydro-2-O-(3-nitrobenzyl)-D-ribitol;
1,4-Anhydro-2-O-[(4-tetrahydropyran-4-yl)benzyl]-D-ribitol;
1,4-Anhydro-2-O-[(5-methyl-1,2,4-oxadiazol-3-yl)benzyl]-D-ribitol;
1,4-Anhydro-2-O-[(5-methyl-1,3,4-oxadiazol-2-yl)benzyl]-D-ribitol;
1,4-Anhydro-2-O-benzyl]-D-arabinitol;
1,4-Anhydro-2-O-(2-methylbenzyl)-D-ribitol;
2'-O-benzylinosine;
2'-O-(2-methylbenzyl) inosine;
2'-O-(2-naphthyl) inosine;
2'-O-(2-difluoromethoxybenzyl) inosine;
2'-O-(3-methoxybenzyl) inosine;
2'-O-(pyridin-2-ylmethyl) inosine;
2'-O-(pyridin-3-ylmethyl) inosine;
2'-O-(pyridin-4-ylmethyl) inosine;
2'-O-(4-bromobenzyl) inosine;
9-(2-O-benzyl-b-D-arabinofuranosyl)-1,9-dihydro-6H-purin-6-one
2'-O-[(4-pyridin-4-yl)benzyl]inosine;
2'-O-[4-(5-methyl-1,3,4-oxadiazol-2-yl)benzyl]inosine;
2'-O-[4-(oxazol-2-yl)benzyl]inosine;
2'-O-[4-(thiazol-2-yl)benzyl]inosine;
2'-O-[4-(furan-2-yl)benzyl]inosine;
2'-O-[4-(2-methoxypyridin-3-yl)benzyl]inosine;
2'-O-[4-(2-methylpyrazol-4-yl)benzyl]inosine;
2'-O-[4-(1-methylpyrol-2-yl)benzyl]inosine;
2'-O-[4-(5-methyl-1,2,4-oxadiazol-3-yl)benzyl]inosine;
2'-O-{4-[2-(pyrrolidin-1-yl)pyrimidin-5-yl]benzyl}inosine;
2'-O-[4-(2-methoxypyridin-5-yl)benzyl)]inosine;
2'-O-[4-(3-fluoropyridin-5-yl)benzyl]inosine;
2'-O-(2-bromobenzyl) inosine;
2'-O-(pyridyn-4-ylmethyl) inosine;
2'-O-[2-(2-methoxypyridin-5-yl)benzyl]inosine;
N-acetyl-2'-O-benzyladenosine;
2'-O-benzyluridine;
2'-O-benzylguanosine; and
N-Acetyl-2'-O-benzylcytidine;
or a pharmaceutically acceptable salt or stereoisomer thereof.

In another embodiment, the invention features a siRNA which contains 1 or more 2'-sugar modification(s), wherein the 2'-sugar modification(s) are represented in Tables 1-3.

DEFINITIONS

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds.

Regarding the compounds of the instant invention, it is understood that the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples.

As used herein, "alkyl" is intended to include both branched and straight-chain saturated aliphatic hydrocarbon groups having the specified number of carbon atoms. For example, $C_1$-$C_6$, as in "($C_1$-$C_6$)alkyl" is defined to include groups having 1, 2, 3, 4, 5, or 6 carbons in a linear or branched arrange-ment. For example, "($C_1$-$C_6$)alkyl" specifically includes methyl, ethyl, n-propyl, i-propyl, n-butyl, t-butyl, i-butyl, pentyl, hexyl, and so on.

The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl. In cases where the aryl substituent is bicyclic and one ring is non-aromatic, it is understood that attachment is via the aromatic ring.

The term "heteroaryl", as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively. Such heteroaryl moieties for substituent Q include but are not limited to: 2-benzimidazolyl, 2-quinolinyl, 3-quinolinyl, 4-quinolinyl, 1-isoquinolinyl, 3-isoquinolinyl and 4-isoquinolinyl.

The term "heterocycle" or "heterocyclyl" as used herein is intended to mean a 3- to 10-membered aromatic or nonaromatic ring containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

As appreciated by those of skill in the art, "halo" or "halogen" as used herein is intended to include chloro (Cl), fluoro (F), bromo (Br) and iodo (I).

"siRNA oligomer" means a nucleic acid molecule capable of mediating RNAi (RNA interference). siRNA oligomers (or siRNAs) are well known in the art.

"Sugar un-modified universal base containing nucleoside(s)" means a nucleoside, wherein the canonical base (Adenine, Guanine, Cytosine or Uracil) is replaced with a universal base.

"Sugar modified universal base containing nucleoside(s)" means a nucleotide, wherein the canonical base (Adenine, Guanine, Cytosine or Uracil) is replaced with a universal base and the ribose is chemically modified.

"Universal base" means a group (typically a heterocycle) which is capable of isoenergetic interaction with a naturally occurring base (Loakes "Survey and summary: The application of universal DNA based analogues", *Nuc. Acids Res.*, 29(12), 2437-2447, 2001). Examples of universal bases include but are not limited to a hydrogen atom, inosine, modified adenine, modified guanine, modified uracil, modified cytosine, thymine, modified thymine, 2-aminoadenosine, 5-methylcytosine, 2,6-diaminopurine, or any base that can be complementary or non-complementary to target RNA or a non-nucleosidic base such as phenyl, naphthyl, 3-nitropyrrole, imidazole-4-carboxamide, 5-nitroindole, nebularine, pyridone, pyridinone, or any other non-naturally occurring universal base that can be complementary or non-complementary to target RNA.

"Canonical base" means adenine, guanine, uracil or cytosine.

"Position-specific data" means any data generated to establish siRNA oligomer function, wherein the siRNA oligomer contains 1 or more sugar modified or unmodified universal or canonical base containing nucleoside(s) at a specific position of the siRNA oligomer.

"Baseline data" means any data generated to establish siRNA oligomer function, wherein the siRNA oligomer contains 1 or more sugar un-modified universal base containing nucleoside(s).

"Position-specific knockdown data" means any knockdown data generated to establish siRNA oligomer function, wherein the siRNA oligomer contains 1 or more sugar modified or un-modified universal or canonical base containing nucleoside(s) at a specific position of the siRNA oligomer.

"Knockdown baseline data" means any knockdown data generated to establish siRNA oligomer function, wherein the siRNA oligomer contains 1 or more sugar un-modified or un-modified universal or canonical base containing nucleoside(s).

"Chemically modified siRNA" means an siRNA with chemical modifications that include phosphorothioate linkages, 2'-hydroxyl groups (including 2'-O-methyl, 2'-fluoro, 2'-O-(2-methoxyethyl and locked nucleic acid), base modifications, terminal nucleotide(s) modification and others.

In an embodiment, p is 0, 1 or 2.
In an embodiment, p is 0 or 1.
In an embodiment, p is 0.
In an embodiment, Ring K is aryl, heterocyclyl or a $(C_3-C_8)$cycloalkyl, with the proviso that Ring K is not phenyl.
In an embodiment, Ring K is phenyl, naphthyl or pyridyl.
In an embodiment Ring K is phenyl.
In an embodiment $R^1$ is OH, COOH, $CF_3$, $NO_2$, halo, $(C_1-C_6)$alkyl, $O(C_1-C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from $O(C_1-C_6)$alkyl, heterocyclyl, halo and $(C_1-C_6)$alkyl.
In an embodiment $R^1$ is OH, COOH, $CF_3$, $NO_2$, halo, $(C_1-C_6)$alkyl, $O(C_1-C_6)$alkyl, aryl, O-aryl, heteroaryl, O-heteroaryl, heterocyclyl or O-heterocyclyl, wherein said alkyl, aryl, heteroaryl and heterocyclyl is optionally substituted with from one to three substituents selected from halo and $(C_1-C_6)$alkyl.
In an embodiment $R^1$ is OH, COOH, $CF_3$, $NO_2$, halo, $(C_1-C_4)$alkyl, $O(C_1-C_6)$alkyl, phenyl, O-phenyl, O-pyranyl or oxadiazolyl, wherein said alkyl, phenyl, and oxadiazolyl is optionally substituted with from one to three substituents selected from halo and $(C_1-C_4)$alkyl.
In an embodiment $R^2$ is adenine, guanine, uracil or cytosine.
In an embodiment $R^2$ is a universal base.
In an embodiment $R^2$ is a hydrogen atom or inosine.
In an embodiment $R^3$ is selected from H and $CH_3$.
In an embodiment $R^3$ is H.
In an embodiment, the universal base is a hydrogen atom, or inosine.
In an embodiment, the ribose is chemically modified at the 2'-position.

Examples

Method

General Synthesis of Sugar-Modified Nucleoside Phosphoramidites.

The synthetic relay to access the modified anhydroribitol amidites, Intermediate 1, was prepared following the procedure depicted in Scheme 1.

Scheme 1

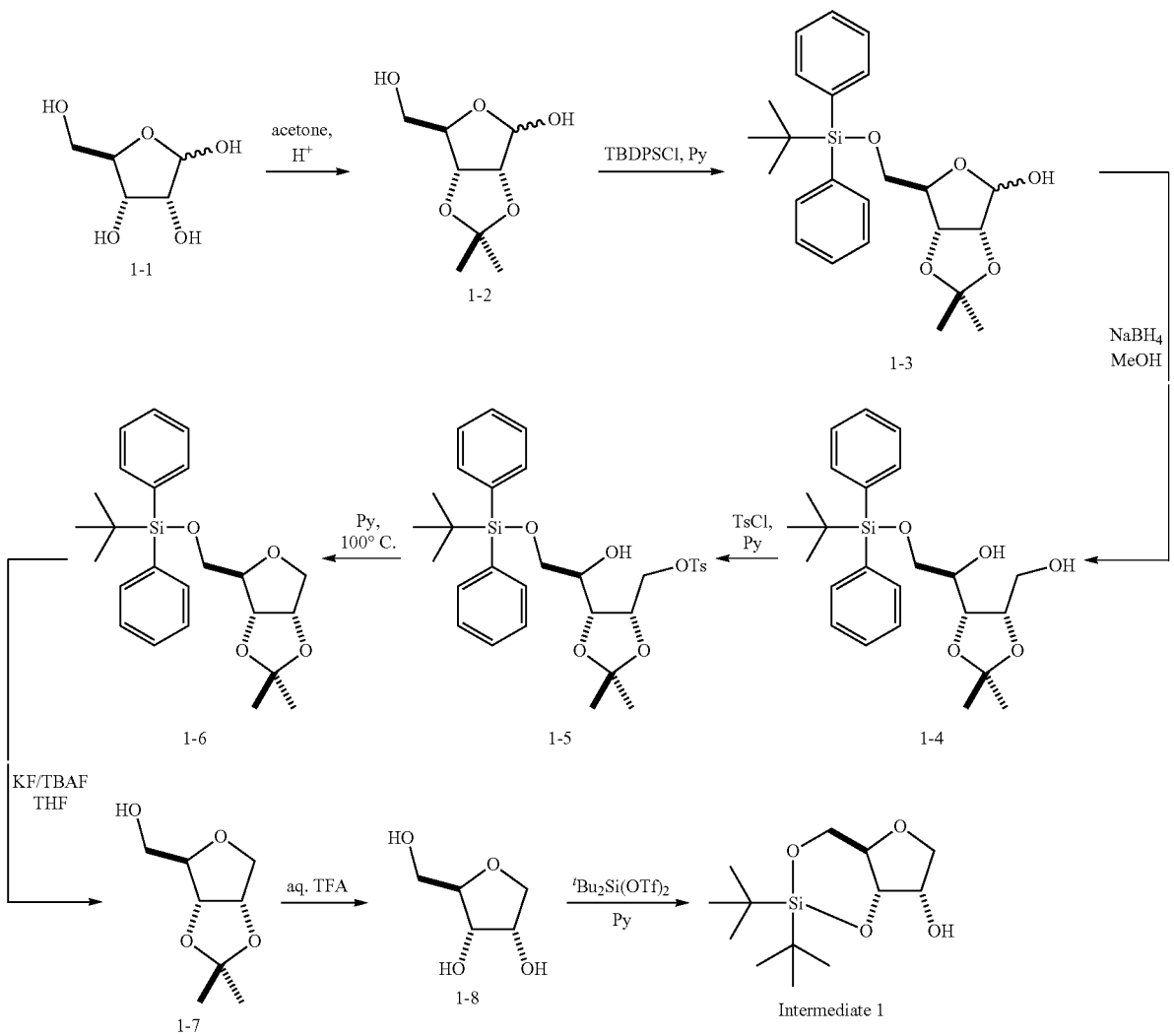

Commercial grade ribose (1-1) was converted to the respective 2',3'-O-acetonide 1-2 and the less hindered primary hydroxyl in 1-2 was protected as a tert-butyl-diphenylsilyl ether (1-3) following a previously described procedure (Choi, W. J. et al.: "Preparative and Stereoselective Synthesis of the Versatile Intermediate for Carbocyclic Nucleosides: "Effects of the Bulky Protecting Groups to Enforce Facial Selectivity", J. Org. Chem., 69, 2634-2636, 2004). Acetal 1-3 exists in equilibrium with the respective ring-open aldehyde and its exposure to sodium borohydride led to ring open diol 1-4. Monosilylation of this diol at the less hindered primary hydroxyl was achieved under standard conditions, and the ring-closure was affected at elevated temperature in the presence of a suitable base. The silyl-based protecting group present in 4-6 was removed using standard exposure to stoichiometric quantities of TBAF at ambient temperature, or at elevated temperature using excess potassium fluoride and TBAF catalysis. The penultimate intermediate 1-8 was obtained by careful treatment of alcohol 1-7 with 85% trifluoroacetic acid at 0 C and the synthesis was completed by selective protection of the 1,3-diol in 1-8 using the di-tert-butylsilylene protecting group (Greene, T. W., Wuts, P. G. M., "Protection of 1,2 and 1,3 diols", p. 237 in "Protective groups in organic synthesis", A Wiley Interscinece Publication, third edition, 1999).

Intermediate 2 was synthesized in a five step synthetic sequence as described in Scheme 2. According to this, inosine (2-1) was protected, as usual for 1,3-diols, with di-tert-butylsilylene protecting group (Araki, L. et al., "Synthesis of novel C4-linked C2-Imidazole Ribonucleotide and its Application in Probing the catalytic Mechanism of a Ribozyme", J. Org. Chem., 74, 2350-2356, 2009). To control the regioselectivity of the alkylation, the C6-carbonyl group was protected as a trimethylsilylethyl ether. This was achieved as follows: The secondary hydroxyl in 2-2 was temporarily protected as an acetyl ester (2-3) and the amide group within hypoxanthine was activated with 2,4,6-triisopropyl phenylsulfonyl chloride (compound 2-4). Reaction of 2-4 with trimethylsilyl ethanol in a presence of a base led to formation of 2-5. The acetate temporary protecting group present in 2-5 was removed using standard basic conditions.

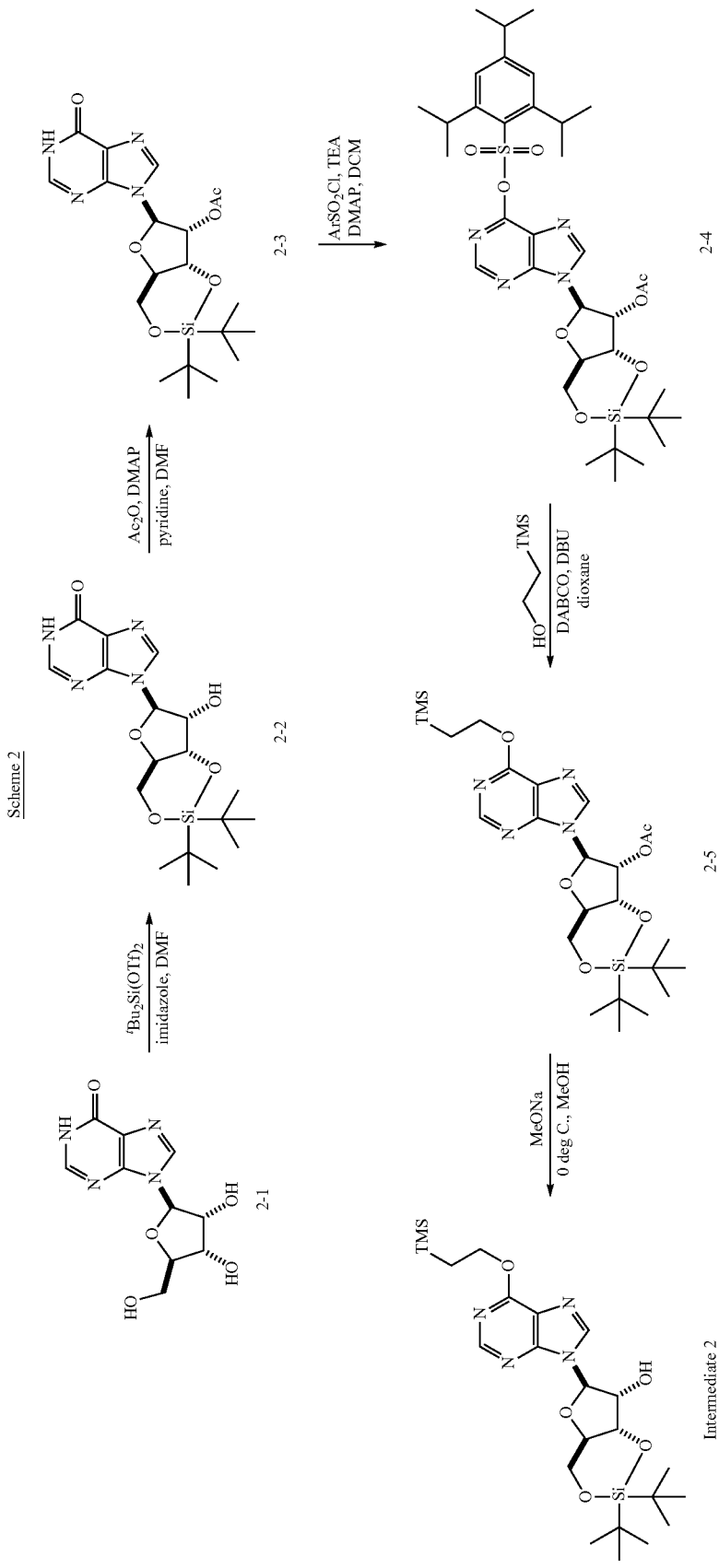

The 2'-O-benzyl modified anhydroribitol phosphoramidites were synthesized utilizing a four step synthetic sequence starting from Intermediate 1 as shown in Scheme 3.

Scheme 3

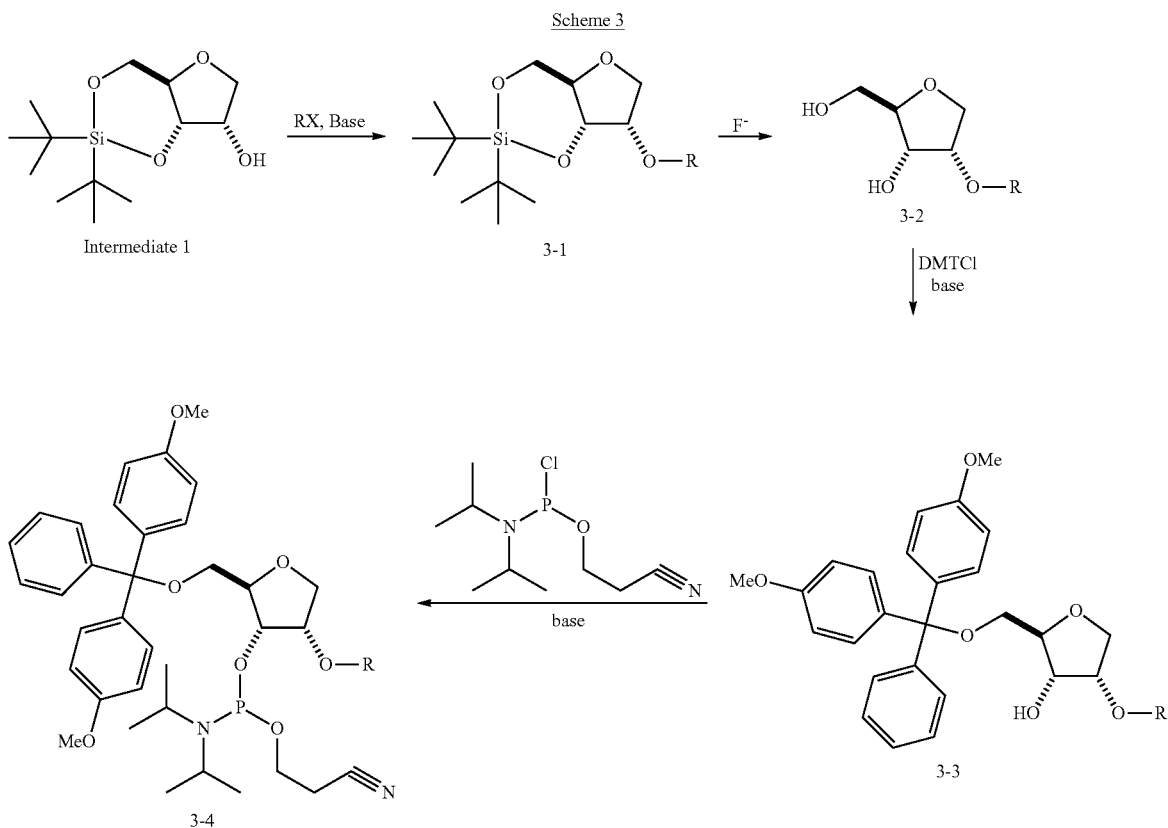

According to this, Intermediate 1 was alkylated with the appropriate benzyl bromide in the presence of a base to produce the derivative 3-1. The silyl protecting group was cleaved using tetrabutylammonium fluoride and the obtained polar diol 3-2 was purified using preparative HPLC utilizing a mass-spectrometric detector. The last two steps could also be performed without isolation of intermediate 3-1. The primary hydroxyl in diol 3-2 was then protected as a dimethoxytrityl ether by reacting 3-2 with dimethoxytrityl chloride at ambient temperature in a presence of a suitable base. The final phosphoamidites were then obtained by a reaction of the alcohol 3-3 with diisopropylamino-cyanoethoxyphosphorous chloride at ambient temperature and in the presence of a base.

A similar procedure was used to synthesize the appropriate 2'-O-modified inosine amidites, and the sequence is summarized in Scheme 4.

Scheme 4

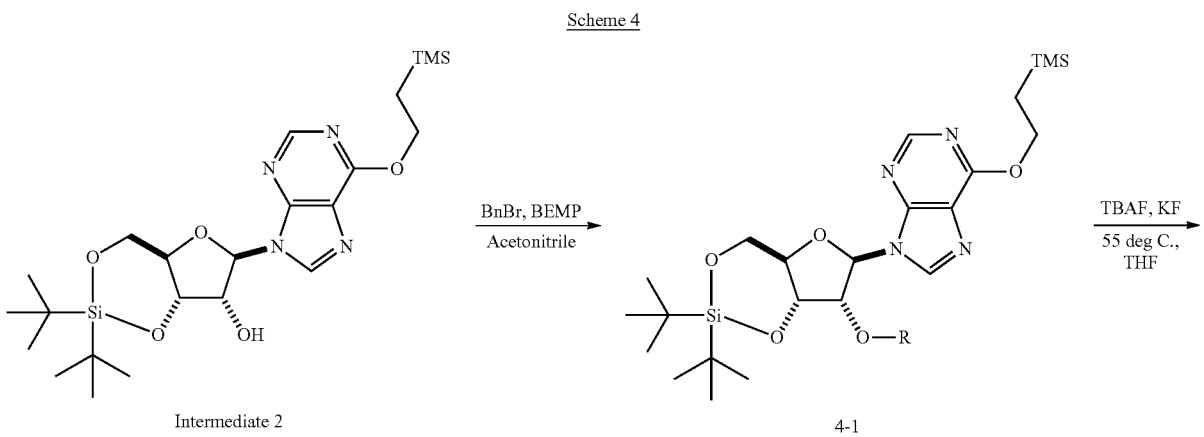

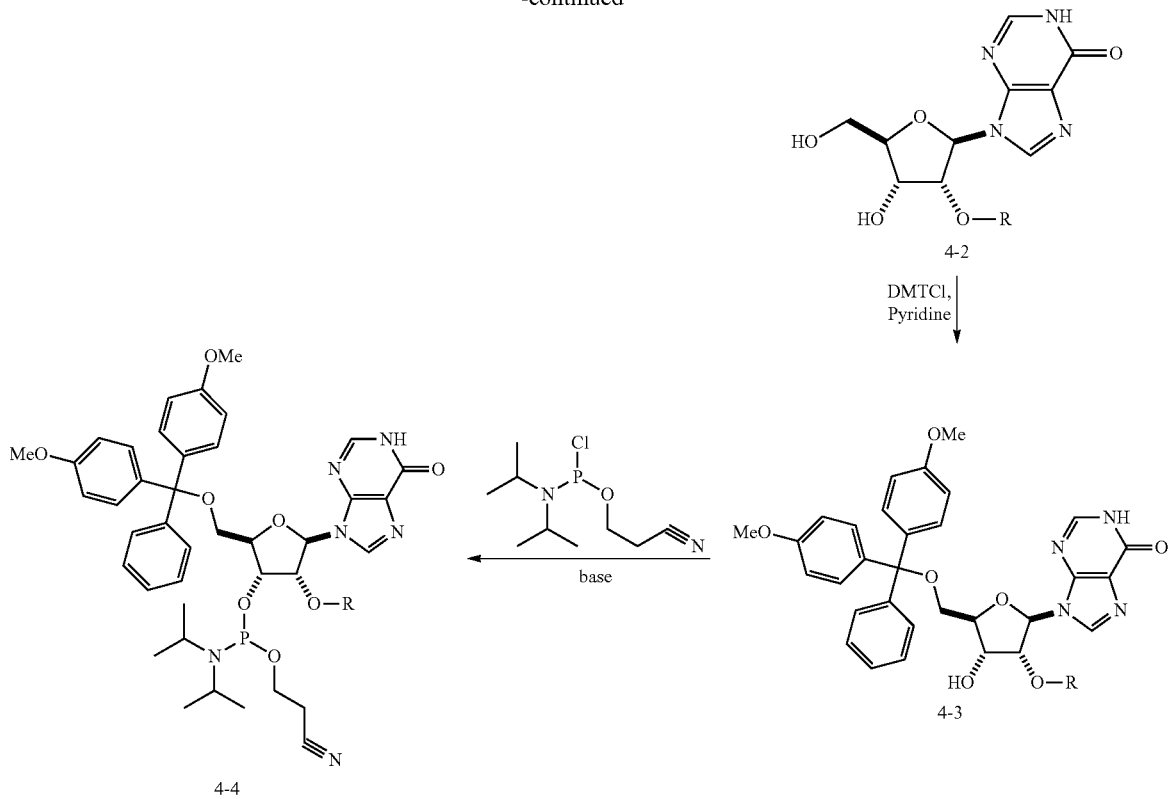

According to this, Intermediate 2 was alkylated with the appropriate benzyl bromide in a presence of a suitable base and the intermediate 4-1 was exposed to tetrabutylammonium fluoride at ambient temperature to affect simultaneous cleavage of both silyl-containing protecting groups. Alternatively, catalytic quantity of TBAF could be utilized if excess of KF was applied at elevated temperature. The diol 4-2 was then purified under usual conditions of column chromatography and the primary alcohol was protected as a dimethoxytrityl ether (4-3) as described above. The final amidites were then obtained by reacting intermediate 4-3 with diisopropylamino cyanoethoxyphosphorous chloride at ambient temperature and in the presence of an appropriate base. Final purifications were affected by column chromatography on triethylamine pretreated silica gel.

2'-O-benzyl substituted inosine amidites carrying a aromatic ring at the ortho- or para-positions could be readily accessed from downstream synthetic relays such as 5-3 through cross-coupling reactions, Scheme 5. According to this, intermediate 2 was alkylated with ortho- or para-bromobenzyl bromide as described above (Scheme 4), the cyclic silyl protecting group in 5-1 was then selectively removed using HF.Pyridine. The primary hydroxyl in 5-2 was protected as 4,4'-dimethoxytritylether (5-3) and these relays (general structure 5-3, para-bromobenzyl derivative, Intermediate 3 or, ortho-bromobenzyl derivative Intermediate 4), were further functionalized using aryl boron (Miyaura, Norio; Yamada, Kinji; Suzuki, Akira (1979) "A new stereospecific cross-coupling by the palladium-catalyzed reaction of 1-alkenylboranes with 1-alkenyl or 1-alkynyl halides". Tetrahedron Letters 20 (36): 3437-3440) or tin (Milstein, D.; Stille, J. K. J. Am. Chem. Soc. 1978, 100, 3636) based cross-coupling chemistry. The final amidites 5-5 were then synthesized as described above.

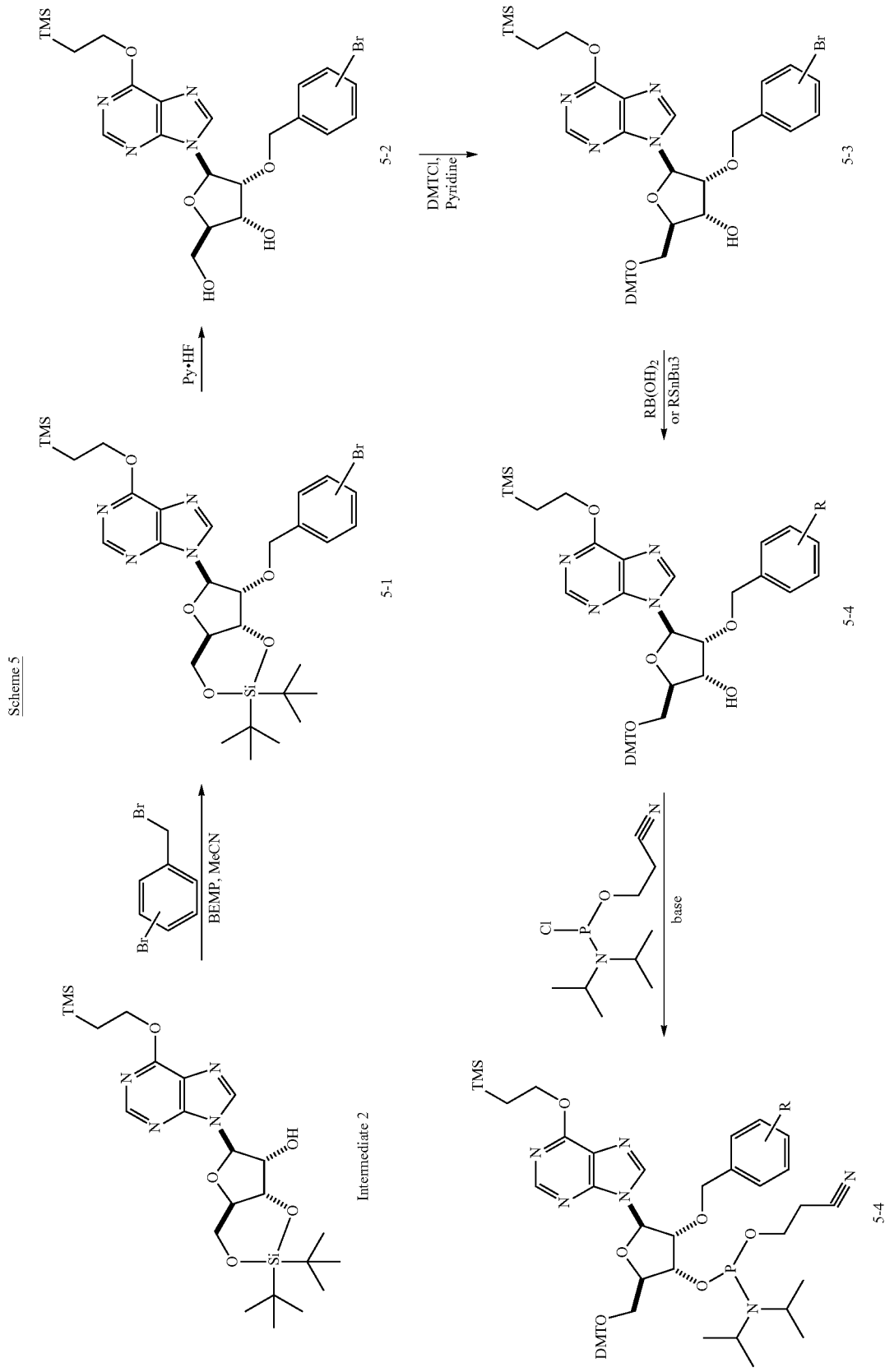

Scheme 6
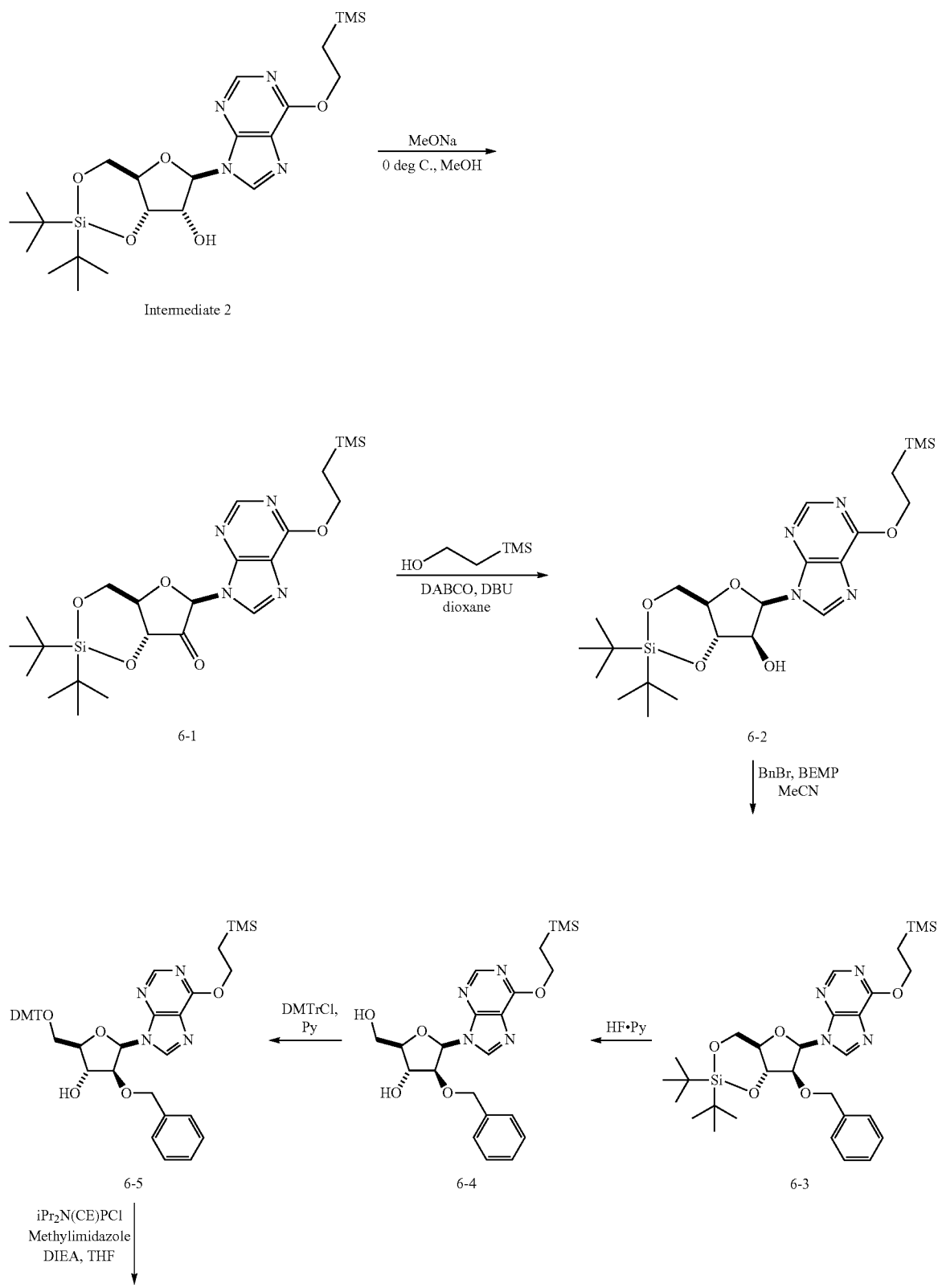

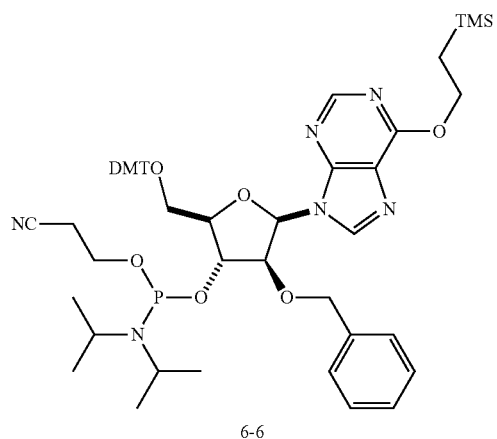
6-6
The 2'-O-substituted anhydroribitols, synthesis of which is depicted in Scheme 3, are summarized in Table 1, the 2'-O-substituted inosines, described in Scheme 4 and 5 are summarized in Table 2 and 3.
TABLE 1
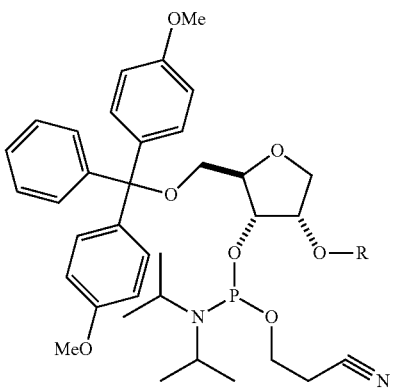
| Entry | Structure (R) | Empirical formula | Calculated | Found [M + H]+ |
|---|---|---|---|---|
| 1 | | $C_{42}H_{51}N_2O_7P$ | 726.3 | 727.4 |
| 2 | | $C_{46}H_{59}N_2O_7P$ | 782.4 | 783.2 |
| 3 | | $C_{43}H_{53}N_2O_7P$ | 740.4 | 741.5 |
| 4 | | $C_{42}H_{50}FN_2O_7P$ | 744.3 | 745.3 |

TABLE 1-continued
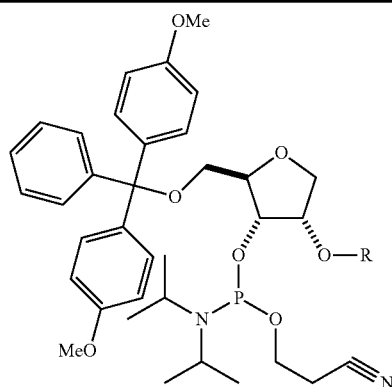
| Entry | Structure (R) | Empirical formula | Calculated | Found [M + H]⁺ |
|---|---|---|---|---|
| 5 | 3-F-C₆H₄-CH₂-O- | $C_{42}H_{50}FN_2O_7P$ | 740.4 | 745.3 |
| 6 | 4-F-C₆H₄-CH₂-O- | $C_{42}H_{50}FN_2O_7P$ | 740.4 | 745.3 |
| 7 | 3-F₃C-C₆H₄-CH₂-O- | $C_{43}H_{50}F_3N_2O_7$ | 794.3 | 795.2 |
| 8 | 4-F₃C-C₆H₄-CH₂-O- | $C_{43}H_{50}F_3N_2O_7$ | 794.3 | 795.3 |
| 9 | 4-F₃C-2-F-C₆H₃-CH₂-O- | $C_{43}H_{49}F_4N_2O_7$ | 812.3 | 813.3 |
| 10 | 3,5-F₂-C₆H₃-CH₂-O- | $C_{42}H_{49}F_2N_2O_7$ | 762.3 | 763.3 |
| 11 | 2,6-F₂-C₆H₃-CH₂-O- | $C_{42}H_{49}F_2N_2O_7$ | 762.3 | 763.3 |
| 12 | 2,4-F₂-C₆H₃-CH₂-O- | $C_{42}H_{49}F_2N_2O_7$ | 762.3 | 763.3 |

TABLE 1-continued
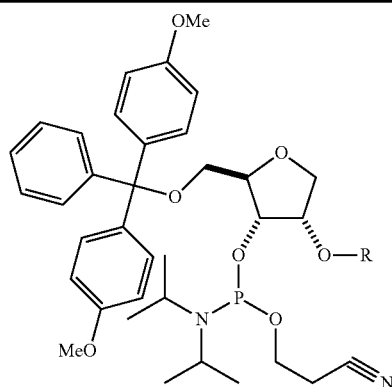
| Entry | Structure (R) | Empirical formula | Calculated | Found [M + H]+ |
|---|---|---|---|---|
| 13 | 2-(OCHF$_2$)-benzyl | C$_{43}$H$_{51}$F$_2$N$_2$O$_8$ | 792.3 | 793.4 |
| 14 | 4-Cl-2-F-benzyl | C$_{42}$H$_{49}$ClFN$_2$O$_7$P | 778.3 | 779.3 |
| 15 | 2-Cl-benzyl | C$_{42}$H$_{50}$ClN$_2$O$_7$P | 760.3 | 761.4 |
| 16 | 3-Cl-benzyl | C$_{42}$H$_{50}$ClN$_2$O$_7$P | 760.3 | 761.2 |
| 17 | 3-Cl-5-(OCF$_3$)-benzyl | C$_{43}$H$_{49}$ClF$_3$N$_2$O$_8$P | 844.3 | 845.2 |
| 18 | 4-MeO-benzyl | C$_{43}$H$_{53}$N$_2$O$_8$P | 756.4 | 757.4 |
| 19 | 3-MeO-benzyl | C$_{43}$H$_{53}$N$_2$O$_8$P | 756.4 | 757.4 |
| 20 | 2-MeO-benzyl | C$_{43}$H$_{53}$N$_2$O$_8$P | 756.4 | 757.3 |

TABLE 1-continued

| Entry | Structure (R) | Empirical formula | Calculated | Found [M + H]+ |
|---|---|---|---|---|
| 21 | 3-methylbenzyl | C₄₃H₅₃N₂O₇P | 740.4 | 741.4 |
| 22 | 3,5-dimethylbenzyl | C₄₄H₅₅N₂O₇P | 754.4 | 755.4 |
| 23 | 4-isopropylbenzyl | C₄₅H₅₇N₂O₇P | 768.4 | 769.4 |
| 24 | 4-biphenylmethyl | C₄₈H₅₅N₂O₇P | 802.4 | 803.4 |
| 25 | 2-naphthylmethyl | C₄₆H₅₃N₂O₇P | 776.4 | 777.3 |
| 26 | 3-nitrobenzyl | C₄₂H₅₀N₃O₉P | 771.3 | 772.2 |

TABLE 1-continued
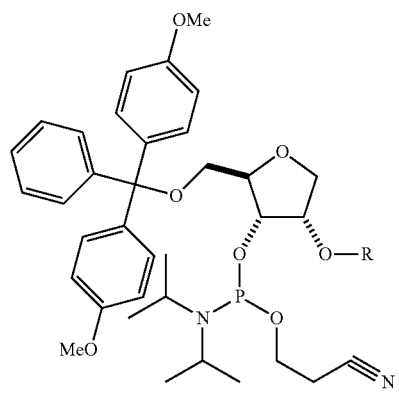
| Entry | Structure (R) | Empirical formula | Calculated | Found [M + H]+ |
|---|---|---|---|---|
| 27 | (tetrahydropyran-O-phenyl-CH2-O-) | $C_{47}H_{59}N_2O_8P$ | 826.4 | 827.3 |
| 28 | (3-methyl-1,2,4-oxadiazol-5-yl-phenyl-CH2-O-) | $C_{45}H_{53}N_4O_8P$ | 808.4 | 809.4 |
| 29 | (5-methyl-1,2,4-oxadiazol-3-yl-phenyl-CH2-O-) | $C_{45}H_{53}N_4O_8P$ | 808.4 | 809.5 |
| 30 | (benzyl-O-) | $C_{42}H_{51}N_2O_7P$ | 726.3 | 727.2 |
| 31 | (2-methylbenzyl-O-) | $C_{43}H_{53}N_2O_7P$ | 740.4 | 741.4 |

TABLE 2

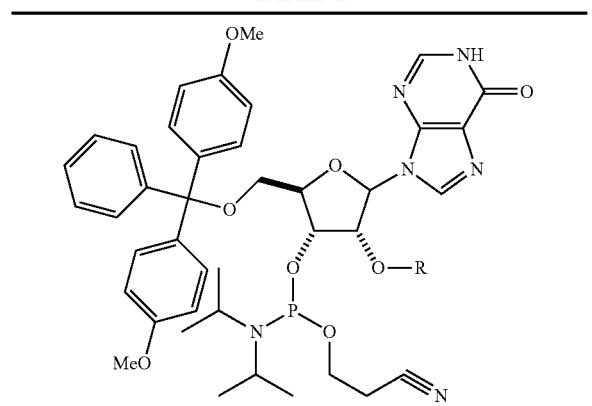

| Entry | Structure (R) | Empirical formula | Calculated | Found |
|---|---|---|---|---|
| 1 | benzyl-O- | $C_{47}H_{53}N_6O_8P$ | 860.43 | 861.3 |
| 2 | 2-methylbenzyl-O- | $C_{48}H_{55}N_6O_8P$ | 874.4 | 875.5 |
| 3 | 2-naphthylmethyl-O- | $C_{51}H_{55}N_6O_8P$ | 910.4 | 911.5 |
| 4 | 2-(OCHF$_2$)benzyl-O- | $C_{48}H_{53}F_2N_6O_9P$ | 926.4 | 927.4 |

TABLE 2-continued

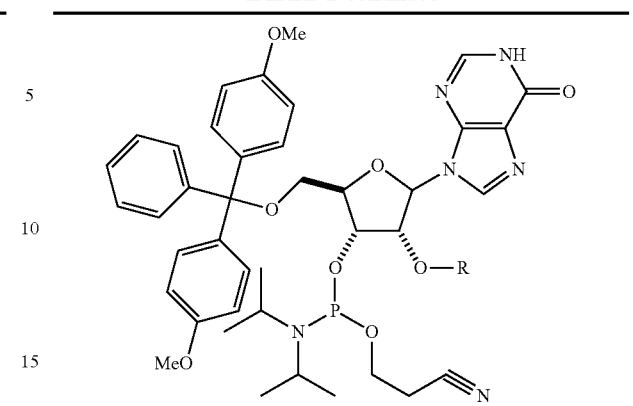

| Entry | Structure (R) | Empirical formula | Calculated | Found |
|---|---|---|---|---|
| 5 | 3-methoxybenzyl-O- | $C_{48}H_{55}ClN_6O_9P$ | 890.4 | 891.5 |
| 6 | 2-pyridylmethyl-O- | $C_{46}H_{52}N_7O_8P$ | 861.4 | 862.4 |
| 7 | 3-pyridylmethyl-O- | $C_{46}H_{52}N_7O_8P$ | 861.4 | 862.4 |
| 8 | 4-pyridylmethyl-O- | $C_{46}H_{52}N_7O_8P$ | 861.4 | 862.4 |

TABLE 3

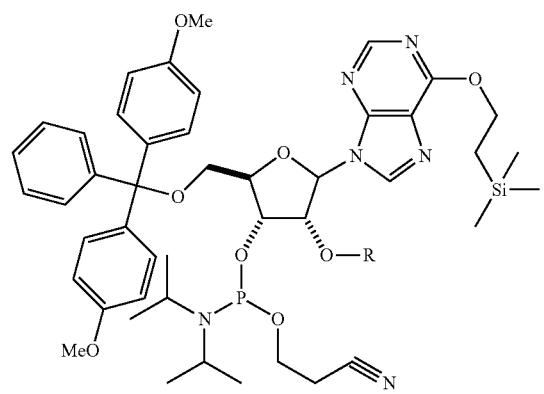

| Entry | Structure (R) | Empirical formula | Calculated | Found |
|---|---|---|---|---|
| 1 | 4-bromobenzyl-OMe | $C_{52}H_{64}BrN_6O_8PSi$ | 1038.3 | 1039.4 |

TABLE 3-continued

| Entry | Structure (R) | Empirical formula | Calculated | Found |
|---|---|---|---|---|
| 2 | benzyl-O- | $C_{52}H_{65}N_6O_8PSi$ | 961.1 | 961.6 |
| 3 | 4-(pyridin-4-yl)benzyl-O- | $C_{57}H_{68}N_4O_8PSi$ | 1037.5 | 1038.2 |
| 4 | 4-(3-methyl-1,2,4-oxadiazol-5-yl)benzyl-O- | $C_{55}H_{67}N_8O_9PSi$ | 1042.5 | 1043.5 |
| 5 | 4-(oxazol-2-yl)benzyl-O- | $C_{55}H_{66}N_7O_9PSi$ | 1027.4 | 1028.5 |
| 6 | 4-(thiazol-5-yl)benzyl-O- | $C_{55}H_{66}N_7O_8PSSi$ | 1043.4 | 1044.4 |
| 7 | 4-(furan-2-yl)benzyl-O- | $C_{56}H_{67}N_6O_9PSi$ | 1026.4 | 1027.5 |
| 8 | 4-(2-methoxypyridin-3-yl)benzyl-O- | $C_{58}H_{70}N_7O_9PSi$ | 1067.5 | 1068.5 |

TABLE 3-continued

| Entry | Structure (R) | Empirical formula | Calculated | Found |
|---|---|---|---|---|
| 9 | (1-methyl-pyrazol-4-yl)phenyl-CH2-O- | $C_{56}H_{69}N_8O_8PSi$ | 1040.5 | 1041.5 |
| 10 | (1-methyl-pyrrol-2-yl)phenyl-CH2-O- | $C_{57}H_{70}N_7O_8PSi$ | 1039.5 | 1040.5 |
| 11 | (5-methyl-1,2,4-oxadiazol-3-yl)phenyl-CH2-O- | $C_{55}H_{67}N_8O_9PSi$ | 1042.5 | 1043.5 |
| 12 | (2-pyrrolidin-1-yl-pyrimidin-5-yl)phenyl-CH2-O- | $C_{60}H_{74}N_9O_8PSi$ | 1107.5 | 1108.5 |
| 13 | (6-methoxy-pyridin-3-yl)phenyl-CH2-O- | $C_{58}H_{70}N_7O_9PSi$ | 1067.5 | 1068.5 |
| 14 | (5-fluoro-pyridin-3-yl)phenyl-CH2-O- | $C_{57}H_{67}FN_7O_8PSi$ | 1055.5 | 1056.5 |

TABLE 3-continued

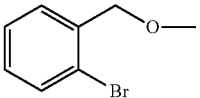

| Entry | Structure (R) | Empirical formula | Calculated | Found |
|---|---|---|---|---|
| 15 | 2-bromobenzyl ether | $C_{52}H_{64}BrN_6O_8PSi$ | 1038.3 | 1039.5 |
| 16 | 2-(pyridin-4-yl)benzyl ether | $C_{57}H_{68}N_4O_8PSi$ | 1037.5 | 1038.5 |

Solid-Phase Synthesis of Oligonucleotides.

Synthesis of oligonucleotides from natural or chemically modified nucleoside phosphoramidites (phosphoramidites) proceeds in a synthesis cycle where a series of 4 chemical steps is repeated, varying the nature of the phosphoramidite, to obtain the requisite oligonucleotide sequence. The synthesis is carried out on an automated synthesizer from the 3'- to 5'-end on a solid support, typically controlled pore glass (CPG) or polymer bead, where the first 3' protected nucleoside is attached to the support via a suitable linker, often comprising a succinyl linkage.

The first step in the synthesis cycle is removal of a 5'-hydroxyl dimethoxytrityl (DMT) protecting group by treatment with a suitable acid, such as trichloroacetic acid or dichloroacetic acid. Following deprotection, the second step is chain elongation by coupling with a suitably protected phosphoramidite in the presence of an activator, such as 5-Ethylthio-1H-Tetrazole. The third step in the synthesis cycle is oxidation of phosphorous using an oxidizer, such as iodine in pyridine. Finally, the fourth step is capping any remaining uncoupled 5'-hydroxyl groups with a suitable agent, such as acetic anhydride. This synthesis cycle is repeated; varying the nature of the phosphoramidite, until the desired chain length and composition has been prepared.

The protected oligonucleotide is then liberated from the solid phase support by treatment with a suitable base, such as methylamine in water, which can affect both the cleavage of the oligonucleotide chain from the solid support, as well as remove any exocyclic amine protecting groups. If the oligonucleotide contains any 2'-O-silyl protecting groups, these may be removed by treatment with a suitable reagent, such as triethylamine trihydrofluoride.

The crude 5'-DMT protected oligonucleotide is then purified on a suitable support, such as a C-18 resin, where deprotection by-products are removed by elution with aqueous solvents, short-chain capped oligonucleotides may be removed with buffer elution, and the final 5'-DMT protecting group is removed by treatment with an acid, such as trifluoroacetic acid. The purified oligonucleotide is then eluted using a suitable mixture of an organic solvent in water.

This process is repeated to prepare a suitably complimentary oligonucleotide strand.

The two complimentary strands are then mixed together in a 1:1 molar ratio to afford an siRNA duplex.

Biological Evaluation of siRNA Oligonucleotides and Results.

RNA oligomers were evaluated for their siRNA performance using the five sequences shown in Table 3.

TABLE 3

| Gene | Position in mRNA sequence | Guide strand sequence (5'-3') |
|---|---|---|
| ApoB | 9514 | AUUUCAGGAAUUGUUAAAG (SEQ. ID. NO.: 1) |
| ApoB | 10162 | UUCAGUGUGAUGACACUUG (SEQ. ID. NO.: 2) |
| PCSK9 | 1965 | AAUGCAUUGAGGGCCUUGC (SEQ. ID. NO.: 3) |
| PHD2 | 196 | AUCAAAUUUGGGUUCAAUG (SEQ. ID. NO.: 4) |
| PHD2 | 384 | UAGACGUCUUUGCUGACUG (SEQ. ID. NO.: 5) |

Positions 1-19 of both strands were ribonucleotides, and the overhangs at positions 20 and 21 contained 2'-deoxyribonucleotide thymidines. This unmodified siRNA was the template for systematic evaluation of modified siRNAs containing a single modification at every position along the guide strand.

First, we systematically examined the position-dependent effect of the sugar-unmodified universal base on gene knockdown. This was accomplished using the following "modification walkthrough". In order to examine this effect for the ApoB 9514 sequence, i.e. AUUUCAGGAAUUGUUAAAG (SEQ.ID.NO.: 1), we synthesized this RNA oligomer with its first nucleotide, adenosine (A), replaced with anhydroribitol, or inosine (X). Then, a second sequence, in which the second nucleoside (U) was replaced with anhydroribitol or inosine was synthesized, keeping all other nucleotides unchanged. Altogether nineteen sequences were synthesized where the universal base replaced all the natural nucleosides in that sequence. This "modification walkthrough" is depicted in Table 4.

TABLE 4

| Entry | Gene | Position in mRNA sequence | Guide strand sequence (5'-3') |
|---|---|---|---|
| unmodified | ApoB | 9514 | AUUUCAGGAAUUGUUAAAG |
| 1 | ApoB | 9514 | XUUUCAGGAAUUGUUAAAG |
| 2 | ApoB | 9514 | AXUUCAGGAAUUGUUAAAG |
| 3 | ApoB | 9514 | AUXUCAGGAAUUGUUAAAG |
| 4 | ApoB | 9514 | AUUXCAGGAAUUGUUAAAG |
| 5 | ApoB | 9514 | AUUUXAGGAAUUGUUAAAG |
| 6 | ApoB | 9514 | AUUUCXGGAAUUGUUAAAG |
| 7 | ApoB | 9514 | AUUUCAXGAAUUGUUAAAG |
| 8 | ApoB | 9514 | AUUUCAGXAAUUGUUAAAG |
| 9 | ApoB | 9514 | AUUUCAGGXAUUGUUAAAG |
| 10 | ApoB | 9514 | AUUUCAGGAXUUGUUAAAG |
| 11 | ApoB | 9514 | AUUUCAGGAAXUGUUAAAG |
| 12 | ApoB | 9514 | AUUUCAGGAAUXGUUAAAG |
| 13 | ApoB | 9514 | AUUUCAGGAAUUXUUAAAG |
| 14 | ApoB | 9514 | AUUUCAGGAAUUGXUAAAG |
| 15 | ApoB | 9514 | AUUUCAGGAAUUGUXAAAG |
| 16 | ApoB | 9514 | AUUUCAGGAAUUGUUXAAG |
| 17 | ApoB | 9514 | AUUUCAGGAAUUGUUAXAG |
| 18 | ApoB | 9514 | AUUUCAGGAAUUGUUAAXG |
| 19 | ApoB | 9514 | AUUUCAGGAAUUGUUAAAX |

(X represents a universal base, such as anhydroribitol, inosine or 5-nitroindole incorporated into AUUUCAGGAAUUGUUAAAG (SEQ. ID. NO.: 1))

Figure 1B:
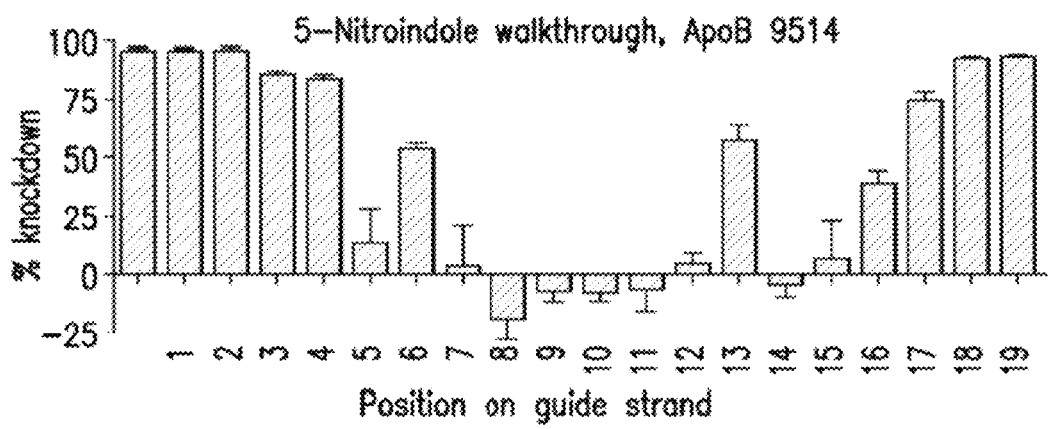
Figure 1C:
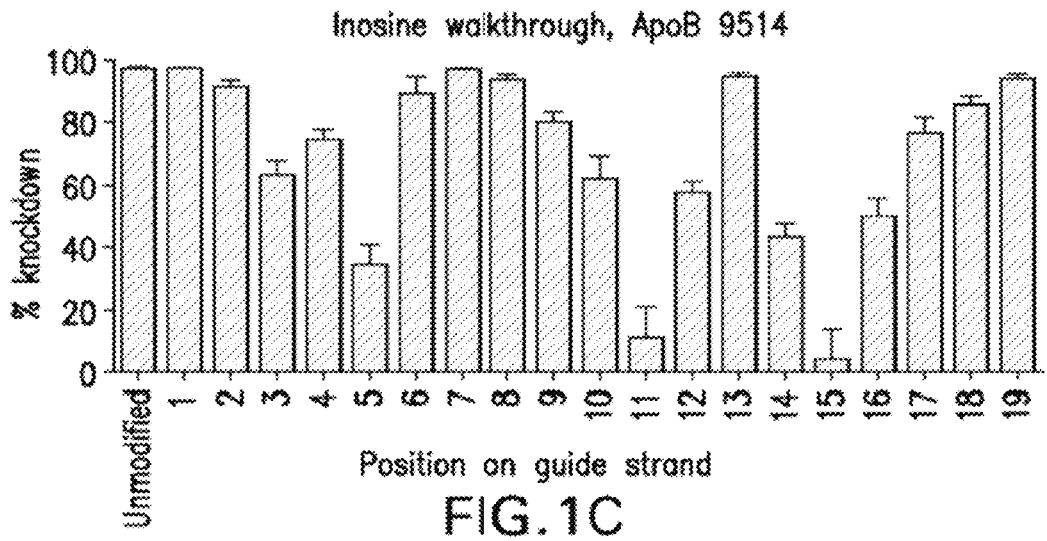

Similar evaluation of universal bases was performed using all five sequences shown in Table 3 and their mRNA degradation was established as follows: In a 96-well format, Hepa1-6 cells were transfected with either the unmodified, modified, or negative control siRNA using a commercial lipid transfection reagent. The target mRNA was assessed for degradation using standard Taqman procedures. The position-dependent mRNA degradation of the universal bases will be demonstrated using ApoB 9514, with the results summarized in FIGS. 1A, 1B and 1C.

In general, replacement of natural nucleosides with inosines or anhydroribitols resulted in target mRNA degradation. The two universal nucleosides which are not forming Watson-Crick base pairs showed reduced target mRNA degradation in the central region (positions 9 to 13). The activity was satisfactory when nucleosides at positions 14 through 19 were replaced with ones containing universal bases. Overall, the best performing universal nucleoside was found to be inosine, FIG. 1C.

Figure 2:
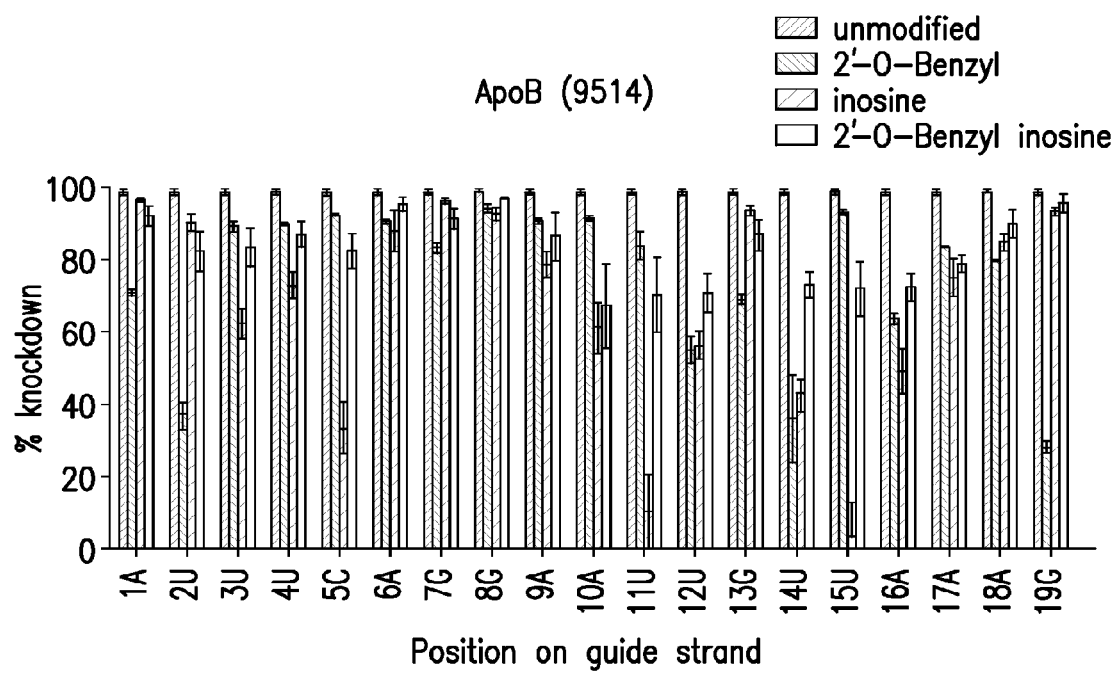
FIG. 2: Efficiency of position-dependent target mRNA degration 2'-O-benzyl substituted inosine containing siRNAs.

The mRNA degradation levels (e.g. those in FIG. 1C) observed with siRNAs where X is a universal base were used as baselines to assess modified inosines or modified anhydroribitols at the same positions. The usefulness of a particular nucleoside modification was evaluated by incorporation of a modified universal base containing nucleoside (X) into a RNA sequence such as depicted in Table 4. If the target mRNA degradation of the siRNA containing the modified universal nucleoside was better than that observed for the same siRNA containing the unmodified universal nucleoside at the same position, it was concluded that this modification is beneficial at that position. This is exemplified using 2'-O-benzyl modified inosines in FIG. 2.

The efficiency of a position-dependent target mRNA degration 2'-O-benzyl substituted inosine containing siRNAs (FIG. 2) suggests that a single 2'-O-benzyl substitution is well tolerated throughout the seed region, particularly at positions 4, 6, 7, 8 and 9. The target mRNA degradation data recorded for the 2'-O-benzyl-modified canonical bases confirm that this modification is well tolerated throughout the seed region, particularly at positions 6, 8 and 9, see FIG. 2.

Figure 3:
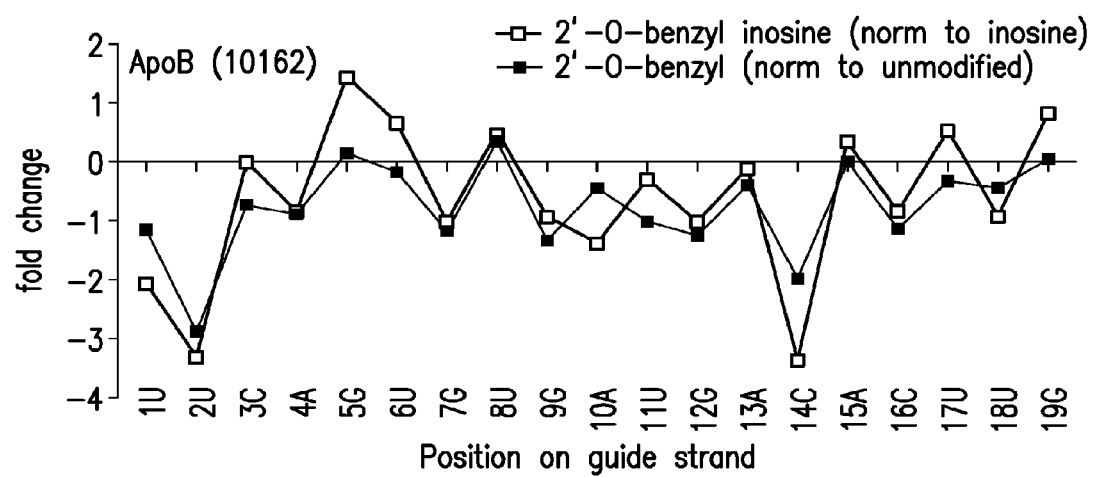
FIG. 3: Position-dependent relationship between the target mRNA degradation of siRNA (ApoB 10162) containing the 2-O-benzyl-substituted inosine and 2'-O-benzyl substituted canonical nucleoside at the same position.

The position-dependent relationship between the target mRNA degration of siRNA (ApoB 10162) containing the 2-O-benzyl-substituted inosine and 2'-O-benzyl substituted canonical nucleoside at the same position is demonstrated using a logarithmic representation of mRNA degradation (ddCt, Y-axis) FIG. 3. The modified inosine is normalized to the inosine at the same position. The 2'-O-benzyl modified nucleoside can be placed in an siRNA oligomer at positions 5, 6, 8, 14 and 19 and is well tolerated. A single 2'-O-benzyl substituted uridine at position 8 of the ApoB 10162 will result in slight improvement of the knockdown efficiency. Placing a 2'-O-benzyl-uridine at position 2, or a 2'-O-benzyl-cytidine at position 14 of this siRNA will have negative impact on knockdown efficiency.

Figure 4:
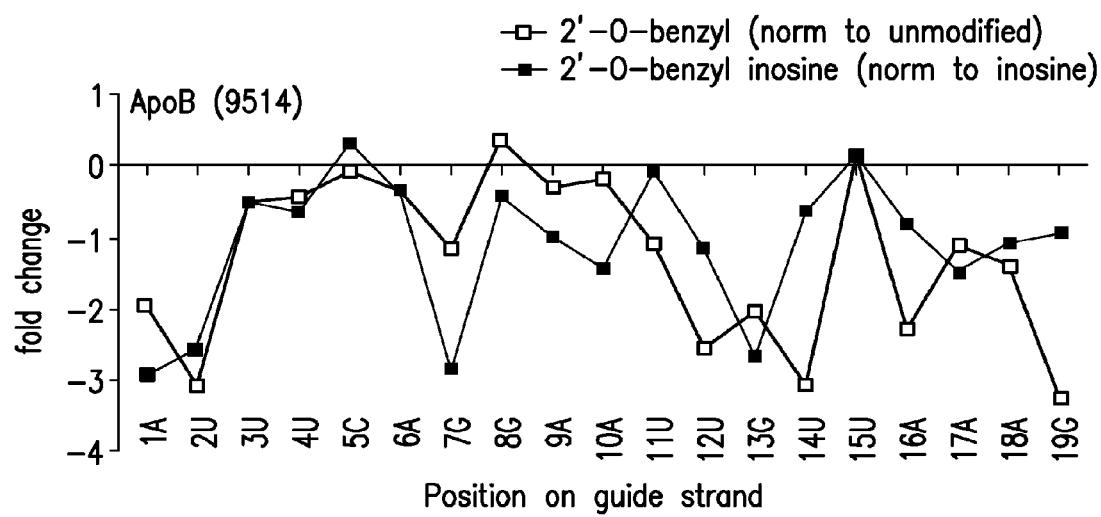
FIG. 4: Position-dependent relationship between the target mRNA degradation of siRNA (ApoB 9514) containing the 2-O-benzyl-substituted inosine and 2'-O-benzyl substituted canonical nucleoside at the same position.

Similar conclusions can be drawn comparing the behaviour of 2'-O-benzyl inosine to that of 2'-O-benzyl substituted canonical nucleoside in a different sequence targeting the same gene (ApoB 9514), FIG. 4. Placement of a 2'-O-benzyl substituted canonical nucleoside at position 5, 8 and 15 is well tolerated, while the same modification at position 2 and 14 is detrimental to performance.

Figure 5:
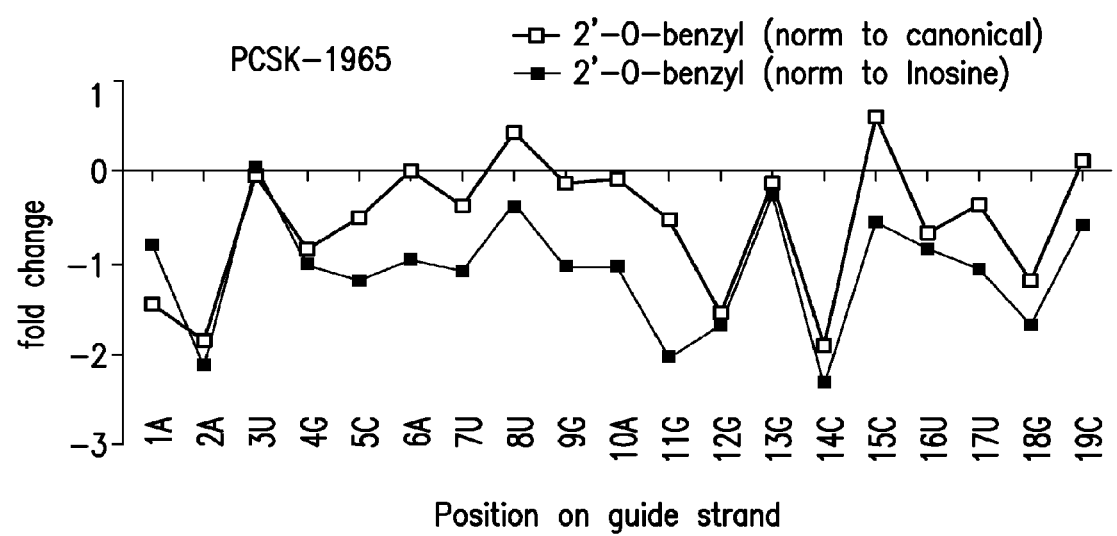
FIG. 5: Evaluation of the 2'-O-benzyl modification on the inosine platform.

Evaluating the 2'-O-benzyl modification on the inosine platform using the PCSK9 (1965) sequence suggests, that this particular modification will be well tolerated at positions 3, 6, 8, 13, 15 and 19, see FIG. 5. Indeed, placing 2'-O-benzyl modified nucleosides at positions 3, 6, 8, 13, 15 and 19 led to retention of silencing activity when compared to the unmodified sequence. In fact, as seen previously, 2'-O-benzyl substituents at positions 8 and 15 lead to slight improvements of activity.

Figure 6:
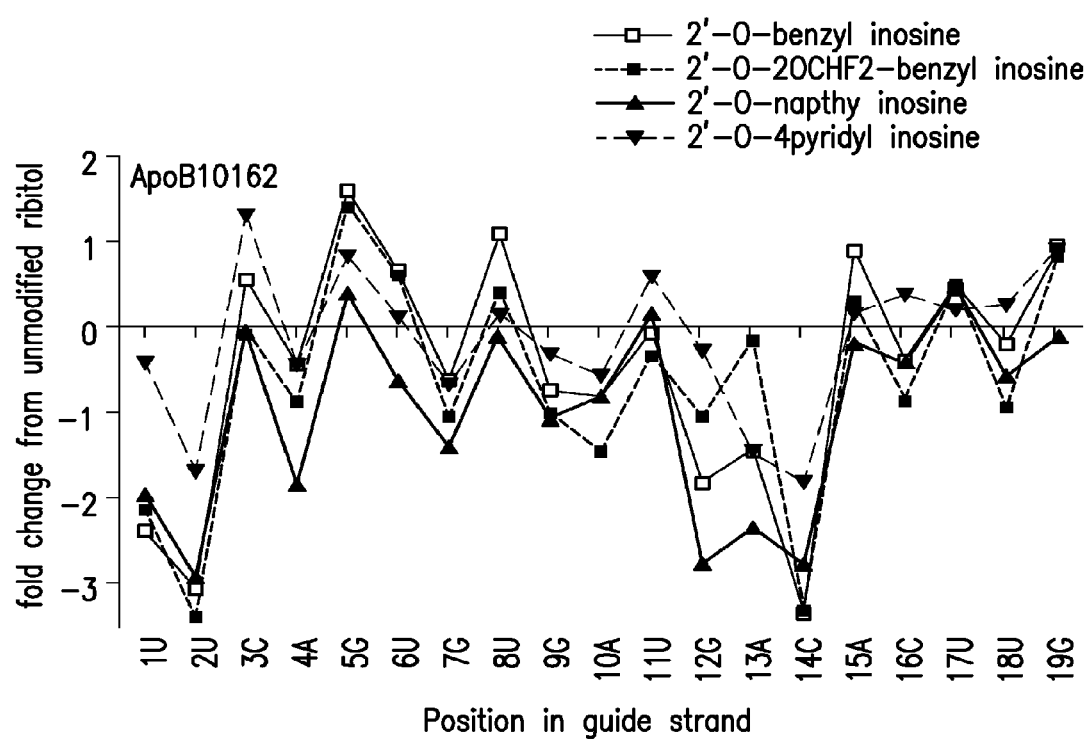
FIG. 6: Evaluation of the 2'-O-ribose modified nucleosides for their knockdown performance using the inosine platform.

The above data indicates that knockdown performance of a particularly modified inosine containing RNA oligomer can be used to assess the potential behaviour of the similarly modified full nucleoside. A number of 2'-O-ribose modified nucleosides were evaluated for their knockdown performance in the ApoB 10162 sequence using the inosine platform and the collected data are shown in FIG. 6. The included the 2'-O-methylene-(β-naphthyl), Entry 4, Table 2,2'-O-(2-difluoromethoxybenzyl), Entry 5, Table 2 and 2'-O-methylene-(4-pyridyl), Entry 9, Table 2.

Once again, the collected data suggest that the benzyl modified nucleosides can be tolerated within the seed region at positions 5 and 8, as well as position 15. In addition, the basic pyridine derivative (Entry 9, Table 2) appears to be tolerated at position 3.

Figure 7:
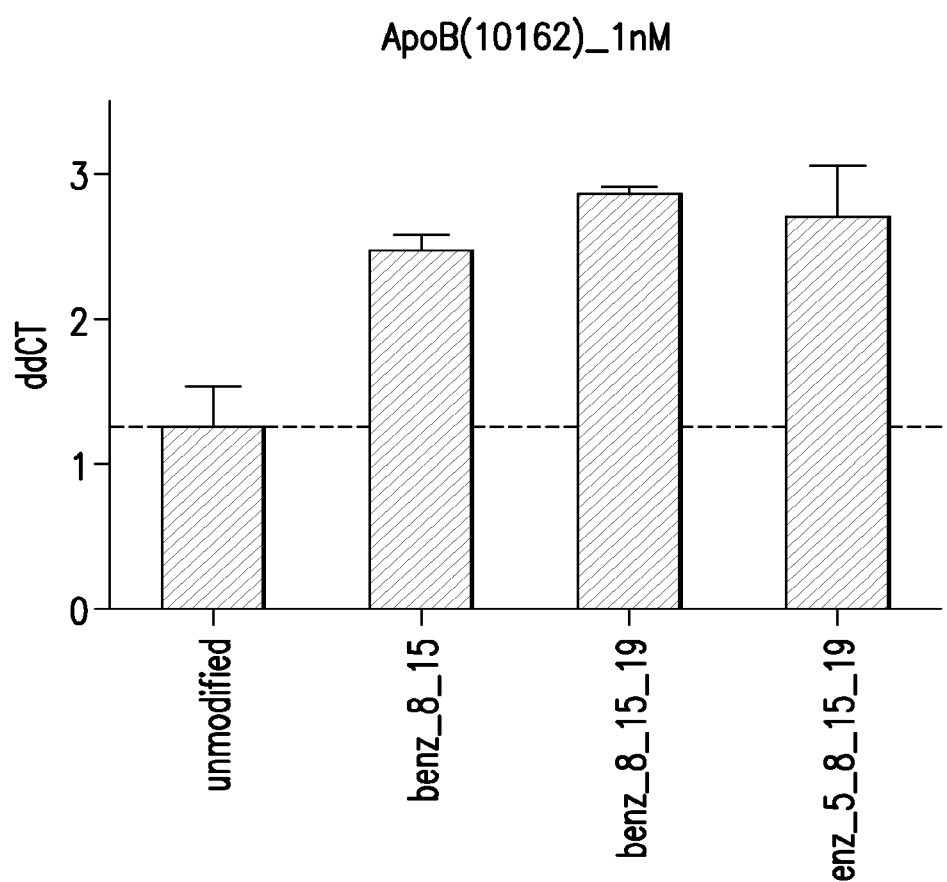
FIG. 7: Evaluation of an ApoB sequence with 2'-O-benzyl modification at positions 8 and 15; 8, 15, 19; and 5, 8, 15, 19.

Placement of a 2'-O-benzyl substituted canonical nucleoside at position 5, 8, 15, or 19 is well tolerated. Combinations of these positions were evaluated for mRNA degration activity. FIG. 7 shows an ApoB sequence with 2'-O-benzyl in combination at positions 8 and 15; 8, 15, 19; and 5, 8, 15, 19. There is a 4-fold increased in activity over the same sequence containing ribose at those same positions at 1 nM, indicating combinations of these modifications lead to improvement in activity.

Figure 8:
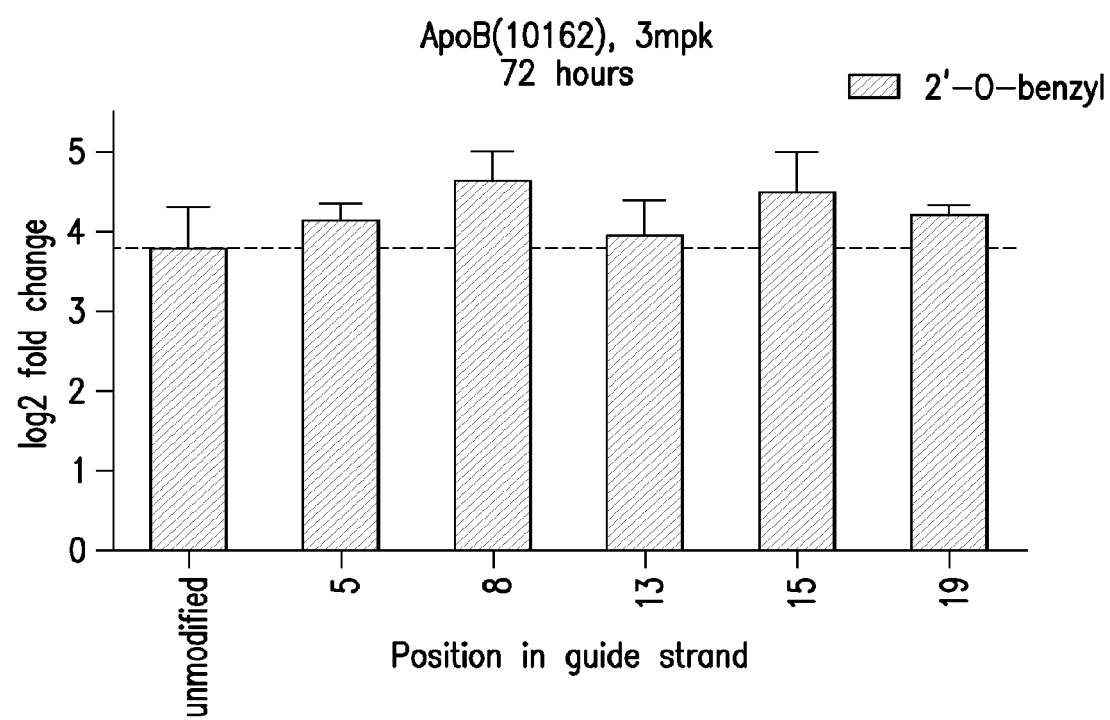
FIG. 8: Evaluation of an ApoB sequence with 2'-O-benzyl modification at positions 5, 8, 13, 15 or 19.

ApoB siRNAs corresponding to unmodified or modified with 2'-O-benzyl at positions 5, 8, 13, 15 or 19 were formulated into lipid nanoparticles and delivered by intravenous (i.v.) tail injection into mice (FIG. 8). 2'-O-Benzyl at positions 5, 13, 15, or 19 had similar activity to unmodified in vivo. Position 8 containing a 2'-O-Benzyl had a statistically significant increase in its ability to induce mRNA degradation from unmodified. The collected data suggest that the benzyl modified nucleosides can be tolerated within an siRNA and improve mRNA degradation in vivo.

Assays

Transfection and qPCR: Hepa1-6 cells were cultured in Dubellco's Modified Eagle Medium (Mediatech Cellgro) containing 10% serum. Cells were plated in a 96-well plate (3,500 cells/well) and were transfected twenty-four hours after plating in Opti-MEM I Reduced Serum Media (Gibco) and Lipofectamine RNAiMax reagent (Invitrogen) for a final concentration of 10 nM siRNA for the initial screening. For IC50 curves the final concentration ranged from 0.15 pM to 160 nM along a 12 point titration curve. Approximately twenty-four hours after transfection, cells were washed with phosphate buffered saline and lysed in Cells-to-CT Lysis Buffer (Ambion) with rDNase I (RNase-Free) added. Stop Solution (Ambion) was used to halt the reaction. RT-PCR was performed using 7 uL of cell lysate in 2× RT Buffer with 20× RT Enzyme Mix (Ambion) added. Conditions were as follows: 37° C. for 60 minutes and 95° C. for 5 minutes. ApoB mRNA levels were detected by quantitative PCR with ApoB specific probes from Applied Biosystems. All cDNA samples were added to a 10 uL reaction volume with the following cycling conditions: 2 minutes at 50° C., 10 minutes at 95° C., followed by 40 cycles of 15 seconds at 95° C. and 1 minute at 60° C. qPCR was assayed using an ABI Prism 7900 sequence detector using 2× Taqman Gene Expression Master Mix (Applied Biosystems). GAPDH mRNA levels were used for data normalization.

C57BL/6 male mice 20-23 g were purchased from Taconic Farms, Inc. After receiving, the mice rested for a week; were divided in groups of four and injected intravenously with 200 μl containing 3 mg/kg siRNA formulated in lipid nanoparticles (Pei, Y et al, RNA, 16, 2010). Mice were sacrificed at 72 hours following siRNA injection. Livers were harvested and processed to assess ApoB mRNA levels by qPCR as described above.

Examples

Compounds

All non-hydrolytic reactions, unless indicated otherwise were carried out in dry solvents purchased from Aldrich. HPLC analyses, except for the amidites, were performed at 60 C using an Agilent Zorbax Eclipse Plus C18, 2.1×50 mm, 1.8 micron column, at 0.8 mL/min flow rate, eluted with a gradient (5 to 95%) of acetonitrile and water with formic acid (0.1%) as a modifier. The amidites were analyzed using a Supelco Ascentis C18, 100×4.6 mm, 2.7 micron column and ammonium formate (3 mM) as a modifier, under otherwise identical conditions. UV traces were recorded at 220 nm and mass spectra were obtained using an Agilent Technologies 6140 Quadrupole LC/MS mass spectrometer in both positive and negative ion mode. NMR spectra were recorded on a Varian Unity 600, 500, or 400 spectrometers.

Intermediate 1

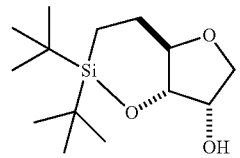 [SMILES: CC(C)(C)[Si]1(C(C)(C)C)CC[C@H]2OC[C@H](O)[C@@H]2O1]

Step A

5-O-[tert-Butyl(diphenyl) silyl)-2,3-O-(1-methylethylidene)-D-glycero-pentofuranose

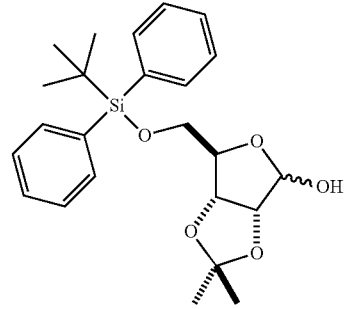

A solution of 2,3-O-(1-methylethylidene)-D-glycero-pentofuranose (40 g, 210 mmol), preparation of which is described in Choi, W. J. et al.: "Preparative and Stereoselective Synthesis of the Versatile Intermediate for Carbocyclic Nucleosides: "Effects of the Bulky Protecting Groups to Enforce Facial Selectivity", J. Org. Chem., 69, 2634-2636, 2004, and dimethylaminopyridine (0.20 g, 1.637 mmol) in pyridine (300 mL) was treated dropwise with tert-butyldiphenylsilyl-chloride (54 mL, 57.8 g, 210 mmol) and the resulting solution was stirred at ambient temperature overnight. The solvent was removed in vacuo, and the residue was distributed between water (500 mL) and DCM (500 mL). The organic layer was washed with water, dried with anhydrous magnesium sulfate, filtered and evaporated to dryness. The oily residue (91.5 g) was purified by gradient flash column chromatography using a mixture of hexanes and ethyl acetate to obtain 58.9 g (137 mmol, 65%) of the pure product. LCMS: for $C_{24}H_{31}O_4Si$ calculated 411.2. found 411.2 [M+H-H$_2$O]$^+$ and 427.2 [M-H]$^-$. $^1$H NMR (600 MHz, CD$_3$CN) δ: 7.70 (m, 4H), 7.45 (m, 6H), 5.20 (d, J=5.9

Hz, 1H), 4.75 (d, J=5.9 Hz, 1H), 4.48 (d, J=5.9 Hz, 1H), 4.35 (d, J=5.9 Hz, 1H), 4.15 (ddd, (J=10.1, 4.8, 4.0 Hz, 1H), 3.67 (m, 2H), 1.40 (s, 3H), 1.27 (s, 3H), 1.04 (s, 9H). $^{13}$C NMR (600 MHz, CD$_3$CN) δ: 135.74, 135.67, 130.34, 130.29, 128.17, 128.15, 117.54, 102.81, 86.74, 86.52, 82.30, 65.47, 26.47, 26.03, 24.30.

Step B

5-O-[tert-Butyl(diphenyl)silyl]-2,3-O-(1-methylethylidene)-D-ribitol

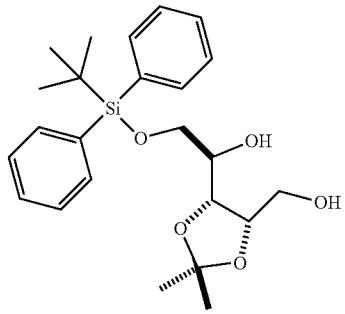

To a cooled solution (0° C.) of 5-O-[tert-butyl(diphenyl)silyl]-2,3-O-(1-methylethylidene)-D-glycero-pentofuranose (17 g, 39.7 mmol), preparation of which was described in the previous step, in methanol (200 mL) was added NaBH$_4$ (1.65 g, 43.6 mmol). The reaction mixture was kept stirring at 0° C. for 30 min before it warmed up to ambient temperature. Concentrated acetic acid was added dropwise to adjust pH to 7.0. The solvent was removed in vacuo, and the residue was dissolved in DCM (200 mL). The solution was washed with sat. NaHCO$_3$ (300 mL) and water (3×500 mL). The organic layer was dried with anhydrous sodium sulfate, filtered and evaporated to dryness. The residue was purified by flash chromatography using 30% ethyl acetate in hexane to obtain 17 g (39.5 mmol, 100%) of the pure product. LCMS: for C$_{24}$H$_{34}$O$_5$Si calculated 430.2. found 453.1 [M+Na]$^+$. $^1$H NMR (600 MHz, CD$_3$CN) δ: 7.71 (m, 4H), 7.44 (m, 6H), 4.22 (m, 2H), 3.76 (m, 6H), 3.58 (ddd, J=11.8, 6.7, 5.3 Hz, 1H), 3.29 (dd, J=6.8, 5.3 Hz, 1H), 1.27 (s, 6H), 1.03 (s, 9H). $^{13}$C NMR (600 MHz, CD$_3$CN) δ: 135.75, 135.71, 130.06, 130.05, 128.00, 127.96, 117.52, 77.86, 76.25, 70.09, 66.11, 60.73, 27.41, 26.40, 24.86.

Step C 1,4-Anhydro-5-O-[tert-Butyl(diphenyl)silyl]-2,3-O-(1-methylethylidene)-D-ribitol

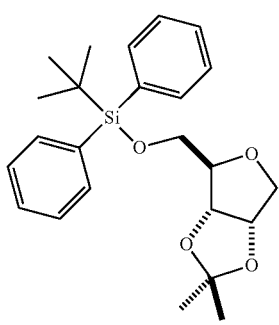

A mixture of 5-O-[tert-butyl(diphenyl)silyl]-2,3-O-(1-methylethylidene)-D-ribitol (17 g, 39.5 mmol) and p-toluenesulfonyl chloride (9.03 g, 47.4 mmol) in pyridine (100 mL) was heated at 100° C. for 16 h. After cooling to ambient temperature, the solvent was removed in vacuo. The residue was dissolved in DCM (200 mL), washed successively with aqueous sat. NaHCO$_3$ (300 mL) and water (3×500 mL). The organic layer was dried with anhydrous sodium sulfate, filtered and evaporated to dryness. The residue was purified by flash chromatography using 5-10% ethyl acetate in hexane to obtain 13 g (31.5 mmol, 80%) of the pure product. LCMS: for C$_{24}$H$_{34}$O$_5$Si calculated 412.2. found 413.2 [M+H]$^+$. $^1$H NMR (600 MHz, CD$_3$CN) δ: 7.67 (m, 4H), 7.44 (m, 6H), 4.80 (dd, J=5.4, 4.5 Hz, 1H), 4.74 (dd, J=6.2, 0.7 Hz, 1H), 4.00 (t, J=4.1 Hz, 1H) 3.93 (dd, J=10.3, 4.2 Hz, 1H), 3.82 (d, J=10.2 Hz, 1H), 3.67 (t, J=4.3 Hz, 2H), 1.41 (s, 3H), 1.29 (s, 3H), 1.02 (s, 9H). $^{13}$C NMR (600 MHz, CD$_3$CN) δ: 135.71, 135.64, 130.19, 130.14, 128.09, 117.53, 85.18, 82.79, 81.64, 73.83, 64.73, 26.41, 26.14, 24.27.

Step D 1,4-Anhydro-2,3-O-(1-methylethylidene)-D-ribitol

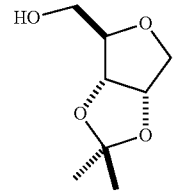

To a mixture of 1,4-anhydro-5-O-[tert-Butyl(diphenyl)silyl]-2,3-O-(1-methylethylidene)-D-ribitol (49 g, 119 mmol) and CsF (54.1 g, 356 mmol) in THF (200 mL) was added TBAF (1 M in THF, 17.81 mL, 17.81 mmol). The mixture was stirred at 70° C. for 16 h, cooled to ambient temperature, diluted with methanol (50 mL) and stirred for 10 min. The solvent was co-evaporated in vacuo with toluene (3×50 mL) and the residue was dissolved in DCM (60 mL). Purification by flash chromatography using 80-90% ethyl acetate in hexane gave 18.5 g (106 mmol, 89%) of the pure product. LCMS: for C$_8$H$_{14}$O$_4$ calculated 174.1. found 175.0 [M+H]$^+$. $^1$H NMR (600 MHz, CD$_3$CN) δ: 4.76 (ddd, J=5.9, 4.4, 1.4 Hz, 1H), 4.59 (dd, J=6.3, 1.1 Hz, 1H), 3.93 (dt, J=6.2, 1.0 Hz, 1H), 3.85 (m, 2H), 3.46 (m, 2H), 2.82 (s, 1H), 1.41 (s, 3H), 1.28 (s, 3H). $^{13}$C NMR (600 MHz, CD$_3$CN) δ: 117.54, 85.27, 82.48, 81.38, 72.29, 61.32, 26.11, 24.21.

Step E 1,4-Anhydro-D-ribitol

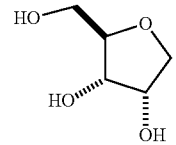

To a cold (0° C.) solution of TFA (44.2 mL, 574 mmol) and water (11 mL) was added 1,4-anhydro-2,3-O-(1-methylethylidene)-D-ribitol (10 g, 57.4 mmol) and stirred at ambient temperature for 2 h when TLC showed no starting material. Toluene (30 mL) was added and the volatiles were removed under reduced pressure while temperature was kept below 30° C. Co-evaporation with toluene was repeated two more times. The residue was purified by flash chromatography using 10-15% methanol in DCM to obtain 6.15 g (45.9 mmol, 80%) of the pure product. LCMS: for $C_5H_{10}O_4$ calculated 134.1. found 157.0 [M+Na]$^+$. $^1$H NMR (600 MHz, CD$_3$CN) δ: 4.07 (dd, J=8.7, 5.0 Hz, 1H), 3.93 (dd, J=9.6, 4.9 Hz, 1H), 3.89 (t, J=5.8 Hz, 1H), 3.60 (m, 3H), 3.47 (dd, J=12.6, 5.6 Hz, 1H), 3.41 (s, 1H). $^{13}$C NMR (600 MHz, CD$_3$CN) δ: 117.58, 83.17, 72.70, 72.03, 71.18, 62.27.

Step F 1,4-Anhydro-3,5-O-(di-tert-butylsilanylidene)-D-ribitol

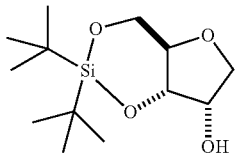

To a solution of 1,4-anhydro-D-ribitol (6.11 g, 45.6 mmol) in pyridine (40.5 mL, 501 mmol) at 0° C. was added dropwise di-tert-butylsilylbis(trifluoromethanesulfonate (22.07 g, 50.1 mmol) through an addition funnel with vigorous stifling over a period of 30 min. The mixture was slowly warmed to ambient temperature and continuously stirred for 1 h. The solvent was removed in vacuo, and the residue was partitioned between water (50 mL) and DCM (50 mL). The organic layer was dried with anhydrous sodium sulfate and concentrated. The residue was purified by flash chromatography using 10-30% ethyl acetate in hexane to obtain 10.4 g (37.9 mmol, 83%) of the pure product. LCMS: for $C_{13}H_{26}O_4Si$ calculated 274.2. found 275.1 [M+H]$^+$. $^1$H NMR (600 MHz, CD$_3$CN) δ: 4.30 (dd, J=7.8, 3.7 Hz, 1H), 4.22 (ddd, J=4.1, 4.1, 1.7 Hz, 1H), 4.10 (ddd, J=10.3, 4.3, 1.3 Hz, 1H), 3.82 (m, 3H), 3.69 (s, 1H), 3.02 (t, J=1.7 Hz 1H), 1.04 (s, 9H), 1.01 (s, 9H). $^{13}$C NMR (600 MHz, CD$_3$CN) δ: 117.54, 78.84, 74.48, 73.16, 69.81, 68.23, 27.05, 26.77, 26.31.

Intermediate 2

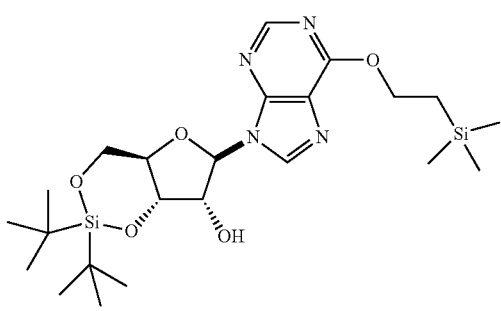 [SMILES: CC(C)(C)[Si]1(C(C)(C)C)OC[C@H]2O[C@@H](n3cnc4c(OCC[Si](C)(C)C)ncnc43)[C@H](O)[C@@H]2O1]

Step A

3',5'-O-(di-tert-butylsilanylidene)inosine

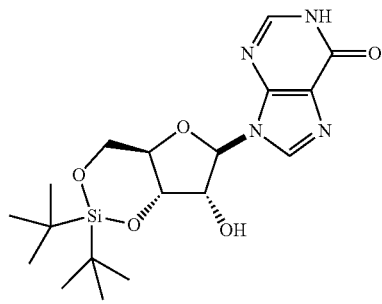 [SMILES: CC(C)(C)[Si]1(C(C)(C)C)OC[C@H]2O[C@@H](n3cnc4c(=O)[nH]cnc43)[C@H](O)[C@@H]2O1]

Under the protection of N$_2$, to a solution of inosine (40 g, 149 mmol) in anhydrous DMF (400 mL) at 0° C. was added dropwise di-tert-butylsilyl-bistriflate (53.1 mL, 164 mmol). After the above solution was stirred for 30 min at 0° C., imidazole (50 g, 746 mmol) was added and the reaction mixture was stirred at room temperature for 1 h. The solvents were removed under reduced pressure and the solid residue was triturated with dichloromethane and washed with H2O and collected. The 54 g (132 mmol, 89%) product was generated and applied in the next step without further purification. LCMS: for $C_{18}H_{28}N_4O_5Si$ calculated 408.1. found 409.1 [M+H]$^+$. $^1$H NMR (600 MHz, CD$_3$OD) δ: 8.14 (s, 1H), 8.02 (s, 1H), 5.97 (s, 1H), 4.66 (dd, J=9.3, 4.9 Hz, 1H), 4.57 (d, J=4.8 Hz, 1H), 4.41 (dd, J=8.9, 4.9 Hz, 1H), 4.15 (ddd, J=10.3, 10.3, 5.0 Hz, 1H), 4.06 (dd, J=9.4, 9.2 Hz, 1H), 1.096 (s, 9H), 1.055 (s, 9H). $^{13}$C NMR (600 MHz, CD$_3$OH) δ: 145.59, 139.77, 91.56, 76.41, 74.79, 73.99, 67.389, 26.75, 26.483.

Step B

2'-O-acetyl-3',5'-O-(di-tert-butylsilanylidene)inosine

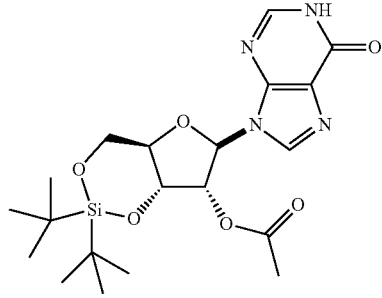 [SMILES: CC(=O)O[C@@H]1[C@@H]2O[Si](C(C)(C)C)(C(C)(C)C)OC[C@H]2O[C@H]1n1cnc2c(=O)[nH]cnc21]

Under the protection of N$_2$, Acetic anhydride was added drop-wise to a mixture of 3',5'-O-(di-tert-butylsilanylidene)inosine (5.3 g, 12.97 mmol), DMAP (0.317 g, 2.59 mmol), and anhydrous pyridine (25 mL, 309 mmol) in anhydrous DMF (50 mL) at 0° C. The mixture was stirred at 0° C. for 10 min subsequently under room temperature for 2 h. The reaction was quenched with methanol (40 mL) and evaporated to dryness. The solid residue was dissolved into EtOAc and washed three times with saturated sodium bicarbonate solution. Organic layer was dried over MgSO4 then evaporated to produce 5.6 g (12.87 mmol, 99%) pure compound. LCMS: for $C_{20}H_{30}N_4O_6Si$ calculated 450.2. found 451.0 [M+H]$^+$. $^1$H NMR (600 MHz, CD$_3$CN) δ: 7.90 (s, 1H), 7.90 (s, 1H), 6.03 (s, 1H), 5.63 (d, J=5.4 Hz, 1H), 4.81 (ddd, J=7.2, 5.4, 1.7 Hz, 1H), 4.40 (m, 1H), 4.06 (m, 2H), 2.12 (s, 3H) 1.075 (s, 9H), 1.021 (s, 9H). $^{13}$C NMR (600 MHz, CD$_3$CN) δ: 145.69, 139.07, 117.55, 88.46, 75.20, 74.874, 67.15, 26.90, 26.40, 26.63.

Step C

9-[2-O-acetyl-3,5-O-(di-tert-butylsilanylidene)-β-D-ribofuranosyl]-6-({[2,4,6-tri(propan-2-yl)phenyl]sulfonyl}oxy)-9H-purine

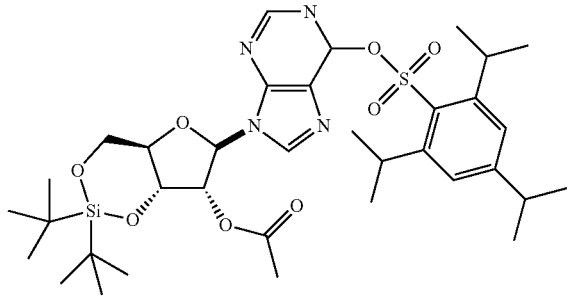 [SMILES: CC(=O)O[C@@H]1[C@@H]2O[Si](C(C)(C)C)(C(C)(C)C)OC[C@H]2O[C@H]1n1cnc2c1N=CNC2OS(=O)(=O)c1c(C(C)C)cc(C(C)C)cc1C(C)C]

Under the protection of N$_2$, to a solution of 2'-O-acetyl-3',5'-O-(di-tert-butylsilanylidene)inosine (5.6 g, 12.87 mmol) in 120 mL of anhydrous dichloromethane were added DMAP (0.315 g, 2.57 mmol), triethylamine (7.18 mL, 51.5 mmol) and 2,4,6-tri-isopropylbenzenesulfonyl chloride (11.7 g, 16 mmol,). After 2 h of stirring at room temperature the mixture was diluted with 100 mL of dichloromethane, washed three times with saturated sodium bicarbonate solution and one time with brine. The organic layers were combined, dried over MgSO$_4$ and evaporated to dryness. Resulting residue was purified by column chromatography (gradient: hexane with EtOAc 0-40%) and 3.97 g (5.54 mmol, 43%) pure compound obtained. LCMS: for C$_{35}$H$_{52}$N$_4$O$_8$SSi calculated 716.3. found 717.2 [M+H]$^+$. $^1$H NMR (600 MHz, CD$_3$CN) δ: 8.47 (s, 1H), 8.30 (s, 1H), 7.35 (s, 2H), 6.14 (s, 1H), 5.68 (d, J=5.2 Hz, 1H), 4.90 (ddd, J=7.2, 5.4, 1.7 Hz, 1H), 4.39 (m, 1H), 4.23 (m, 2H), 4.07 (m, 2H), 2.97 (m, 1H), 2.12 (s, 3H), 1.23 (m, 18H), 1.07 (s, 9H), 1.01 (s, 9H). $^{13}$C NMR (600 MHz, CD$_3$CN) δ: 169.56, 155.41, 154.73, 154.01, 151.30, 151.18, 145.17, 131.43, 124.56, 123.70, 117.56, 88.75, 75.33, 74.76, 74.69, 67.07, 34.25, 29.93, 26.92, 26.65, 23.83, 22.89, 22.38, 20.18, 20.08.

Step D

9-[2-O-acetyl-3,5-(di-tert-butylsilanylidene)-β-D-ribofuranosyl]-6-[2-(trimethylsilyl)ethoxy]-9H-purine

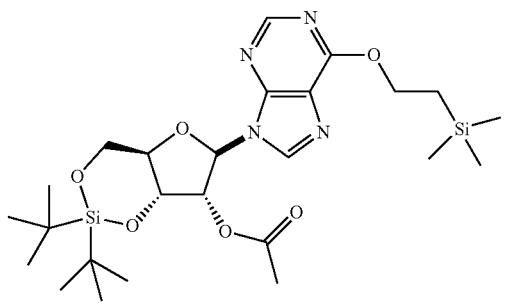 [SMILES: CC(=O)O[C@@H]1[C@@H]2O[Si](C(C)(C)C)(C(C)(C)C)OC[C@H]2O[C@H]1n1cnc2c(OCC[Si](C)(C)C)ncnc21]

Under the protection of N$_2$, to a solution of 9-[2-O-acetyl-3,5-O-(di-tert-butylsilanylidene)-β-D-ribofuranosyl]-6-({[2,4,6-tri(propan-2-yl)phenyl]sulfonyl}oxy)-9H purine (3.97 g, 5.54 mmol) in anhydrous dioxane (100 mL) were added DABCO (1.24 g, 11.07 mmol) and 8 g of dry 3 Å molecular sieves. After 30 min of stirring at room temperature 2-(trimethylsilyl)ethanol (3.97 mL, 27.7 mmol) and DBU (2.08 mL, 13.84 mmol) were added and the reaction was stirred at room temperature for 2 h. The mixture was then filtered off and the filtrate was evaporated to dryness. The residue was re-dissolved into 100 mL dichloromethane and washed with 100 mL saturated sodium bicarbonate solution. After NaHCO$_3$ layer was extracted with 100 mL dichloromethane three times, organic layers were combined, dried over MgSO$_4$ and evaporated to dryness. Resulting residue was purified by column chromatography (gradient: hexane with EtOAc 0-50%) and 2.8 g (5.08 mmol, 92%) pure compound obtained. LCMS: for C$_{25}$H$_{42}$N$_4$O$_6$Si$_2$ calculated 550.3. found 551.3 [M+H]$^+$. $^1$H NMR (600 MHz, CD$_3$CN) δ: 8.44 (s, 1H), 8.01 (s, 1H), 6.10 (s, 1H), 5.71 (d, J=5.2 Hz, 1H), 4.97 (dd, J=9.2, 5.3 Hz, 1H), 4.67 (m, 2H), 4.40 (dd, J=8.1, 4.0 Hz, 1H), 4.07 (m, 2H), 2.12 (s, 3H), 1.22 (m, 2H), 1.09 (s, 9H), 1.01 (s, 9H), 0.08 (s, 9H). $^{13}$C NMR (600 MHz, CD$_3$CN) δ: 169.677, 152.28, 141.98, 117.58, 88.54, 75.18, 74.86, 74.77, 67.18, 65.44, 58.84, 26.92, 26.71, 26.65, 22.40, 21.59, 20.20, 20.08, 17.21.

Step E

9-[3,5-O-(di-tert-butylsilanylidene)-β-D-ribofuranosyl]-6-[2-(trimethylsilyl)ethoxy]-9H-purine

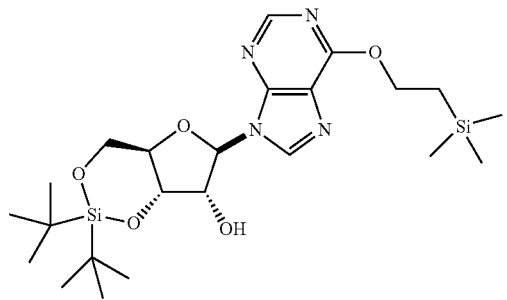 [SMILES: CC(C)(C)[Si]1(C(C)(C)C)OC[C@H]2O[C@@H](n3cnc4c(OCC[Si](C)(C)C)ncnc43)[C@H](O)[C@@H]2O1]

To a 0° C. 40 mL methanol solution of 9-[2-O-acetyl-3,5-O-(di-tert-butylsilanylidene)-β-D-ribofuranosyl]-6-[2-(trimethylsilyl)ethoxy]-9H-purine (2.6 g, 4.72 mmol), 0.5M sodium methoxide (28.3 ml, 14.16 mmol) in methanol was added drop-wise. After mixture was stirred at 0° C. for 10 min, reaction was quenched with addition of ammonium chloride (1.01 g, 18.88 mmol) and stirred at room temperature for 5 min. The mixture was filtered and the filtrate was evaporated. The residue was dissolved into 50 mL EtOAc and the organic layer was washed three times with 50 mL saturated sodium bicarbonate solution and one time with 50 mL H2O. Then after the organic layer was dried with MgSO4 and evaporated to produce the 1.70 g (3.34 mmol, 70.8%) product. LCMS: for C$_{23}$H$_{40}$N$_4$O$_5$Si$_2$ calculated 508.3. found 509.3 [M+H]$^+$. $^1$H NMR (600 MHz, CD$_3$OD) δ: 8.46 (s, 1H), 8.34 (s, 1H), 6.03 (s, 1H), 4.71 (m, 2H), 4.64 (d, J=4.8 Hz, 1H), 4.57 (s, 1H), 4.40 (dd, J=9.0, 5.0 Hz, 1H), 4.16 (ddd, J=10.0, 10.0, 5.1 Hz, 1H), 4.06 (dd, J=10.4, 9.2 Hz, 1H), 1.25 (m, 2H), 1.11 (s, 9H), 1.06 (s, 9H), 0.09 (s, 9H). $^{13}$C NMR (600 MHz, CD$_3$OD) δ: 152.24, 142.40, 91.68, 76.37, 74.79, 73.78, 67.41, 65.47, 26.77, 26.49, 17.24.

Intermediate 3

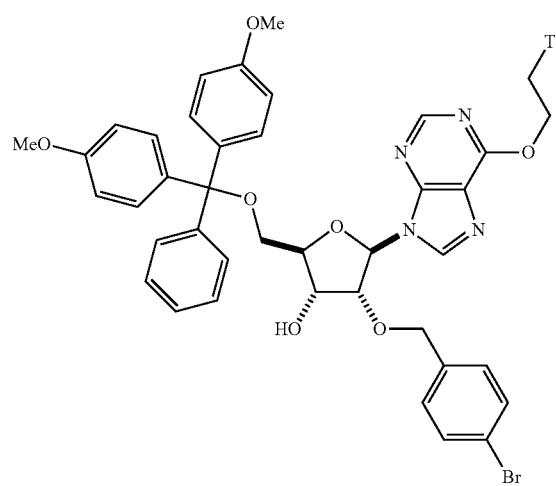

Step A

9-[2-O-(4-bromobenzyl)-3,5-o-(di-tert-butylsilanylidene)-β-D-ribofuranosyl]-6-[2-(trimethylsilyl)ethoxy]-9H-purine

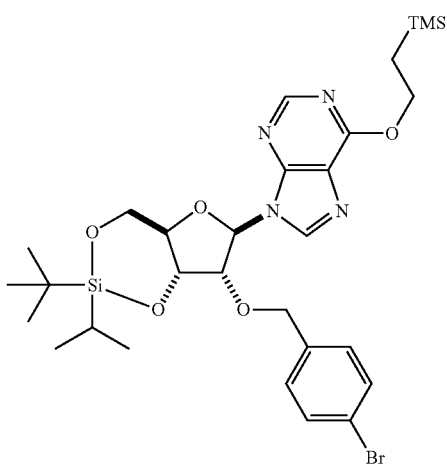

Under the protection of N$_2$, 9-[3,5-O-(di-tert-butylsilanylidene)-β-D-ribofuranosyl]-6-[2-(trimethylsilyl)ethoxy]-9H-purine (10.00 g, 19.66 mmol) was dissolved into 100 mL anhydrous acetonitrile with 3 Å molecular sieves (5 g). After the mixture was cooled to 0° C., 2-tert-butylimino-2-diethylamino-1,3-dimethylperhydro-1,3,2-diazaphosphorine (BEMP) (13.48 g, 49.1 mmol) followed immediately by 4-bromobenzyl bromide (14.74 mL, 59.00 mmol) were added with exclusion of moisture. The reaction was then warmed up gradually from 0° C. to room temperature and stirred at room temperature for 16 h. The mixture was quenched with methanol (15 mL) and the solvents were evaporated under the reduced pressure. The residue was purified with flash chromatography using 20% etheyl acetate in hexane to obtain 12.8 g (18.89 mmol, 96%) of the pure product. LCMS: for C$_{30}$H$_{45}$BrN$_4$O$_5$Si$_2$ calculated 677.8. found 679.3 [M+H]$^+$. $^1$H NMR (600 MHz, CD$_3$CN) δ: 8.47 (s, 1H), 8.09 (s, 1H), 7.51 (d, J=8.5 Hz, 2H), 7.35 (d, J=8.3 Hz, 2H), 6.14 (s, 1H), 4.96 (d, J=12.3, 1H), 4.77 (m, 2H), 4.69 (m, 2H), 4.47 (d, J=4.9 Hz, 1H), 4.43 (dd, J=9.1, 5.0 Hz, 1H), 4.21 (ddd, J=10.3, 10.3, 5.0 Hz, 1H), 4.08 (dd, J=10.2, 9.4 Hz, 1H), 1.23 (m, 2H), 1.12 (s, 9H), 1.04 (s, 9H), 0.10 (s, 9H). $^{13}$C NMR (600 MHz, CD$_3$CN) δ: 152.15, 141.39, 131.48, 129.56, 117.59, 89.67, 80.75, 76.83, 74.94, 71.81, 67.39, 65.39, 26.98, 26.70, 17.21, −2.14.

Step B

9-[2-O-(4-bromobenzyl)-β-D-ribofuranosyl]-6-[2-(trimethylsilyl)ethoxy]-9H-purine

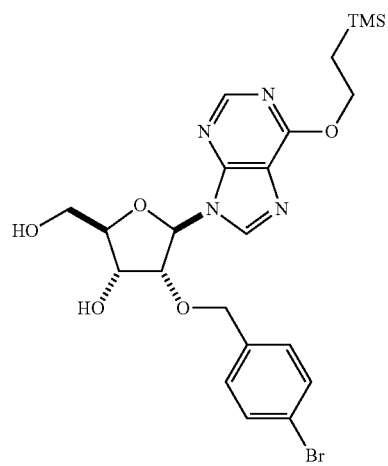

Hydrogen fluoride-pyridine (7.43 g, 75.0 mmol) was carefully diluted with pyridine (30.3 mL, 375 mmol) and then added drop wise to a solution of 9-[2-O-(4-bromobenzyl)-3,5-o-(di-tert-butylsilanylidene)-β-D-ribofuranosyl]-6-[2-(trimethylsilyl)ethoxy]-9H-purine (7.43 g, 74.97 mmol) in THF (100 mL) at 0° C. The mixture was slowly warmed up to room temperature and stirred for 2 h. The reaction was quenched with methanol (10 mL) and then evaporated to dryness. The residue was purified by flash chromatography using 90% ethyl acetate in hexanes to obtain 8.8 g (16.37 mmol, 87%) of the pure product. LCMS: for C$_{22}$H$_{29}$BrN$_4$O$_5$Si calculated 537.5. found 539.1 [M+H]$^+$. $^1$H NMR (600 MHz, CD$_3$CN) δ: 8.30 (s, 1H), 8.09 (s, 1H), 7.15 (m, 2H), 6.93 (d, J=8.2 Hz, 2H), 5.93 (d, J=7.3 Hz, 1H), 5.27 (dd, J=10.5, 2.9 Hz, 1H), 4.72 (m, 2H), 4.64 (m, 2H), 4.45 (s, 1H), 4.34 (d, J=12.6 Hz, 1H), 4.18 (d, J=1.6 Hz, 1H), 3.78 (dt, J=12.7, 2.5 Hz, 1H), 3.68 (ddd, J=12.6, 10.4, 2.2 Hz, 1H), 3.56 (d, J=3.0 Hz, 1H), 1.28 (m, 2H), 0.12 (s, 9H). $^{13}$C NMR (600 MHz, CD$_3$CN) δ: 151.36, 142.65, 136.94, 131.07, 129.97, 121.25, 117.68, 117.50, 88.34, 87.92, 79.34, 71.24, 69.97, 65.70, 62.69, 17.26, −2.12.

Step C

9-{5-O-[bis(4-methoxyphenyl)(phenyl)methyl]-2-o-(4-bromobenzyl)-β-D-ribofuranosyl}-6-[2-(trimethylsilyl)ethoxy]-9H-purine

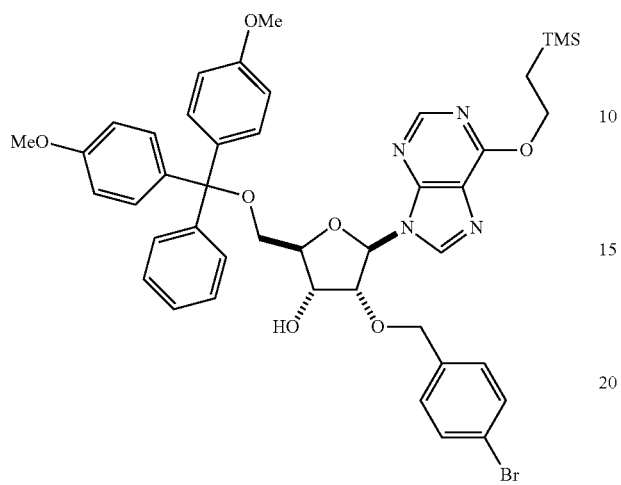

To a solution of 9-[2-O-(4-bromobenzyl)-β-D-ribofuranosyl]-6-[2-(trimethylsilyl)ethoxy]-9H-purine (8.75 g, 16.28 mmol) in pyridine (50 mL, 618 mmol) was added 4,4'-dimethoxytrityl chloride (6.62 g, 19.54 mmol). The mixture was stirred at ambient temperature for 2 h. Solvent was then evaporated in vacuo, and the residue purified by flash chromatography using 35-40% ethyl acetate in hexane to obtain 11.26 g (13.41 mmol, 82%) of the pure product. LCMS: for $C_{43}H_{47}BrN_4O_7Si$ calculated 839.8. found 814.4 [M+H]$^+$. $^1$H NMR (600 MHz, $CD_3CN$) δ: 8.27 (s, 1H), 8.06 (s, 1H), 7.42, (m, 2H), 7.27 (m, 7H), 7.10 (d, J=8.3 Hz, 2H), 6.82 (m, 4H), 6.08 (d, J=5.1 Hz, 1H), 4.70 (m, 4H), 4.54 (d, J=12.5 Hz, 1H), 4.47 (dd, J=9.6, 5.1 Hz, 1H), 4.17 (dd, J=8.5, 4.3 Hz, 1H), 3.77 (s, 6H), 3.57 (d, J=5.4 Hz, 1H), 3.33 (d, J=4.3 Hz, 2H), 1.26 (m, 2H), 0.11 (s, 9H). $^{13}$C NMR (600 MHz, $CD_3CN$) δ: 160.86, 158.86, 158.85 151.84, 145.26, 141.75, 137.24, 136.05, 136.01, 131.32, 130.26, 130.20, 129.92, 128.21, 127.05, 122.13, 121.35, 117.56, 113.23, 87.19, 86.37, 84.46, 80.09, 71.52, 69.95, 65.31, 63.51, 55.13, 17.29, -2.08

Intermediate 4

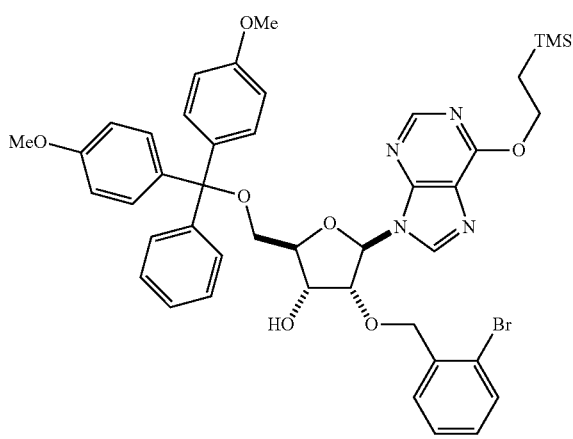 [SMILES: COc1ccc(C(OC[C@H]2O[C@@H](n3cnc4c(OCC[Si](C)(C)C)ncnc43)[C@H](OCc3ccccc3Br)[C@@H]2O)(c2ccccc2)c2ccc(OC)cc2)cc1]

Intermediate 4 was synthesized using procedures analogous to those described for synthesis of Intermediate 3 except that in Step A, instead of para-bromobenzyl bromide, ortho-bromobenzyl bromide was used.

Example 1

1,4-Anhydro-2-O-benzyl-5-O-[bis(4-methoxyphenyl)(phenyl)methyl]-3-O-[(2-cyanoethoxy) (dipropan-2-ylamino)phosphanyl]-D-ribitol

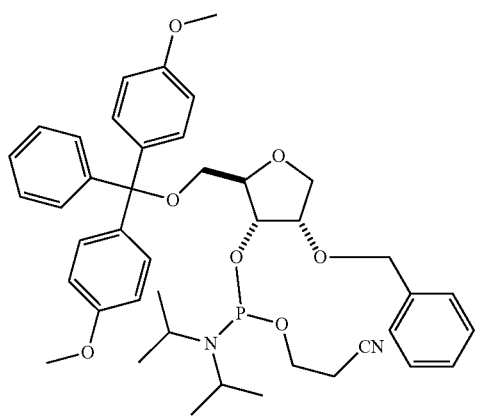

Step A 1,4-Anhydro-2-O-benzyl-3,5-O-(di-tert-butylsilanylidene)-D-ribitol

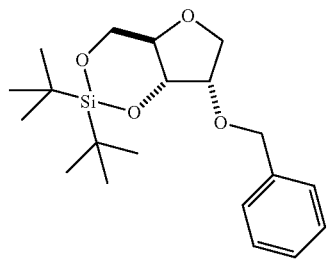 [SMILES: CC(C)(C)[Si]1(C(C)(C)C)OC[C@H]2OC[C@H](OCc3ccccc3)[C@@H]2O1]

To a solution of 1,4-Anhydro-3,5-O-(di-tert-butylsilanylidene)-D-ribitol (2.00 g, 7.29 mmol) in acetonitrile (20 mL) cooled at 0° C. was added molecular sieves (3 g), benzyl bromide (4.33 mL, 36.4 mmol) and 2-tert-butyl-imino-2-diethylamino-1,3-dimethyl-perhydro-1,3,2-diazaphosphorine (4.00 g, 14.58 mmol). The reaction mixture was slowly warmed to ambient temperature and stirred for 16 h. The reaction was quenched with the addition of MeOH (5 mL) and stirred for 5 min. The solid was filtered off with a layer of Celite. The filtrate was concentrated in vacuo, and the residue purified by flash chromatography using 5-10% ethyl acetate in hexane to obtain 2.30 g of the pure product (6.31 mmol, 87%). LCMS: for $C_{20}H_{32}O_4Si$ calculated 364.2. found 365.2 [M+H]$^+$. $^1$H NMR (600 MHz, $CD_3CN$) δ: 7.35 (m, 4H), 7.27 (t, J=7.1 Hz, 1H), 4.91 (d, J=12.0 Hz, 1H), 4.63 (d, J=11.9 Hz, 1H), 4.31 (dd, J=8.9, 4.6 Hz, 1H), 4.12 (m 2H), 3.97 (dd, J=9.5, 4.2 Hz, 1H), 3.87 (ddd, J=10.0, 10.0, 4.7 Hz, 1H), 3.80 (m, 2H), 1.05 (s, 9H), 1.01 (s, 9H).

$^{13}$C NMR (600 MHz, CD$_3$CN) δ: 128.44, 127.55, 117.57, 79.74, 77.24, 73.52, 73.06, 72.08, 68.27, 27.02, 26.76.

Step B 1,4-Anhydro-2-O-benzyl-D-ribitol

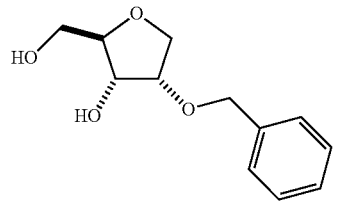 [SMILES: OC[C@H]1OC[C@H](OCc2ccccc2)[C@@H]1O]

To a mixture of 1,4-anhydro-2-O-benzyl-3,5-O-(di-tert-butylsilanylidene)-D-ribitol (2.60 g, 7.13 mmol) and potassium fluoride (4.14 g, 71.3 mmol) in THF (30 mL) was added TBAF (1 M in THF, 3.63 mL, 3.63 mmol). The mixture was stirred at 50° C. for 16 h. It was then cooled to ambient temperature and filtered though a layer of Celite, and washed with ACN (50 mL). The filtrate was concentrated in vacuo, and the residue purified by flash chromatography using 25-30% ethyl acetate in hexane to obtain 1.05 g (4.68 mmol, 66%) of the pure product. LCMS: for C$_{12}$H$_{16}$O$_4$ calculated 224.1. found 225.0 [M+H]$^+$ and 247.0 [M+Na]$^+$. $^1$H NMR (600 MHz, CD$_3$CN) δ: 7.37 (m, 4H), 7.30 (tt, J=7.0, 1.6 Hz, 1H), 4.61 (dd, J=22.6, 11.9 Hz, 2H), 4.00 (m, 2H), 3.92 (dd, J=9.5, 5.1 Hz, 1H), 3.75 (dd, J=9.6, 3.7 Hz, 1H), 3.66 (ddd, J=4.5, 4.5, 3.6 Hz, 1H), 3.60 (dd, J=12.0, 3.0, 1H), 3.48 (m, 1H), 3.06 (d, J=6.3 Hz 1H), 2.80 (s, 1H). $^{13}$C NMR (600 MHz, CD$_3$CN) δ: 128.56, 128.02, 127.86, 117.57, 83.98, 78.77, 71.84, 71.67, 70.17, 62.21.

Step C 1,4-Anhydro-2-O-benzyl-5-O-[bis(4-methoxyphenyl)(phenyl)methyl]D-ribitol

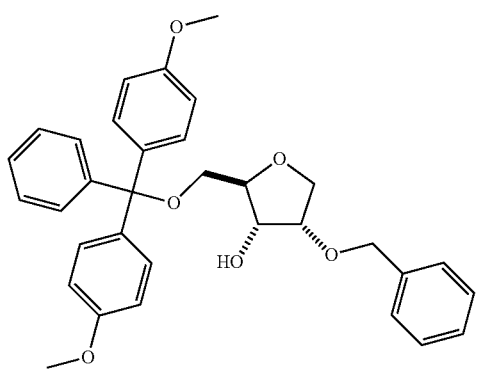 [SMILES: COc1ccc(C(OC[C@H]2OC[C@H](OCc3ccccc3)[C@@H]2O)(c2ccccc2)c2ccc(OC)cc2)cc1]

To a solution of 1,4-anhydro-2-O-benzyl-D-ribitol (1.0 g, 4.46 mmol) in pyridine (20 mL, 247 mmol) was added 4,4'-dimethoxytrityl chloride (4.53 g, 13.38 mmol). The mixture was stirred at ambient temperature for 2 h. Solvent was then evaporated in vacuo, and the residue purified by flash chromatography using 25-30% ethyl acetate in hexane to obtain 1.65 g (3.13 mmol, 70%) of the pure product. LCMS: for C$_{33}$H$_{34}$O$_6$ calculated 526.2. found 549.2 [M+H]$^+$. $^1$H NMR (600 MHz, CD$_3$CN) δ: 7.42, (m, 2H), 7.37 (m, 4H), 7.30 (m, 7H), 7.21 (tt, J=7.3, 1.1 Hz, 1H), 6.85 (m, 4H), 4.61 (d, J=3.4 Hz, 2H), 4.05 (dd, J=9.9, 4.7 Hz, 1H), 4.01 (m, 2H), 3.81 (m, 2H), 3.76 (s, 2H), 3.76 (s, 6H), 3.17 (dd, J=10.2, 3.2 Hz, 1H), 3.00 (dd, J=10.2, 5.0, 1H), 2.97 (s, 1H). $^{13}$C NMR (600 MHz, CD$_3$CN) δ: 158.84, 130.21, 128.59, 128.27, 128.01, 127.88, 126.98, 117.53, 113.22, 82.73, 78.59, 72.28, 71.87, 70.21, 64.44, 55.11.

Step D 1,4-Anhydro-2-O-benzyl-5-O-[bis(4-methoxyphenyl)(phenyl)methyl]-3-O-[(2-cyanoethoxy) (dipropan-2-ylamino)phosphanyl]-D-ribitol

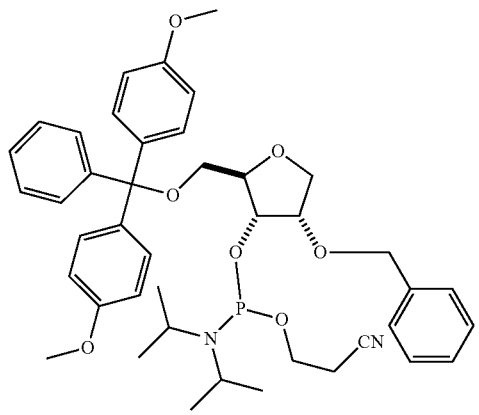

To a cooled solution (0° C.) of 1,4-anhydro-2-O-benzyl-5-O-[bis(4-methoxyphenyl)(phenyl)methyl]D-ribitol (1.60 g, 3.04 mmol) and N,N-diisopropylethylamine (1.59 mL, 9.11 mmol) in DCM (20 mL), 2-cyanoethyl-N, N-diisopropylchlorophosphoramidite (1.44 g, 6.08 mmol) and 1-methylimidazole (0.12 mL, 1.519 mmol) were added. The reaction mixture was warmed to ambient temperature and stirred for 90 min. The reaction was then quenched with methanol (5 mL) and stirred for 5 min. The solvent was then removed in vacuo, and the residue was purified by flash chromatography using 20% ethyl acetate in hexane to obtain 0.94 g (1.293 mmol, 42.6%) of the pure product. LCMS: for C$_{42}$H$_{51}$N$_2$O$_7$P calculated 726.3. found 727.3 [M+H]$^+$ and 749.4 [M+Na]$^+$ $^{31}$P NMR (400 MHz, CD$_3$CN) δ: 149.94, 149.70.

Example 2

2'-O-benzyl-5'-O-[bis(4-methoxyphenyl)(phenyl)methyl]-3'-O-[(2-cyanoethoxy)(dipropan-2-ylamino)phosphanyl]inosine

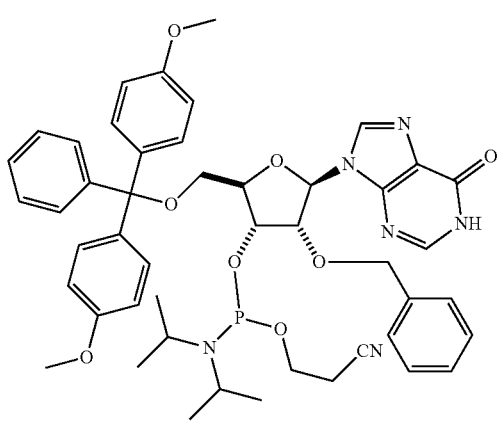

Step A

9-[2-O-benzyl-3,5-O-(di-tert-butylsilanylidene)-β-D-ribofuranosyl]-6-[2-(trimethylsilyl)ethoxy]-9H-purine

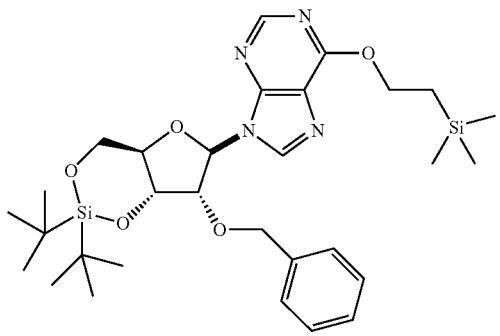 [SMILES: CC(C)(C)[Si]1(C(C)(C)C)OC[C@H]2O[C@@H](n3cnc4c(OCC[Si](C)(C)C)ncnc43)[C@H](OCc3ccccc3)[C@@H]2O1]

Under the protection of N₂, 9-[3,5-O-(di-tert-butylsilanylidene)-β-D-ribofuranosyl]-6-[2-(trimethylsilyl)ethoxy]-9H-purine (1.65 g, 3.24 mmol) was dissolved into 50 mL anhydrous acetonitrile with 3 Å molecular sieves (3 g). After the mixture was cooled to 0° C., 2-tert-butylimino-2-diethylamino-1,3-dimethylperhydro-1,3,2-diazaphosphorine (BEMP) (1.88 mL, 6.49 mmol) followed immediately by benzyl bromide (1.94 mL, 16.22 mmol) were added with exclusion of moisture. The reaction was then warmed up gradually from 0° C. to room temperature and stirred at room temperature for 2 h. The mixture was quenched with methanol (5 mL) and the solvents were evaporated under the reduced pressure. The residue was purified by column chromatography (gradient: Hexane with EtOAc 0-50%) to produce 1.72 g (2.87 mmol, 88%) final product. LCMS: for $C_{30}H_{46}N_4O_5Si_2$ calculated 598.3. found 599.1 [M++H]⁺. ¹H NMR (600 MHz, CD₃CN) δ: 8.45 (s, 1H), 8.01 (s, 1H), 7.40 (m, 2H), 7.33 (m, 2H), 7.27 (m, 1H), 6.13 (s, 1H), 4.98 (d, J=12.0 Hz, 1H), 4.77 (m, 2H), 4.67 (m, 2H), 4.46 (d, J=4.9 Hz, 1H), 4.41 (dd, J=9.1, 5.0 Hz, 1H), 4.20 (ddd, J=10.1, 10.1, 4.9 Hz, 1H), 4.06 (dd, J=10.3, 9.3 Hz, 1H), 1.22 (m, 2H), 1.11 (s, 9H), 1.04 (s, 9H). ¹³C NMR (600 MHz, CD₃CN) δ: 152.12, 141.40, 128.50, 127.79, 127.69, 117.52, 117.15, 89.73, 80.76, 76.91, 74.96, 72.67, 67.42, 65.33, 27.00, 26.71, 17.21, −0.85, −2.14.

Step B

2'-O-benzylinosine

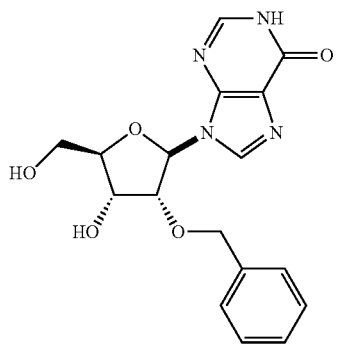 [SMILES: O=c1[nH]cnc2c1ncn2[C@@H]1O[C@H](CO)[C@@H](O)[C@H]1OCc1ccccc1]

To a mixture of 9-[2-O-benzyl-3,5-O-(di-tert-butylsilanylidene)-β-D-ribofuranosyl]-6-[2-(trimethylsilyl)ethoxy]-9H-purine (1.72 g, 2.87 mmol) and potassium fluoride (1.50 g, 25.80 mmol) in THF (30 mL) was added TBAF (1 M in THF, 2.87 mL, 2.87 mmol). The mixture was stirred at 55° C. for 2 h. After it was cooled to room temperature, the reaction was filtered and washed with THF (30 mL). The filtrate was evaporated under the reduced pressure and the residue was purified by flash chromatography (gradient: dichloromethane with methanol 0-8%) to produce 1.00 g (2.79 mmol, 97%) product. LCMS: for $C_{17}H_{18}N_4O_5$ calculated 358.1. found 358.9 [M+H]⁺. (600 MHz, CD₃OD) δ: 8.17 (s, 1H), 7.92 (s, 1H), 7.10 (m, 5H), 6.03 (d, J=6.3 Hz, 1H), 4.72 (d, J=12.4 Hz, 1H), 4.50 (dd, J=6.1, 5.1 Hz, 1H), 4.46 (d, J=12.4 Hz, 1H), 4.42 (dd, J=4.8, 2.9 Hz, 1H), 4.15 (dd, J=5.8, 2.9 Hz, 1H), 3.81 (dd, J=12.4, 2.8 Hz, 1H), 3.71 (dd, J=12.4, 2.9 Hz, 1H). ¹³C NMR (600 MHz, CD₃OD) δ: 148.00, 145.36, 139.90, 137.53, 128.00, 127.88, 127.68, 87.82, 87.12, 80.38, 72.15, 69.57, 61.93.

Step C

2'-O-benzyl-5'-O-[bis(4-methoxyphenyl)(phenyl)methyl]inosine

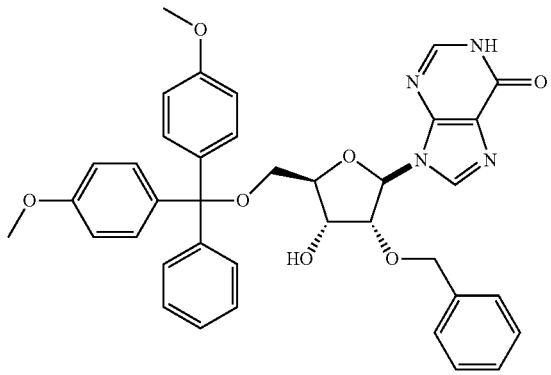 [SMILES: COc1ccc(C(OC[C@H]2O[C@@H](n3cnc4c(=O)[nH]cnc43)[C@H](OCc3ccccc3)[C@@H]2O)(c2ccccc2)c2ccc(OC)cc2)cc1]

Under the protection of N₂, to a solution of 2'-O-benzylinosine (1.0 g, 2.79 mmol) in 10 mL pyridine was added 4,4'-dimethoxytrityl chloride (2.36 g, 6.98 mmol). The mixture was stirred at room temperature for 2 h. The reaction was diluted with 100 mL dichloromethane and quenched with 100 mL saturated NaHCO3 solution. After the aqueous layer was extracted with dichloromethane (100 mL) three times, the organic layers were combined and evaporated. The residue was purified by flash chromatography (gradient: hexane with EtOAc 0-45%, with 1% triethylamine in both hexane and EtOAc) to produce 1.80 g (2.72 mmol, 98%) product. LCMS: for $C_{38}H_{36}N_4O_7$ calculated 660.3. found 661.2 [M+H]⁺. ¹H NMR (600 MHz, CD₃CN) δ: 7.83 (s, 1H), 7.80 (s, 1H), 7.39 (m, 2H), 7.23 (m, 12H), 6.82 (m, 4H), 6.02 (d, J=5.0 Hz, 1H), 4.71 (d, J=12.2 Hz, 1H), 4.59 (d, J=12.2 Hz, 1H), 4.54 (dd, J=5.1, 5.1 Hz, 1H), 4.42 (dd, J=9.6, 4.8 Hz, 1H), 4.14 (dd, J=8.4, 4.2 Hz, 1H), 3.64 (m, 1H), 3.57 (m, 1H). ¹³C NMR (600 MHz, CD₃CN) δ: 158.88, 156.87, 145.48, 145.18, 138.51, 136.09, 135.98, 130.23, 128.50, 128.24, 128.16, 128.08, 128.07, 128.04, 128.00, 127.08, 117.58, 117.08, 117.04, 113.264, 86.91, 84.49, 80.70, 72.29, 69.84, 63.55, 62.88, 55.15, 52.76.

Step D

2'-O-benzyl-5'-O-[bis(4-methoxyphenyl)(phenyl)methyl]-3'-O-[(2-cyanoethoxy)(dipropan-2-ylamino)phosphanyl]inosine

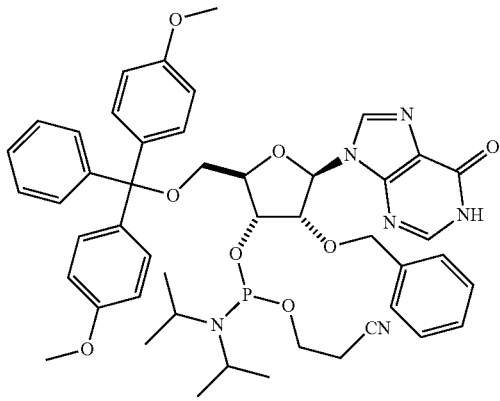 [SMILES: COc1ccc(C(OC[C@H]2O[C@@H](n3cnc4c(=O)[nH]cnc43)[C@H](OCc3ccccc3)[C@@H]2OP(OCCC#N)N(C(C)C)C(C)C)(c2ccccc2)c2ccc(OC)cc2)cc1]

Under the protection of $N_2$, 2-cyanoethyl-N, N-diisopropylchlorophosphoramidite (1.21 mL, 5.45 mmol) was added drop-wise to a 0° C. anhydrous tetrahydrofuran (12 mL) solution of 2'-O-benzyl-5'-O-[bis(4-methoxyphenyl)(phenyl)methyl]inosine (1.80 g, 2.72 mmol), N,N-diisopropylethylamine (1.42 mL, 8.17 mmol)), and 1-methylimidazole (0.11 mL, 1.36 mmol). The reaction was gradually warmed to room temperature and stirred for 60 min. The reaction was then quenched with methanol (5 mL) and stirred for 5 min. After the solvent was removed under the reduced pressure, the residue was purified by flash chromatography (gradient: methylene chloride with methanol 0-4%, with 1% triethylamine in both methylene chloride and methanol) to produce 1.83 g (78%, 2.13 mmol) final product. LCMS: for $C_{47}H_{53}N_6O_8P$ calculated 860.4. found 861.3 $[M+H]^+$ and 884.4 $[M+Na]^+$. $^{31}P$ NMR (600 MHz, $CD_3CN$) δ: 150.82, 150.55.

Example 3

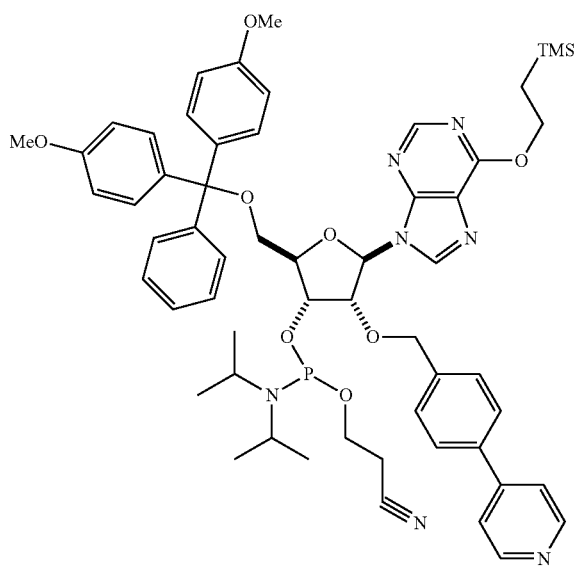

Step A

9-{5-O-[bis(4-methoxyphenyl)(phenyl)methyl]-2-O-[4-(pyridin-4-yl)benzyl]-β-D-ribofuranosyl}-6-[2-(trimethylsilyl)ethoxy]-9H-purine

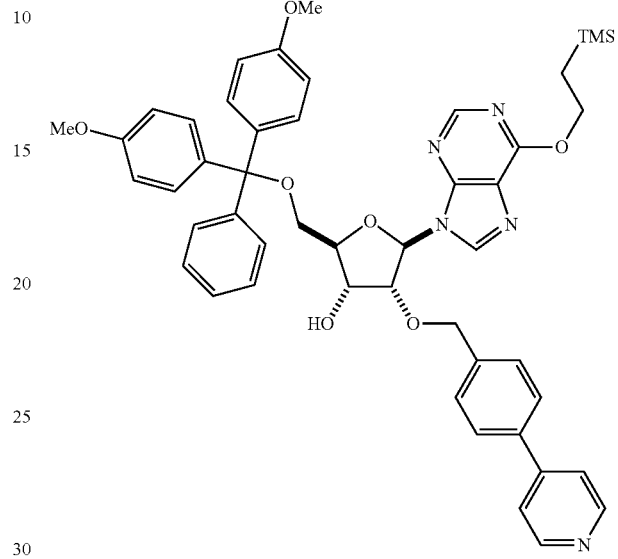

Palladium (II) acetate (58.8 mg, 0.262 mmol) and butyl di-1-adamantylphosphine (169 mg, 0.472 mmol) were added to 1,2-dichloroethane (10 mL) at ambient temperature and stirred for 20 min. The solvent was then removed in vacuo. To this residue was added a solution of 9-{5-O-[bis(4-methoxyphenyl)(phenyl)methyl]-2-o-(4-bromobenzyl)-β-D-ribofuranosyl}-6-[2-(trimethylsilyl)ethoxy]-9H-purine (Intermediate 3, 2.20 g, 2.62 mmol) and pyridine-4-boronic acid (580 mg, 4.72 mmol) in 2-methyl-THF (40 mL), followed by the addition of saturated aqueous solution of potassium carbonate (2.17 g, 15.7 mmol). The mixture was heated at 80° C. and stirred for 16 h. After cooled to ambient temperature, the mixture was partitioned between water (50 mL) and DCM (50 mL). The aqueous layer was washed with DCM (20 mL) three times. The combined organic layers were dried with anhydrous sodium sulfate and then solvent was evaporated in vaduo. The residue was purified with flash chromatography using 85% ethyl acetate in hexane to obtain 1.90 g (2.27 mmol, 87%) of the pure product. LCMS: for $C_{48}H_{51}N_5O_7Si$ calculated 838.0. found 838.6 $[M+H]^+$. $^1H$ NMR (600 MHz, $CD_3CN$) δ: 8.61 (m, 2H), 8.21 (s, 1H), 8.04 (s, 1H), 7.54, (m, 2H), 7.46 (m, 2H), 7.40 (m, 2H), 7.23 (m, 7H), 6.80 (m, 4H), 6.08 (d, J=5.5 Hz, 1H), 4.79 (m, 2H), 4.54 (m, 4H), 4.20 (dd, J=8.3, 4.3 Hz, 1H), 3.74 (s, 6H), 3.33 (d, J=4.4 Hz, 2H), 1.16 (m, 2H), 0.09 (s, 9H). $^{13}C$ NMR (600 MHz, $CD_3CN$) δ: 160.73, 158.85, 158.83, 151.79, 151.72, 150.37, 147.45, 145.27, 141.90, 139.01, 137.30, 136.08, 136.03, 130.25, 130.19, 128.75, 128.20, 128.02, 127.03, 126.80, 122.09, 121.59, 117.88, 117.58, 117.40, 113.22, 87.23, 86.35, 84.62, 79.82, 71.88, 70.00, 65.16, 63.59, 55.11, 17.19, −2.13.

Step B

9-{5-O-[bis(4-methoxyphenyl)(phenyl)methyl]-3-O-[(2-cyanoethoxy)(dipropan-2-ylamino)phosphanyl]-2-o-[4-(pyridin-4-yl)benzyl]-β-D-ribofuranosyl}-6-[2-(trimethylsilyl)ethoxy]-9H-purine

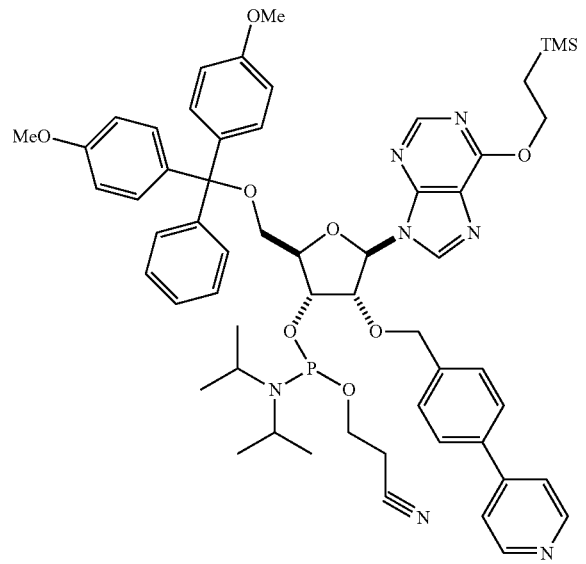

To a cooled solution (0° C.) of 9-{5-O-[bis(4-methoxyphenyl)(phenyl)methyl]-2-o-[4-(pyridin-4-yl)benzyl]-β-D-ribofuranosyl}-6-[2-(trimethylsilyl)ethoxy]-9H-purine (1.85 g, 2.21 mmol) and N,N-diisopropylethylamine (856 mg, 6.62 mmol) in DCM (20 mL), 2-cyanoethyl-N, N-diisopropylchlorophosphoramidite (1.05 g, 4.42 mmol) and 1-methylimidazole (91 mg 1.10 mmol) were added. The reaction mixture was warmed to ambient temperature and stirred for 90 min. The reaction was then quenched with methanol (5 mL) and stirred for 5 min. The solvent was then removed in vacuo, and the residue was purified by flash chromatography using 65% ethyl acetate in hexane to obtain 1.91 g (1.84 mmol, 83%) of the pure product. LCMS: for $C_{57}H_{68}N_7O_8PSi$ calculated 1038.3. found 1039.4 [M+H]$^+$ $^{31}$P NMR (600 MHz, CD$_3$CN) δ: 150.70, 150.65.

Example 4

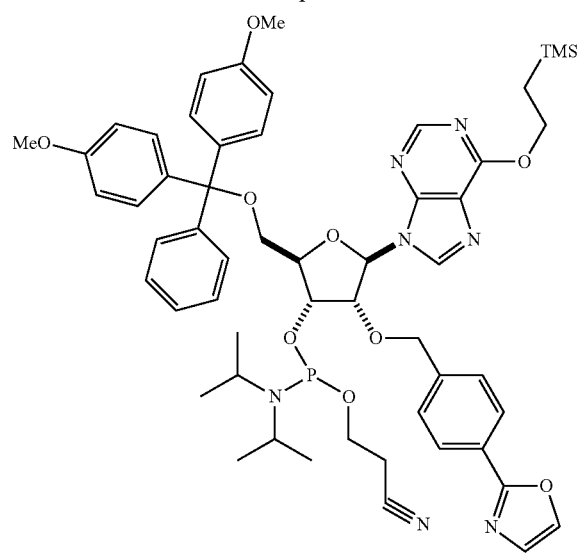

Step A

9-{5-O-[bis(4-methoxyphenyl)(phenyl)methyl]-2-o-[4-(1,3-oxazol-2-yl)benzyl]-β-D-ribofuranosyl}-6-[2-(trimethylsilyl)ethoxy]-9H-purine Tris[dibenzylideneacetone]dipalladium(0) (131 mg, 0.143 mmol) and [4-(N,N-dimethylamino)phenyl]di-tert-butylphosphine (152 mg, 0.572 mmol) were added to THF (10 mL) at ambient temperature and stirred for 30 min. To this mixture was then added a solution of 9-{5-O-[bis(4-methoxyphenyl)(phenyl)methyl]-2-o-(4-bromobenzyl)-β-D-ribofuranosyl}-6-[2-(trimethylsilyl)ethoxy]-9H-purine (Intermediate 3, 800 mg, 0.953 mmol) and 2-(tri-N-butyl-stannyl)oxazole (1.02 g, 2.86 mmol) in THF (15 mL). The mixture was heated at 50° C. and stirred for 16 h. After cooled to ambient temperature, the mixture was filtered through a layer of Celite. The filtrate was concentrated in vacuo. The residue was purified with flash chromatography using 55-60% ethyl acetate in hexane to obtain 735 mg (0.888 mmol, 88%) of the pure product. LCMS: for $C_{46}H_{49}N_5O_8Si$ calculated 828.0. found 828.3 [M+H]$^+$. $^1$H NMR (600 MHz, CD$_3$CN) δ: 8.22 (s, 1H), 8.05 (s, 1H), 7.88 (s, 1H), 7.77 (d, J=8.2 Hz, 2H), 7.41 (d, J=8.0 Hz, 2H), 7.25 (m, 7H), 6.80 (m, 4H), 6.09, (d, J=5.5 Hz, 1H), 4.78 (m, 2H), 4.58 (m, 4H), 4.19 (dd, J=8.4, 4.3 Hz, 1H), 3.76 (s, 6H), 3.59 (d, J=5.2 Hz, 2H), 3.33 (d, J=4.5 Hz, 2H), 1.21 (m, 2H), 0.10 (s, 9H). $^{13}$C NMR (600 MHz, CD$_3$CN) δ: 158.82, 151.74, 145.21, 141.78, 140.29, 139.61, 136.05, 136.00, 130.21, 130.17, 128.58, 128.40, 128.18, 127.98, 127.00, 126.00, 117.54, 117.07, 113.19, 87.14, 86.34, 84.55, 80.02, 71.85, 69.98, 65.20, 63.53, 55.08, 17.18, −2.13.

Step B

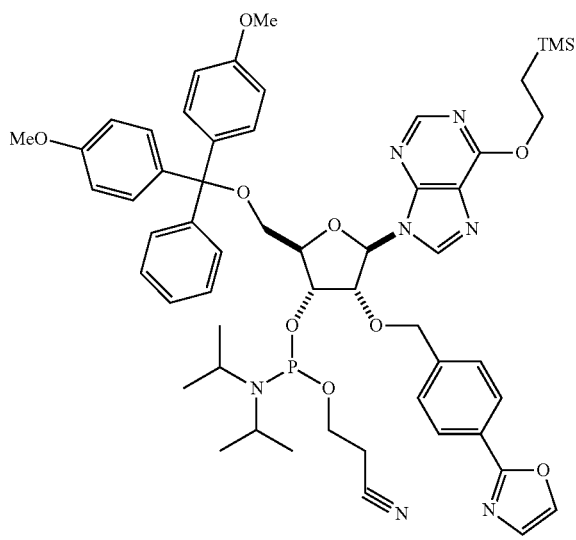

To a cooled solution (0° C.) of 9-{5-O-[bis(4-methoxyphenyl)(phenyl)methyl]-2-o-[4-(1,3-oxazol-2-yl)benzyl]-β-D-ribofuranosyl}-6-[2-(trimethylsilyl)ethoxy]-9H-purine (1.63 g, 1.97 mmol) and N,N-diisopropylethylamine (763 mg, 5.91 mmol) in DCM (20 mL), 2-cyanoethyl-N, N-diisopropylchlorophosphoramidite (932 mg, 3.94 mmol) and 1-methylimidazole (81 mg 0.984 mmol) were added. The reaction mixture was warmed to ambient temperature and stirred for 90 min. The reaction was then quenched with methanol (5 mL) and stirred for 5 min. The solvent was then removed in vacuo, and the residue was purified by flash chromatography using 55% ethyl acetate in hexane to obtain 1.57 g (1.53 mmol, 78%) of the pure product. LCMS: for $C_{55}H_{66}N_7O_9PSi$ calculated 1027.4. found 1028.5 [M+H]$^+$ $^{31}$P NMR (600 MHz, CD$_3$CN) δ: 150.69, 150.64.

Example 5

Step A

9-[3,5-O-(di-tert-butylsilanylidene)-β-D-erythro-pentofurnaosyl-2-ulose]-6-[2-(trimethylsilyl)ethoxy]-9H-purine To a solution of 9-[3,5-O-(di-tert-butylsilanylidene)-β-D-ribofuranosyl]-6-[2-(trimethylsilyl)ethoxy]-9H-purine. (50 g, 98 mmol), and DCC (58.8 g, 285 mmol) in DMSO (200 ml) and Benzene (250 ml), Dichloroacetic acid (2.8 ml, 33 mmol) was added drop-wise at 0° C. under the protection of N$_2$. The reaction was warmed gradually to RT and was stirred for 4 hours. The reaction mixture was partitioned between H$_2$O (800 ml) and EtOAc (800 ml) and separated. After the organic layer was washed H$_2$O (800 ml) three times and dried with MgSO4. The solvent was evaporated to produce the 51 g crude product. The crude product was a mixture of the desired 2'-ketone and its corresponding 2'-geminal diol. It was applied into the next step of synthesis without any further purification. LCMS 9-[3,5-O-(di-tert-butylsilanylidene)-β-D-erythro-pentofurnaosyl-2-ulose]-6-[2-(trimethylsilyl)ethoxy]-9H-purine: for $C_{23}H_{38}N_4O_5Si_2$ calculated 506.7. found 539.2 [M+Na]$^+$. LCMS (4aR,6R,7aR)-2,2-di-tert-butyl-6-{6-[2-(trimethylsilyl)ethoxy]-9H-purin-9-yl}dihydro-4H-furo[3,2-d][1,3,2]dioxasiline-7,7(6H)-diol: for $C_{23}H_{40}N_4O_6Si_2$ calculated 524.7. found 525.1 [M+H]$^+$.

Step B

9-[3,5-O-(di-tert-butylsilanylidene)-β-D-arabinofuranosyl]-6-[2-(trimethylsilyl)ethoxy]-9H-purine To a solution of crude 9-[3,5-O-(di-tert-butylsilanylidene)-β-D-erythro-pentofurnaosyl-2-ulose]-6-[2-(trimethylsilyl)ethoxy]-9H-purine (51 g, 97 mmol) in Ethanol (150 ml), Sodium borohydride (7.4 g, 194 mmol) was added under the protection of N$_2$. The reaction was stirred under RT for 2 hours. After the reaction was quenched with aqueous HCl, the solvent was removed under vacuum and the residue was partitioned between water (500 ml) and DCM (500 ml) and separated. The aqueous layer was washed DCM (500 ml) three times, all of the organic layers were combined and dried with MgSO4 and evaporated. Resulting residue was purified by column chromatography (gradient: hexane with EtOAc 0-50%) and 25.9 g (50.9 mmol, 51.9% two steps) pure compound obtained. LCMS: for $C_{23}H_{40}N_4O_5Si_2$ calculated 508.8. found 509.1 [M+H]$^+$. $^1$H NMR (600 MHz, CD$_3$CN) δ: 8.42 (s, 1H), 8.23 (s, 1H), 6.40 (d, J=7.1, 2H), 4.68 (m, 2H), 4.61 (t, J=8.9 Hz, 1H), 4.51 (dd, J=8.2, 7.3 Hz, 1H), 4.33 (dd, J=9.1, 5.3 Hz, 1H), 4.18 (m, 1H), 3.85 (m, 1H), 1.22 (m, 2H), 1.09 (s, 9H), 1.01 (s, 9H), 0.07 (s, 9H). $^{13}$C NMR (600 MHz, CD$_3$CN) δ: 160.77, 152.10, 152.01, 143.19, 120.77, 83.67, 80.25, 75.08, 73.69, 67.16, 65.38, 26.80, 26.43, 22.34, 19.75, 17.24.

Step C

9-[2-O-benzyl-3,5-O-(di-tert-butylsilanylidene)-β-D-arabinofuranosyl]-6-[2-(trimethylsilyl)ethoxy]-9H-purine

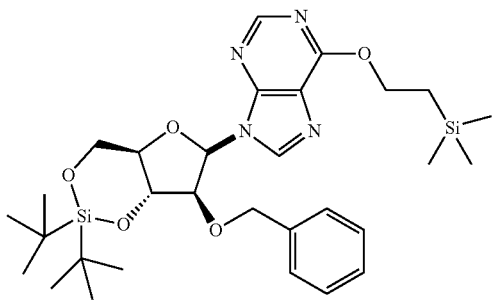

Under the protection of N$_2$, 9-[3,5-O-(di-tert-butylsilanylidene)-β-D-arabinofuranosyl]-6-[2-(trimethylsilyl)ethoxy]-9H-purine (1.95 g, 3.83 mmol) was dissolved into 50 mL anhydrous acetonitrile with 3 Å molecular sieves (3 g). After the mixture was cooled to 0° C., 2-tert-butylimino-2-diethylamino-1,3-dimethylperhydro-1,3,2-diazaphosphorine (BEMP) (2.22 mL, 7.67 mmol) followed immediately by benzyl bromide (2.30 mL, 19.16 mmol) were added with exclusion of moisture. The reaction was then warmed up gradually from 0° C. to room temperature and stirred at room temperature for 2 h. The mixture was quenched with methanol (5 mL) and the solvents were evaporated under the reduced pressure. The residue was purified by column chromatography (gradient: Hexane with EtOAc 0-50%) to produce 2.20 g (3.67 mmol, 96%) final product. LCMS: for $C_{30}H_{46}N_4O_5Si_2$ calculated 598.88. found 599.27 [M+H]$^+$. $^1$H NMR (600 MHz, CD$_3$CN) δ: 8.42 (s, 1H), 8.12 (s, 1H), 7.16 (m, 3H), 6.92-6.91 (m, 2H), 6.52 (d, J=7.0 Hz, 1H), 4.72 (t, J=8.9 Hz, 1H), 4.68-4.65 (m, 2H), 4.54 (d, J=12.0 Hz, 2H), 4.48 (dd, J=8, 7.3 Hz, 2H), 4.35 (d, J=9.1, 5.3 Hz, 1H), 4.3 (d, J=12.1 Hz, 1H), 4.15-4.12 (m, 1H), 3.88 (ddd, J=10, 10, 5.2 Hz, 1H), 1.22 (m, 2H), 1.10 (s, 9H), 1.03 (s, 9H), 0.08 (s, 9H). $^{13}$C NMR (600 MHz, CD$_3$CN) δ: 152.43, 152.13, 142.86, 137.56, 128.38, 127.83, 127.50, 106.38, 81.73, 81.63, 79.95, 73.26, 72.37, 67.17, 65.31, 27.10, 26.68, 17.24, −2.12.

Step D 9-(2-O-benzyl-β-D-arabinofuranosyl)-6-[2-(trimethylsilyl)ethoxy]-9H-purine

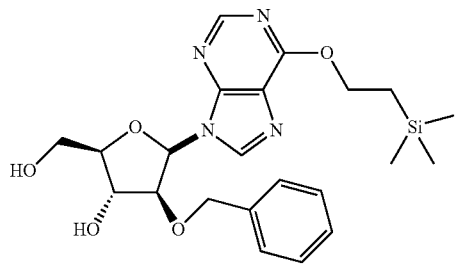

Hydrogen fluoride-pyridine (1.18 mL, 9.17 mmol) was carefully diluted with pyridine (5 mL) and then added dropwise to a solution of 9-[2-O-benzyl-3,5-O-(di-tert-butylsilanylidene)-β-D-arabinofuranosyl]-6-[2-(trimethylsilyl)ethoxy]-9H-purine (2.2 g, 3.67 mmol) in THF (100 mL) at 0° C. The mixture was stirred at 0° C. for 15 min. The reaction was quenched with methanol (10 mL) and then evaporated to dryness. The residue was diluted with 50 mL dichloromethane and was washed with water (100 mL) three times, the organic layers was evaporated to obtain 1.60 g (3.49 mmol, 95%) of the pure product. LCMS: for $C_{22}H_{30}N_4O_5Si$ calculated 458.583. found 459.1 [M+H]$^+$. $^1$H NMR (600 MHz, CD$_3$OD) δ: 8.46 (s, 1H), 8.40 (s, 1H), 7.10-7.06 (m, 3H), 6.82 (d, J=6.6 Hz, 2H), 6.53 (d, J=5.5 Hz, 1H), 4.73-4.70 (m, 2H), 4.57-4.54 (m, 2H), 4.47 (t, J=5.6, 1H), 4.27 (m, 2H), 3.93 (m, 1H), 3.86-3.79 (m, 2H), 1.26 (dd, J=9.6, 7.2 Hz, 2H), 0.10 (s, 9H). $^{13}$C NMR (600 MHz, CD$_3$OD) δ: 152.02, 142.97, 127.98, 127.50, 127.26, 83.92, 83.72, 83.51, 73.30, 72.61, 65.44, 60.70, 17.28, −2.59.

Step E

9-{5-O-[bis(4-methoxyphenyl)(phenyl)methyl]-2-O-benzyl-β-D-arabinofuranosyl}-6-[2-(trimethylsilyl)ethoxy]-9H-purine

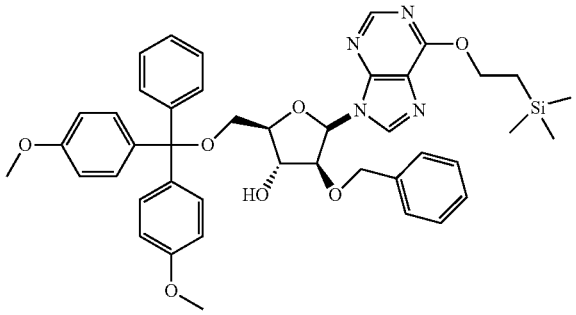

Under the protection of N$_2$, to a solution of 9-(2-O-benzyl-β-D-arabinofuranosyl)-6-[2-(trimethylsilyl)ethoxy]-9H-purine (1.60 g, 3.49 mmol) in 20 mL pyridine was added 4,4'-dimethoxytrityl chloride (2.13 g, 6.28 mmol). The mixture was stirred at room temperature for 2 h. The reaction was diluted with 100 mL dichloromethane and quenched with 100 mL saturated NaHCO3 solution. After the aqueous layer was extracted with dichloromethane (100 mL) three times, the organic layers were combined and evaporated. The residue was purified by flash chromatography (gradient: hexane with EtOAc 0-100%, with 1% triethylamine in both hexane and EtOAc) to produce 1.18 g (1.55 mmol, 44.4%) product. LCMS: for $C_{43}H_{48}N_4O_7Si$ calculated 760.9. found 762.5 [M+H]$^+$. $^1$H NMR (600 MHz, CD$_3$CN) δ: 8.39 (s, 1H), 8.10 (s, 1H), 7.42-7.40 (m, 2H), 7.29-7.13 (m, 10H), 6.86-6.85 (m, 2H), 6.81-6.77 (m, 4H), 6.50 (d, J=5.5 Hz, 1H), 4.69-4.65 (m, 2H), 4.49-4.45 (m, 2H), 4.24-4.21 (m, 2H), 4.02 (m, 1H), 3.8 (dd, J=10.4, 6.3 Hz, 1H), 3.29 (dd, J=10.4, 3.5 Hz, 1H), 1.22 (m, 2H). 0.09 (s, 1H). $^{13}$C NMR (600 MHz, CD$_3$CN) δ: 160.82, 152.01, 142.44, 130.24, 130.21, 128.39, 128.25, 128.01, 127.86, 127.61, 127.05, 113.21, 83.56, 82.87, 82.37, 74.31, 72.54, 65.26, 63.56, 55.10, 17.27, −2.13.

Step F

9-{5-O-[bis(4-methoxyphenyl)(phenyl)methyl]-3-O-[(2-cyanoethoxy) (dipropan-2-ylamino)phosphanyl]-2-O-benzyl-β-D-arabinofuranosyl}-6-[2-(trimethylsilyl)ethoxy]-9H-purine

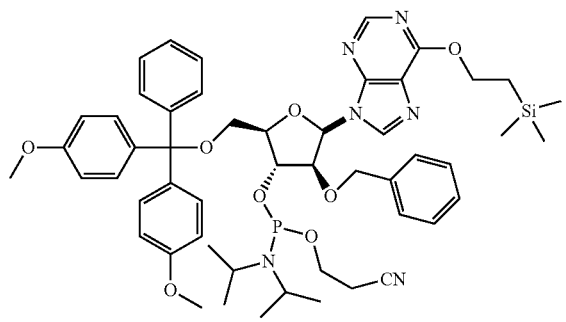

Under the protection of N$_2$, 2-cyanoethyl-N, N-diisopropylchlorophosphoramidite (0.69 mL, 3.10 mmol) was added drop-wise to a 0° C. anhydrous tetrahydrofuran (12 mL) solution of 9-{5-O-[bis(4-methoxyphenyl)(phenyl)methyl]-2-O-benzyl-β-D-arabinofuranosyl}-6-[2-(trimethylsilyl)ethoxy]-9H-purine (1.18 g g, 1.55 mmol), N,N-diisopropylethylamine (0.81 mL, 4.65 mmol)), and 1-methylimidazole (0.06 mL, 0.78 mmol). The reaction was gradually warmed to room temperature and stirred for 60 min. The reaction was then quenched with methanol (5 mL) and stirred for 5 min. After the solvent was removed under the reduced pressure, the residue was purified by flash chromatography (gradient: hexane with EtOAc 0-50%, with 1% triethylamine in both hexane and EtOAc) to produce 1.41 g (94.6%, 1.47 mmol) final product. LCMS: for $C_{52}H_{65}N_6O_8PSi$ calculated 961.167. found 961.6 [M+H]$^+$. $^{31}$P NMR (600 MHz, CD$_3$CN) δ: 150.65, 150.24.

Example 6

N-acetyl-2'-O-benzyl-5'-O-[bis(4-methoxyphenyl)(phenyl)methyl]-3'-O-[(2-cyanoethoxy)(dipropan-2-ylamino)phosphanyl]adenosine

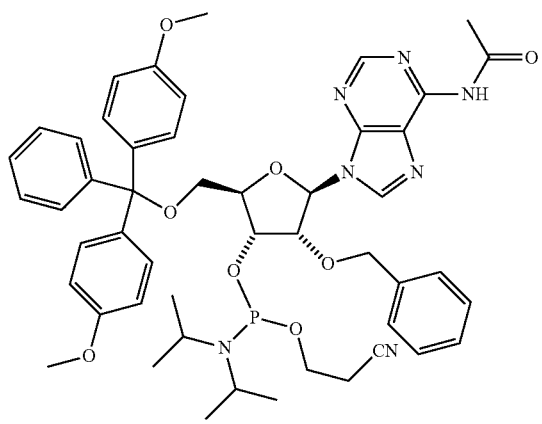 [SMILES: COc1ccc(C(OC[C@H]2O[C@@H](n3cnc4c(NC(C)=O)ncnc43)[C@H](OCc3ccccc3)[C@@H]2OP(OCCC#N)N(C(C)C)C(C)C)(c2ccccc2)c2ccc(OC)cc2)cc1]

The title compound was synthesized using a procedure analogous to that described under Example 2, with appropriate protecting groups present in the heterocyclic ring. LCMS: for $C_{46}H_{53}N_4O_9P$ calculated 836.36. found 836.20. $^{31}$P NMR (600 MHz, CDCl$_3$) δ: 150.76, 150.55.

Example 7

2'-O-benzyl-5'-O-[bis(4-methoxyphenyl)(phenyl)methyl]-3'-O-[(2-cyanoethoxy)(dipropan-2-ylamino)phosphanyl]uridine

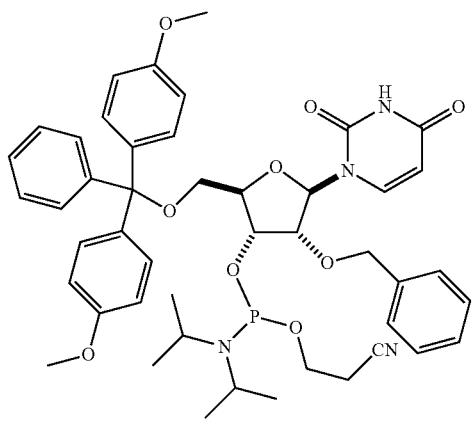

The title compound was synthesized using a procedure analogous to that described under Example 2, with appropriate protecting groups present in the heterocyclic ring. LCMS: for $C_{54}H_{58}N_7O_8P$ calculated 963.41. found 965.8 [M+H]$^+$ $^{31}$P NMR (600 MHz, CDCl$_3$) δ: 151.27, 151.76.

Example 8

2'-O-benzyl-5'-O-[bis(4-methoxyphenyl)(phenyl)methyl]-3'-O-[(2-cyanoethoxy)(dipropan-2-ylamino)phosphanyl]-N-(2-methylpropanoyl)-guanosine

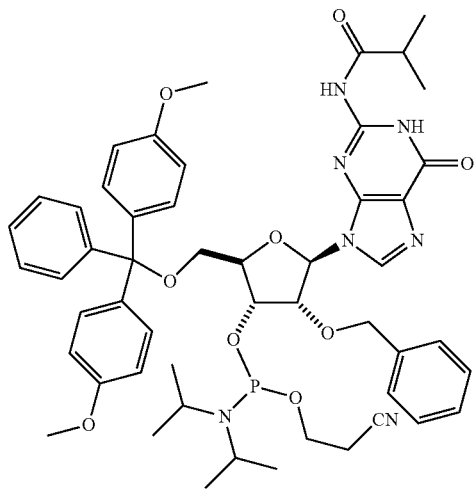

The title compound was synthesized using a procedure analogous to that described under Example 2, with appropriate protecting groups present in the heterocyclic ring. LCMS: for $C_{54}H_{58}N_7O_8P$ calculated 945.42. found 945.40. $^{31}P$ NMR (600 MHz, $CDCl_3$) δ: 150.76, 150.53.

Example 9

N-Acetyl-2'-O-benzyl-5'-O-[bis(4-methoxyphenyl)(phenyl)methyl]-3'-O-[(2-cyanoethoxy)(dipropan-2-ylamino)phosphanyl]-N-(2-methylpropanoyl)-cytidine

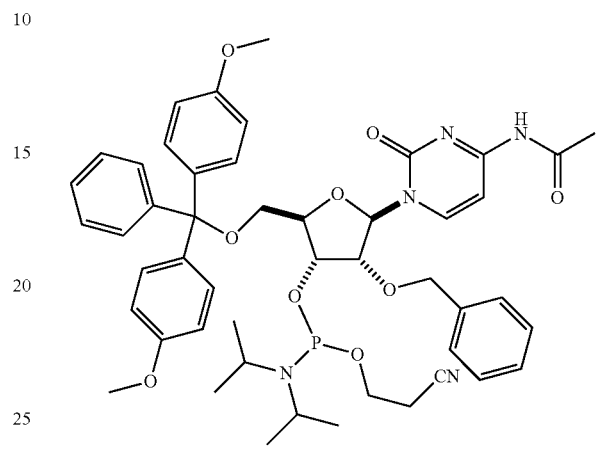

The title compound was synthesized using a procedure analogous to that described under Example 2, with appropriate protecting groups present in the heterocyclic ring. LCMS: for $C_{48}H_{56}N_5O_9P$ calculated 877.38. found 879.0 [M+H]$^+$ $^{31}P$ NMR (600 MHz, $CDCl_3$) δ: 150.66, 150.42.

---

What is claimed is:

1. A method for evaluating 1 or more chemical modifications in an siRNA, said method comprising:
   a) providing a siRNA oligomer with 1 or more sugar un-modified universal base containing nucleosides;
   b) measuring position-specific data to create a baseline data;
   c) providing a siRNA oligomer with 1 or more sugar modified universal base containing nucleosides at the same position of the un-modified universal base(s) of step a);
   d) measuring position-specific data,
   wherein a change in the position-specific data from step d) relative to the baseline data is indicative of siRNA function.

2. The method of claim 1, wherein the position-specific data is position-specific knockdown data.

3. The method of claim 1, wherein the evaluation of the position-specific data comprises detecting target mRNA degradation.

4. The method of claim 3, wherein the target mRNA degradation is detected by quantitative PCR.

5. The method of claim 1, wherein the universal base is a hydrogen atom, inosine, modified adenine, modified guanine, modified uracil, modified cytosine, thymine, modified thymine, 2-aminoadenosine, 5-methylcytosine, 2,6-diaminopurine, naphthyl, 3-nitropyrrole, imidazole-4-carboxamide, 5-nitroindole, nebularine, pyridone, or pyridinone.

6. The method of claim 1, wherein the universal base is inosine.

7. The method of claim 1, wherein the universal base is anhydroribitol.

8. The method of claim 1, wherein the sugar-modified universal base comprises a 2'-O-ribose modification.

9. The method of claim 8, wherein the 2'-O-ribose modification is a 2'-O-benzyl, 2'-O-methylene-(β-naphthyl), 2'-O-(2-difluoromethoxybenzyl), or 2'-O-methylene-(4-pyridyl) modification.

10. The method of claim 1, wherein the siRNA is a double stranded siRNA.

11. The method of claim 10, wherein the siRNA comprises overhangs.

12. The method of claim 1, wherein measuring position-specific data in step b) comprises contacting the siRNA oligomer of step a) with a target mRNA.

13. The method of claim 12, which further comprises detecting target mRNA degradation.

14. The method of claim 1, wherein measuring position-specific data in step d) comprises contacting the siRNA oligomer of step c) with a target mRNA.

15. The method of claim 14, which further comprises detecting target mRNA degradation.

16. The method of claim 1, wherein measuring position-specific data in step b) comprises contacting a cell with the siRNA oligomer of step a).

17. The method of claim 1, wherein measuring position-specific data in step d) comprises contacting a cell with the siRNA oligomer of step c).

18. The method of claim 1, which comprises comparing the position specific data from step d) to the baseline data.

* * * * *